(12) United States Patent
Dallwig et al.

(10) Patent No.: US 7,776,529 B2
(45) Date of Patent: Aug. 17, 2010

(54) METHINE-SUBSTITUTED CYANINE DYE COMPOUNDS

(75) Inventors: Jason Alfred Dallwig, Eugene, OR (US); David Carl Hagen, Eugene, OR (US); Ching-Ying Cheung, Eugene, OR (US); Gerald Alan Thomas, Springfield, OR (US); Stephen Yue, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 9 days.

(21) Appl. No.: 11/005,861

(22) Filed: Dec. 6, 2004

(65) Prior Publication Data

US 2005/0208534 A1    Sep. 22, 2005

Related U.S. Application Data

(60) Provisional application No. 60/527,142, filed on Dec. 5, 2003, provisional application No. 60/554,452, filed on Mar. 18, 2004.

(51) Int. Cl.
*A61K 31/4709* (2006.01)
*C07D 215/12* (2006.01)
*C12Q 1/68* (2006.01)

(52) U.S. Cl. .......................... 435/6; 514/314; 546/165
(58) Field of Classification Search .................. 546/165
See application file for complete search history.

(56) References Cited

U.S. PATENT DOCUMENTS

| | | | |
|---|---|---|---|
| 2,269,234 A | 1/1942 | Sprague | |
| 3,326,688 A | 6/1967 | Jenkins et al. | |
| 3,623,882 A | 11/1971 | Gotze et al. | |
| 3,840,377 A | 10/1974 | Sato et al. | |
| 3,890,155 A | 6/1975 | Nakamura et al. | |
| 3,988,513 A | 10/1976 | Matsuyama et al. | |
| 4,003,750 A | 1/1977 | Heseltine et al. | |
| 4,126,516 A | 11/1978 | Messing et al. | |
| 4,190,328 A | 2/1980 | Levine et al. | |
| 4,225,669 A | 9/1980 | Melnick et al. | |
| 4,304,908 A | 12/1981 | Frishberg et al. | |
| 4,336,321 A | 6/1982 | Kanada et al. | |
| 4,337,063 A | 6/1982 | Mihara et al. | |
| 4,343,782 A | 8/1982 | Shapiro | |
| 4,386,146 A | 5/1983 | Kishino et al. | |
| 4,424,201 A | 1/1984 | Valinsky et al. | |
| 4,508,821 A | 4/1985 | Mansour et al. | |
| 4,510,235 A | 4/1985 | Ukai et al. | |
| 4,520,110 A | 5/1985 | Stryer et al. | |
| 4,542,104 A | 9/1985 | Stryer et al. | |
| 4,544,546 A | 10/1985 | Wang et al. | |
| 4,554,546 A | 11/1985 | Herbreteau et al. | |
| 4,556,636 A | 12/1985 | Belly et al. | |
| 4,603,209 A | 7/1986 | Tsien et al. | |
| 4,639,421 A | 1/1987 | Sage, Jr. | |
| 4,665,024 A | 5/1987 | Mansour et al. | |
| 4,711,955 A | 12/1987 | Ward et al. | |
| 4,737,454 A | 4/1988 | Dattagupta et al. | |
| 4,740,891 A | 4/1988 | Kirkpatrick et al. | |
| 4,762,701 A | 8/1988 | Horan et al. | |
| 4,774,339 A | 9/1988 | Haugland et al. | |
| 4,783,401 A | 11/1988 | Horan et al. | |
| 4,810,636 A | 3/1989 | Corey et al. | |
| 4,812,409 A | 3/1989 | Babb et al. | |
| 4,837,141 A | 6/1989 | Kohno et al. | |
| 4,849,362 A | 7/1989 | DeMarinis et al. | |
| 4,859,582 A | 8/1989 | Stryer et al. | |
| 4,859,584 A | 8/1989 | Horan et al. | |
| 4,883,867 A | 11/1989 | Lee et al. | |
| 4,886,744 A | 12/1989 | Arnost et al. | |
| 4,921,805 A | 5/1990 | Gebeyehu et al. | |
| 4,937,198 A | 6/1990 | Lee et al. | |

(Continued)

FOREIGN PATENT DOCUMENTS

CA    2119126    4/1993

(Continued)

OTHER PUBLICATIONS

STN International, CAPLUS Database, accession No. 1959:5447, Reg. Nos. 108519-76-2 and 109724-08-5 (2006).*

(Continued)

*Primary Examiner*—Rebecca L Anderson
*Assistant Examiner*—Shawquia Young
(74) *Attorney, Agent, or Firm*—Life Technologies Corporation; James K. Blodgett

(57) ABSTRACT

Cyanine dye compounds having a substituted methine moiety that are nucleic acid stains, particularly for fluorescent staining of RNA, including compounds having the formula

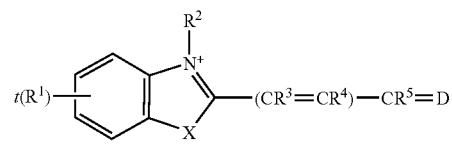

where $R^1$ is a $C_1$-$C_6$ alkyl, sulfoalkyl, carboxyalkyl or $C_1$-$C_6$ alkoxy; each $R^2$ is independently selected from the group consisting of H, $C_1$-$C_6$ alkyl, $C_1$-$C_6$ alkoxy, fused benzo, trifluoromethyl, amino, sulfo, carboxy and halogen, that is optionally further substituted; at least one of $R^3$, $R^4$, and $R^5$ is an alkyl, aryl, heteroaryl, cyclic, or heterocyclic moiety that is optionally substituted by alkyl, amino, aminoalkyl, carboxy, nitro, or halogen; and the remaining $R^3$, $R^4$ or $R^5$ are hydrogen; X is S, O, or Se; and D is a substituted or unsubstituted pyridinium, quinolinium or benzazolium moiety.

34 Claims, 5 Drawing Sheets

U.S. PATENT DOCUMENTS

| | | | |
|---|---|---|---|
| 4,945,171 A | 7/1990 | Haugland et al. | |
| 4,957,870 A | 9/1990 | Lee et al. | |
| 4,997,928 A | 3/1991 | Hobbs | |
| 5,041,366 A | 8/1991 | Asano et al. | |
| 5,047,519 A | 9/1991 | Hobbs et al. | |
| 5,049,673 A | 9/1991 | Tsien et al. | |
| 5,055,556 A | 10/1991 | Stryer et al. | |
| 5,057,413 A | 10/1991 | Terstappen et al. | |
| 5,122,602 A | 6/1992 | Corey et al. | |
| 5,132,432 A | 7/1992 | Haugland et al. | |
| 5,137,810 A | 8/1992 | Sizemore et al. | |
| 5,169,788 A | 12/1992 | Chen et al. | |
| 5,171,534 A | 12/1992 | Smith et al. | |
| 5,182,214 A | 1/1993 | Kessler et al. | |
| 5,187,288 A | 2/1993 | Kang et al. | |
| 5,208,148 A | 5/1993 | Haugland et al. | |
| 5,221,518 A | 6/1993 | Mills | |
| 5,227,487 A | 7/1993 | Haugland et al. | |
| 5,242,805 A | 9/1993 | Naleway et al. | |
| 5,248,782 A | 9/1993 | Haugland et al. | |
| 5,264,589 A | 11/1993 | Corey | |
| 5,268,486 A | 12/1993 | Waggoner et al. | |
| 5,274,113 A | 12/1993 | Kang et al. | |
| 5,279,790 A | 1/1994 | Corey et al. | |
| 5,314,805 A | 5/1994 | Haugland et al. | |
| 5,316,906 A | 5/1994 | Haugland et al. | |
| 5,321,130 A | 6/1994 | Yue et al. | |
| 5,326,692 A | 7/1994 | Brinkley | |
| 5,332,666 A | 7/1994 | Prober | |
| 5,352,803 A | 10/1994 | Mattingly | |
| 5,362,628 A | 11/1994 | Haugland et al. | |
| 5,375,606 A | 12/1994 | Slezak et al. | |
| 5,401,469 A | 3/1995 | Kobayashi et al. | |
| 5,401,847 A | 3/1995 | Glazer | |
| 5,405,975 A | 4/1995 | Kuhn | |
| 5,410,030 A | 4/1995 | Yue et al. | |
| 5,426,772 A | 6/1995 | Brady et al. | |
| 5,433,896 A | 7/1995 | Kang et al. | |
| 5,436,134 A | 7/1995 | Haugland et al. | |
| 5,437,980 A | 8/1995 | Haugland | |
| 5,442,045 A | 8/1995 | Haugland et al. | |
| 5,443,986 A | 8/1995 | Haughland et al. | |
| 5,445,946 A | 8/1995 | Roth | |
| 5,451,343 A | 9/1995 | Neckers et al. | |
| 5,453,517 A | 9/1995 | Kuhn et al. | |
| 5,459,268 A | 10/1995 | Haugland et al. | |
| 5,459,276 A | 10/1995 | Kuhn et al. | |
| 5,486,616 A | 1/1996 | Waggoner et al. | |
| 5,501,980 A | 3/1996 | Katerinopoulos et al. | |
| 5,534,416 A | 7/1996 | Millard et al. | |
| 5,545,535 A | 8/1996 | Roth et al. | |
| 5,564,554 A | 10/1996 | Lawrence | |
| 5,565,554 A | 10/1996 | Glazer et al. | |
| 5,569,587 A | 10/1996 | Waggoner | |
| 5,569,766 A | 10/1996 | Waggoner et al. | |
| 5,573,904 A | 11/1996 | Mattingly | |
| 5,573,909 A | 11/1996 | Singer et al. | |
| 5,578,439 A | 11/1996 | Inagaki et al. | |
| 5,582,977 A | 12/1996 | Yue et al. | |
| 5,597,696 A | 1/1997 | Linn et al. | |
| 5,616,502 A | 4/1997 | Haugland et al. | |
| 5,627,027 A | 5/1997 | Waggoner | |
| 5,648,270 A | 7/1997 | Kuhn et al. | |
| 5,656,449 A | 8/1997 | Yue | |
| 5,656,554 A | 8/1997 | Desai et al. | |
| 5,658,735 A | 8/1997 | Lee | |
| 5,658,751 A | 8/1997 | Yue et al. | |
| 5,691,145 A | 11/1997 | Pitner et al. | |
| 5,696,157 A | 12/1997 | Wang et al. | |
| 5,714,327 A | 2/1998 | Houthoff et al. | |
| 5,760,201 A | 6/1998 | Glazer | |
| 5,798,276 A | 8/1998 | Haugland et al. | |
| 5,800,996 A | 9/1998 | Lee et al. | |
| 5,830,912 A | 11/1998 | Gee et al. | |
| 5,846,737 A | 12/1998 | Kang | |
| 5,847,162 A | 12/1998 | Lee et al. | |
| 5,853,969 A | 12/1998 | Harada et al. | |
| 5,863,727 A | 1/1999 | Lee et al. | |
| 5,863,753 A | 1/1999 | Haugland et al. | |
| 5,869,689 A | 2/1999 | Zhang et al. | |
| 5,925,517 A | 7/1999 | Tyagi et al. | |
| 5,929,227 A | 7/1999 | Glazer et al. | |
| 5,945,526 A | 8/1999 | Lee et al. | |
| 5,963,753 A | 10/1999 | Ohtani et al. | |
| 6,004,536 A | 12/1999 | Leung et al. | |
| 6,008,373 A | 12/1999 | Waggoner et al. | |
| 6,008,379 A | 12/1999 | Benson et al. | |
| 6,017,712 A | 1/2000 | Lee et al. | |
| 6,025,505 A | 2/2000 | Lee et al. | |
| 6,027,709 A | 2/2000 | Little et al. | |
| 6,048,982 A | 4/2000 | Waggoner et al. | |
| 6,080,852 A | 6/2000 | Lee et al. | |
| 6,083,699 A | 7/2000 | Leushner et al. | |
| 6,103,476 A | 8/2000 | Tyagi et al. | |
| 6,114,350 A | 9/2000 | Randall et al. | |
| 6,130,101 A | 10/2000 | Mao et al. | |
| 6,140,494 A | 10/2000 | Hamilton et al. | |
| 6,146,831 A | 11/2000 | Davis et al. | |
| 6,153,370 A | 11/2000 | Maruyama et al. | |
| 6,162,931 A | 12/2000 | Gee et al. | |
| 6,184,379 B1 | 2/2001 | Josel et al. | |
| 6,197,956 B1 | 3/2001 | Randall et al. | |
| 6,200,752 B1 * | 3/2001 | Lakowicz | 435/6 |
| 6,204,389 B1 | 3/2001 | Randall et al. | |
| 6,221,606 B1 | 4/2001 | Benson et al. | |
| 6,224,644 B1 | 5/2001 | Randall et al. | |
| 6,225,050 B1 | 5/2001 | Waggoner | |
| 6,229,055 B1 | 5/2001 | Klaubert et al. | |
| 6,239,626 B1 | 5/2001 | Chesavage et al. | |
| 6,271,035 B1 | 8/2001 | Deka et al. | |
| 6,291,203 B1 | 9/2001 | Poot et al. | |
| 6,316,276 B1 | 11/2001 | Gregory | |
| 6,323,337 B1 | 11/2001 | Singer et al. | |
| 6,329,205 B1 | 12/2001 | Diwu et al. | |
| 6,339,392 B1 | 1/2002 | Ashihara et al. | |
| 6,342,389 B1 | 1/2002 | Cubicciotti | |
| 6,348,596 B1 | 2/2002 | Lee et al. | |
| 6,348,599 B1 | 2/2002 | Cummins et al. | |
| 6,358,684 B1 | 3/2002 | Lee | |
| 6,365,341 B1 * | 4/2002 | Wu et al. | 435/4 |
| 6,368,801 B1 * | 4/2002 | Faruqi | 435/6 |
| 6,372,445 B1 | 4/2002 | Davis et al. | |
| 6,399,392 B1 | 6/2002 | Haugland et al. | |
| 6,403,807 B1 | 6/2002 | Singh et al. | |
| 6,428,667 B1 | 8/2002 | Glazer et al. | |
| 6,453,425 B1 | 9/2002 | Hede et al. | |
| 6,541,205 B1 | 4/2003 | Yokoyama et al. | |
| 6,562,632 B1 | 5/2003 | Szalecki et al. | |
| 6,579,718 B1 | 6/2003 | Yue et al. | |
| 6,664,047 B1 | 12/2003 | Haugland et al. | |
| 6,716,979 B2 | 4/2004 | Diwu et al. | |
| 6,967,251 B2 | 11/2005 | Haugland et al. | |
| 6,972,326 B2 | 12/2005 | Haugland et al. | |
| 6,977,305 B2 | 12/2005 | Leung et al. | |
| 7,226,740 B2 | 6/2007 | Haugland et al. | |
| 7,271,265 B2 | 9/2007 | Haugland et al. | |
| 7,446,202 B2 | 11/2008 | Dallwig et al. | |
| 2002/0064794 A1 | 5/2002 | Leung et al. | |
| 2002/0077487 A1 | 6/2002 | Leung et al. | |
| 2005/0208534 A1 | 9/2005 | Dallwig et al. | |
| 2005/0214810 A1 | 9/2005 | Dallwig et al. | |
| 2005/0244976 A1 | 11/2005 | Gee et al. | |
| 2006/0004188 A1 | 1/2006 | Leung et al. | |
| 2006/0099638 A1 | 5/2006 | Leung et al. | |

| | | |
|---|---|---|
| 2006/0263844 A1 | 11/2006 | Bradford et al. |
| 2007/0178511 A1 | 8/2007 | Leung et al. |
| 2007/0178512 A1 | 8/2007 | Leung et al. |
| 2007/0232805 A1 | 10/2007 | Leung et al. |
| 2008/0039630 A1 | 2/2008 | Haugland et al. |
| 2008/0044811 A1 | 2/2008 | Haugland et al. |
| 2008/0199875 A1 | 8/2008 | Yue et al. |

FOREIGN PATENT DOCUMENTS

| | | |
|---|---|---|
| CA | 2133765 | 11/1999 |
| DE | 917330 | * 10/1955 |
| DE | 1923992 | 11/1970 |
| DE | 2135413 | 1/1972 |
| EP | 0410806 A1 | 1/1991 |
| EP | 0453197 A1 | 10/1991 |
| EP | 0492570 A1 | 7/1992 |
| EP | 0517050 A2 | 12/1992 |
| EP | 0517055 A1 | 12/1992 |
| EP | 0710668 A2 | 5/1996 |
| EP | 0714986 A1 | 6/1996 |
| EP | 0745690 | 12/1996 |
| EP | 0805376 | 11/1997 |
| EP | 870753 | 10/1998 |
| EP | 0882983 | 12/1998 |
| EP | 0985964 | 3/2000 |
| GB | 870753 | 7/1958 |
| GB | 1529202 | 10/1978 |
| GB | 2074340 | 10/1981 |
| JP | 02-084383 | 3/1990 |
| JP | 05-287209 | 11/1993 |
| JP | 06-123740 | 5/1994 |
| JP | 00-319260 | 11/2000 |
| JP | 09-218495 | 11/2001 |
| WO | WO-92/07867 A1 | 5/1992 |
| WO | WO-93/00633 | 1/1993 |
| WO | WO-93/04074 A1 | 3/1993 |
| WO | WO-93/04192 A1 | 3/1993 |
| WO | WO-93/06482 A1 | 4/1993 |
| WO | WO-93/11120 A1 | 6/1993 |
| WO | WO-94/05688 | 3/1994 |
| WO | WO-94/24213 A1 | 10/1994 |
| WO | WO-96/13552 | 5/1996 |
| WO | WO-96/36882 A1 | 11/1996 |
| WO | WO-97/12508 | 4/1997 |
| WO | WO-97/17076 | 5/1997 |
| WO | WO-97/39064 | 10/1997 |
| WO | WO-97/45539 | 12/1997 |
| WO | WO-98/17826 A1 | 4/1998 |
| WO | WO-99/37717 | 7/1999 |
| WO | WO-99/64519 A1 | 12/1999 |
| WO | WO-00/6664 | 11/2000 |
| WO | WO 00/66664 A | 11/2000 |
| WO | WO-01/86264 | 11/2001 |
| WO | WO-2005/056687 A2 | 6/2005 |
| WO | WO-2006/124816 A1 | 11/2006 |

OTHER PUBLICATIONS

STN International, CAPLUS Database, Accession No. 1959:5447, Reg. No. 109724-08-5 (2006).*
PCT/US2004/040886 International Search Report dated Aug. 18, 2005.
U.S. Appl. No. 09/557,275, Notice of Allowance, Jun. 4, 2003.
U.S. Appl. No. 09/557,275, Office Action mailed Nov. 20, 2002.
U.S. Appl. No. 09/557,275, Response to Nov. 20, 2002 Office Action, Filed Mar. 13, 2003.
U.S. Appl. No. 09/557,275, Response to Rest. Req., Filed Aug. 21, 2002.
U.S. Appl. No. 09/557,275, Restriction Req. mailed Jul. 22, 2000.
U.S. Appl. No. 09/557,275, Supp. Resp. to Rest. Req., Filed Oct. 16, 2002.
U.S. Appl. No. 10/683,753, Notice of Allowance mailed Jan. 29, 2007.
U.S. Appl. No. 10/683,753, Office Action mailed Jun. 9, 2006.
U.S. Appl. No. 10/683,753, Office Action mailed Oct. 2, 2006.
U.S. Appl. No. 10/683,753, Response to Jun. 9, 2006 Office Action, Filed Sep. 11, 2006.
U.S. Appl. No. 10/683,753, Response to Oct. 2, 2006 Office Action, Filed Jan. 3, 2007.
U.S. Appl. No. 10/683,753, Response to Rest. Req., Filed Apr. 27, 2006.
U.S. Appl. No. 10/683,753, Restriction Req. mailed Apr. 29, 2006.
U.S. Appl. No. 10/911,423, Office Action mailed Sep. 17, 2007.
U.S. Appl. No. 10/911,423, Office Action mailed Dec. 21, 2007.
U.S. Appl. No. 10/911,423, Response to Sep. 17, 2007 Office Action, Filed Oct. 17, 2007.
U.S. Appl. No. 10/911,423, Response to Rest. Req., Filed Jul. 9, 2007.
U.S. Appl. No. 10/911,423, Restriction Req. mailed Jun. 8, 2007.
U.S. Appl. No. 10/916,822, Advisory Action mailed Aug. 29, 2006.
U.S. Appl. No. 10/916,822, Notice of Allowance, May 11, 2007.
U.S. Appl. No. 10/916,822, Office Action mailed Jun. 13, 2006.
U.S. Appl. No. 10/916,822, Office Action mailed Nov. 30, 2006.
U.S. Appl. No. 10/916,822, Office Action mailed Dec. 9, 2005.
U.S. Appl. No. 10/916,822, Response to Jun. 13, 2006 Office Action, Filed Aug. 14, 2006.
U.S. Appl. No. 10/916,822, Response to Aug. 29, 2006 Advisory Action, Filed Sep. 13, 2006.
U.S. Appl. No. 10/916,822, Response to Nov. 30, 2006 Office Action, Filed Feb. 27, 2007.
U.S. Appl. No. 10/916,822, Supp. Response to Nov. 30, 2006 Office Action, Filed May 7, 2007.
U.S. Appl. No. 11/005,860, Notice of Allowance mailed Jun. 30, 2008.
U.S. Appl. No. 11/005,860, Office Action mailed Dec. 28, 2007.
U.S. Appl. No. 11/005,860, Response to Dec. 28, 2007 Office Action, Filed Mar. 28, 2008.
U.S. Appl. No. 11/005,860, Response to Rest. Req., Filed Oct. 12, 2007.
U.S. Appl. No. 11/005,860, Restriction Req. mailed Sep. 12, 2007.
U.S. Appl. No. 11/063,707, Advisory Action mailed Jan. 19, 2007.
U.S. Appl. No. 11/063,707, Office Action mailed Apr. 30, 2007.
U.S. Appl. No. 11/063,707, Office Action mailed Jun. 1, 2006.
U.S. Appl. No. 11/063,707, Office Action mailed Oct. 12, 2006.
U.S. Appl. No. 11/063,707, Response Oct. 12, 2006 Office Action, Filed Dec. 8, 2006.
U.S. Appl. No. 11/063,707, Response to Jan. 19, 2007 Advisory Action, Filed Feb. 12, 2007.
U.S. Appl. No. 11/063,707, Response to Jun. 1, 2006 Office Action, Filed Oct. 2, 2006.
U.S. Appl. No. 11/063,707, Response to Rest. Req., Filed Mar. 27, 2006.
U.S. Appl. No. 11/063,707, Restriction Req. mailed Mar. 13, 2006.
U.S. Appl. No. 11/432,814, Notice of Allowance, Oct. 27, 2008.
U.S. Appl. No. 11/432,814, Office Action mailed Mar. 27, 2008.
U.S. Appl. No. 11/432,814, Response to Mar. 27, 2008 Office Action, Filed Aug. 26, 2008.
U.S. Appl. No. 11/756,765, Office Action mailed Apr. 2, 2008.
U.S. Appl. No. 11/756,765, Response to Apr. 2, 2008 Office Action, Filed Oct. 2, 2008.
Abramo, K. H. et al., "Spectroscopic Studies of Single-Stranded DNA Ligands and Oxazole Yellow Dyes", *Biospectroscopy*; 4(1), 1998, 27-35.
Allan, R. A. et al., "Influence of S-adenosylmethionine on DAPI-induced fluorescence of polyphosphate in the yeast vacuole", *Canadian Journal of Microbiology*, vol. 26, National Research Council of Canada, Apr. 22, 1980, 912-920.
Allmann, et al., "Konformationsanalyse von Polymethinen I, Erstmaliger Nachweis von di-, tri- und all-cis-Konformationen bei sterisch gehinderten Trimethincyaninen (Carbocyaninen) der Indolin- und Benzothiazolreihe", *Angew. Chem. Suppl.*, 1983, 1147-1175.
Ausubel, F. M. et al., "Short Protocols in Molecular Biology", *John Wiley & Sons*, 2002, 359.
Barlin, G. B. et al., "Purine Analogues as Amplifiers of Phleomycin. IX Some 2- and 6-Substituted Thiazolo [4,5,-b] Pyrazines, 2-Substituted Thiazolo[4,5,-c]-and Thiazolo[5,4,-b]-Pyrazines and Related Compounds", *Aust. J. Chem.*, vol. 37, 1984, 1729-1737.

Barlin, G. B. et al., "Purine Analogues as Amplifiers of Phleomycin. VIII Some Thiazolo[4,5-g] pyrazines and Related Compounds", *Aust. J. Chem.*, vol. 36, 1983, 983-985.

Barni, E. et al., "Synthesis, Surface Activity and Micelle Formation of Novel Cyanine Dyes", *Helvetica Chimica Acta*, vol. 64, No. 6, 1981, 1943-1948.

Bartnik, R. et al., "Synthesis of New Trimethinecyanine Dyes by Condensation of 2-Formylmethylene-3,3-Dimethylindoline with 2-Cyanomethylbenzimidazoles", *Polish Journal of Applied Chemistry*, vol. 37, No. 1-2, 1993, 119-125.

Beebe, K. D. et al., "A continuous fluorimetric assay for tail-specific protease", Analytical Biochemistry, vol. 263, No. 1, 1998, 51-56.

Beekman, B. et al., "Convenient fluorometric assay for matrix metalloproteinase activity and its application in biological media", *FEBS Lett*, 390(2), 1996, 221-5.

Beekman, B et al., "Highly increased levels of active stromelysin in rheumatoid synovial fluid determined by a selective fluorogenic assay", *FEBS Lett*, 418(3), 1997, 305-9.

Bensimon, A. et al., "Alignment and Sensitive Detection of DNA by a Moving Interface", *Science 265*, 1994, 2096-2098.

Berge, et al., "Pharmaceutical Salts", *Journal of Pharmaceutical Sciences*, 66 1977, 1-19.

Bolton, P. H. et al., "Spectroscopic properties of ethidium monoazide: a fluorescent photoaffinity label for nucleic acids", *Nucleic Acids Research*, vol. 5, 1978, 4891-4904.

Bouizar, Z. et al., "Purification and Characterization of Calcitonin Receptors in Rat Kidney Membranes by Covalent Cross-Linking Techniques", *Eur J Biochem*, 155(1), 1986, 141-7.

Bradford, M. M., "A Rapid and Sensitive Method for the Quantitation of Microgram Quantities of Protein Utilizing the Principle of Protein-Dye Binding", *Analytical Biochemistry*, vol. 72, No. 2, 1976, 248-254.

Brinkley, M., "A Brief Survey of Methods for Preparing Protein Conjugates with Dyes, Haptens, and Cross-Linking Reagents", *Bioconjugate Chem*, vol. 3, No. 1, 1992, 2-13.

Brooker, L. G. S. et al., *J. Am. Chem. Soc.* vol. 73 1951, 5350-5356.

Brooker, L G. et al., "Color and Constitution. V. The absorption of unsymmetrical cyanines. Resonance as a basis for a classification of dyes", *Journal of the American Chemical Society*, vol. 64, Communication No. 833 From the Kodak Research Laboratories, Feb. 1942, 199-210.

Brooker, L.G.S. et al., "Color and constitution. X. Absorption of the Merocyanines", *Journal of the American Chemical Society*, vol. 73, Communication No. 1397 from the Kodak Research Laboratories, 1951, 5332-5350.

Brooker, et al., "Studies in the Cyanine Dye Series. XI. The Merocyanines", *Journal of the American Chemical Society*, vol. 73, 1951, 5326-5332.

Browning, Jeffrey et al., "Studies on the Differing Effects of the Tumor Necrosis Factor and Lymphotoxin on the Growth of Several Human Tumor Lines", *The Journal of Immunology*, vol. 143, No. 6, Sep. 15, 1989, 1859-1867.

Buehler, R. et al., "Charge Translocation by the Sodium, Potassium pump: I. Kinetics of Local Field Changes Studied by Time-Resolved Fluorescence Measurements", *Chemical Abstracts*, 115 (9), 1991, 3 pages.

Buhler, R. et al., "Charge Translocation by the Na, K-Pump: I. Kinetics of Local Field Changes Studied by Time-Resolved Fluorescence Measurements", *Journal of Membrane Biology*, vol. 121, No. 2, Apr. 1991, 141-161.

Bunkenborg, J. et al., "Concerted intercalation and minor groove recognition of DNA by a homodimeric thiazole orange dye", *Bioconjugate Chemistry*, vol. 11, No. 6, Nov. 2000, 861-867.

Carlsson, et al., "Optical and Photophysical Properties of the Oxazole Yellow DNA Probes YO and YOYO", (Abstract only) *Journal of Physical Chemistry*, 98(40), 10313-21, STN Accession No. 1994: 650470, 1994, 2 pgs.

Castro, A. et al., "Fluorescence Detection and Size Measurement of Single DNA Molecules", *Anal. Chem.*, 65:7, 1993, 849-852.

Chu-Moyer, M. Y. et al., "Preparation of the Four Regioisomeric 2-(Methylthio)oxazolopyridines: Useful Synthons for Elaboration to 2-(Amino substituted)oxazolopyridines", *Journal of Organic Chemistry*, vol. 60, No. 17, 1995, 5721-5725.

Ci, Yun-Xiang et al., "Fluorimetric Determination of Human Serum Albumin with Eriochrome Cyanine R", *Analyst*, vol. 113, Apr. 1988, 679-681.

Clark, L. M. et al., "Reactivity of the Imino-group in 1-Imino-2-methylbenzthiazoline", *Journal of the Chemical Society*; Notes, 1936, 507.

Cohen, R L. et al., "A cyanine dye distinguishes between cycling and non-cycling fibroblasts", *Nature*, vol. 290, Apr. 16, 1981, 593-595.

Coppieters, K., "A Cross-Platform Binary Diff", *Dr. Dobb's Journal*, vol. 32, http://www.ddj.com/architect/184409550, May 1, 1995, 35-36.

Couture, A. et al., "2-Aryl-Oxazolo- and Thiazolopyridines. Synthesis via Cyclization of N-(2 Chloro-3-Pyridinyl) Arylamides and Thioamides", Heterocycles, vol. 22, No. 6, 1984, 1383-1385.

Czikkely, V et al., "Lichtabsorption von Farbstoff-Molekulpaaren in Sandwichsystemen aus monomolekularen Schichten", *Zeitschrift für Naturforschung*, vol. 242, No. 11, 1969, 1821.

Daban, J. et al., "Use of the hydrophobic probe Nile red for the fluorescent staining of protein bands in sodium dodecyl sulfate-polyacrylamide gels", *Analytical Biochemistry*, vol. 199, No. 2, 1991, 169-174.

Davis, B. H. et al., "Clinical Flow Cytometric Reticulocyte Analysis", *Diagnostic Flow Cytometry*, Chapter 8, 1990, 103-113.

Dean, P. D. G. et al., "Affinity Chromatography: A Practical Approach", *IRl Press*, 1985, 34-35.

Diwu, Z. et al., "Novel Site-Selective Fluorescent Probes for Lysosome and Acidic Organelle Staining and Long-Term Tracking", *International Society for Analytical Cytology*, Cytometry supp. 7; Abstract# 426B, 1994, 77.

Dos Remedios, C. G. et al., "Fluorescence Resonance Energy Transfer Spectroscopy is a Reliable 'Ruler' for Measuring Structural Changes in Proteins. Dispelling the Problem with the Unknown Orientation Factor", *J Struct Biol*, 115(2), 1995, 175-85.

EP 94914173, Examination Report mailed Jul. 6, 1999.

EP 94914173, Examination Report mailed May 16, 2000.

EP 95937613, Examination Report mailed Oct. 21, 1999.

EP 96920325, Examination Report mailed Mar. 24, 2003.

EP 96920325, Examination Report mailed Mar. 30, 2000.

EP 96920325, Examination Report mailed May 30, 2006.

EP 96920325, Examination Report mailed Sep. 14, 2001.

Ficken, G. E. et al., "Diazaindenes and Their Quaternary Salts. Part 1. The preparation of 2,3,3-Trimethyl-3H-1,7-diazaindene, and its Methiodides and Derived Cyanine Dyes.", *J. Chem. Soc*, 1959, 3202-3212.

Ficken, et al., "Diazaines and Their Quarternary Salts. Part II. The Cyclisation of Isopropyl Methyl Ketone 3-Pyridylhydrazone.", CA 55:70677, *J of Chem Soc*, 1961, 584-588.

Figeys, et al., "Use of the fluorescent intercalating dyes POPO-3, YOYO-3, and YOYO-1 for ultrasensitive detection of double-stranded DNA separated by capillary electrophoresis with hydroxypropylmethyl cellulose and non-crosslinked polyacrylamide", *Journal of Chromatography*, A, STN Accession Number: 1994:453324, 1994, 205-16.

Foye, W. O. et al., "Antiradiation compounds XV: Condensations of carbon disulfide with amino, chloro, cyanomethyl, and sulfonamido heterocycles", *J. Pharm. Sci.*, vol. 64, No. 8, Aug. 1975, 1371-1374.

Furniss, B. S. et al., *Vogel's Textbook of Practical Organic Chemistry*, Fifth Ed, Longman Group UK Ltd., Essex, 1989, 809-23.

Gadjev, N. I. et al., "Synthesis and properties of YOYO-1-type homodimeric monomethine cyanine dyes as noncovalent nucleic acid labels", *Dyes and Pigments*, vol. 57(2), 2003, 161-164.

Gadjev, N. I. et al., "Preparation of monomethine cyanine dyes as noncovalent labels for nucleic acids", Dyes and Pigments, vol. 40(2-3), 1999, 181-186.

Gaffney, D. K. et al., "The Role of Serum and Serum Components in the Merocyanine 540-Sensitized Photoinactivation of K562 Leukemia Cells", *Chemical Abstracts*, vol. 117, No. 25, Dec. 21, 1992.

Gaffney, David K. et al., "The Role of Serum and Serum Components in the Merocyanine 540-Sensitized Photoinactivation of K562 Leukemia Cells", *Biochimica et Biophysica Acta*, vol. 1117, Issue 3, Feb. 24, 1992, 321-325.

Gaugain, B. et al., "DNA Bifunctional Intercalators. 2. Fluorescence Properties and DNA Binding Interaction of an Ethidium Homodimer and an Acridine Ethidium Heterodimer", *Biochemistry*, vol. 17, No. 24, 1978, 5078-5088.

Gaugain, B. et al., "DNA bifunctional intercalators. I. Synthesis and conformational properties of an ethidium homodimer and an acridine ethidium heterodimer", *Biochemistry*, 17(24), 1978, 5071-5078.

Gemahlich, M. et al., "Electrophoretic Studies of Fluorochrome-treated Serum and Organ Proteins", *Chemical Abstracts*, 54 (20), Oct. 25, 1960, 21215-21216.

Georgi, A. et al., "Detection of Individual Fluorescently Labeled Reovirions in Living Cells", *Proceedings of the National Academy of Sciences (PNAS)*, vol. 87, 1990, 6579-6583.

Goodwin, P. M. et al., "Rapid sizing of individual fluorescently stained DNA fragments by flow cytometry", *Nucleic Acids Research*, 21(4), 1993, 803-806.

Govorunov, I. G. et al., "Study of Permeability of *Escherichia coli* Membrane to Ethidium Bromide", *Plenum Publishing Corp.*, 1983, 587-589.

Griffiths, J., "Colour and Constitution of Organic Molecules", *Academic Press*, 1976, 241-251.

Grinvald, A. et al., "Improved fluorescent probes for the measurement of rapid changes in membrane potential", *Biophys J.*, vol. 39, 1982, 301-308.

Hahn, K. M. et al., "A Calcium-sensitive Fluorescent Analog of Calmodulin Based on a Novel Calmodulin-binding Fluorophore", *The Journal of Biological Chemistry*, vol. 265, No. 33, 1990, 20335-20345.

Hamer, F. M., "Bases of which Methincyanines are the Quaternary Salts", *The Journal of the Chemistry Society*, 1940, 799-808.

Hamer, Frances M., "The Cyanine Dyes and Related Compounds", *The Chemistry of Heterocyclic Compounds*, vol. 18, (Table of Contents), A. Weissberger, Ed., Interscience, 1964, 1-34.

Hassner, A. et al., "Charge-Shift Probes of Membrane Potential. Synthesis", *J. Org. Chem.* 49(14), 1984, 2546-2551.

Haugland, Rosaria P., "Ch 22: Coupling of monoclonal antibodies with fluorophores", *Methods in Molecular Biology*, vol. 45, 1995, 205-221.

Haugland, Richard P., "Chapters 1-3", *Molecular Probes Handbook of Fluorescent Probes and Research Chemicals*, Molecular Probes, Inc/Invitrogen, 1996.

Haugland, Rosaria P. et al., "Coupling of Antibodies with Biotin", *Humana Press*, vol. 418, 1996, 13-23.

Haugland, Rosaria P. et al., "Coupling of Antibodies with Biotin", *The Protein Protocols Handbook*, Humana Press, 1996, 293.

Haugland, Rosaria P. et al., "Coupling of monoclonal antibodies with biotin", *Methods in Molecular Biology*, vol. 45, 1995, 223-233.

Haugland, Richard P., "Handbook of Fluorescent Probes and Research Chemicals", Sets 1-7, Molecular Probes, Inc./Invitrogen, 1992.

Haugland, Richard P., "Molecular Probes Handbook of Fluorescent Probes and Research Chemicals", 6th Edition (Subsequent 7th and 8th edition updates issued on CD Rom. 1996), (Table of Contents), 15.

Haugland, Richard P., "Molecular Probes Handbook of Fluorescent Probes and Research Chemicals", 9th Edition, (Table of Contents), 2002, 6.

Haugland, Richard P., "Set 28: Nuclear Stains", *Molecular Probes Handbook of Fluorescent Probes and Research Chemicals*, Molecular Probes, Inc./Invitrogen, 1989, 129-130.

Haugland, Richard P., "Sets 25 & 31", *Handbook of Fluorescent Probes and Research Chemicals*, Molecular Probes, Inc./Invitrogen, 1992, 172-180, 221-230.

Heller, A., "Electrical Wiring of Redox Enzymes", *Acc. Chem. Res*, vol. 23, No. 5, 1990, 128-134.

Heravi, M. M. et al., "Heterocyclic monoazo dyes derived from 2-(p-aminophenyl)oxazolo-[4,5-b]pyridine and 7-(p-aminophenyl)-4H[1,3,4]thiadiazolo-[2,3-c][1,2,4]triazin-4-one", *Indian J. Chem.*, vol. 36B, 1997, 1025-1029.

Hickman, D. T. et al., "Kinetically selective binding of single stranded RNA over DNA by a pyrrolidine-amide oligonucleotide mimic (POM)", *Nucleosides Nucleotides & Nucleic Acids*, vol. 20, No. 4-7, 2001, 1169-1172.

Holskin, B. P. et al., "A continuous fluorescence-based assay of human cytomegalovirus protease using a peptide substrate", *Analytical Biochemistry*, vol. 226, No. 1, 1995, 148-55.

Hongyo, T. et al., "'Cold SSCP': a simple, rapid, and non-radioactive method for optimized single-strand conformation polymorphism analyses", *Nucleic Acids Research*, 21(16), 1993, 3637-3642.

Honig, M. G. et al., "Fluorescent carbocyanine dyes allow living neurons of identified origin to be studied in long-term cultures", *The Journal of Cell Biology*, vol. 103, No. 1, Jul. 1, 1986, 171-187.

Ishiguro, T. et al., "Fluorescence detection of specific sequence of nucleic acids by oxazole yellow-linked oligonucleotides. Homogeneous quantitative monitoring of in vitro transcription", *Nucleic Acids Research*, vol. 24, No. 24, 1996, 4992-4997.

Izmail'Skii, V. A. et al., "Exomolecular interaction and color. VIII. Absorption spectra of molecular complexes of 9-(p-Dimethylaminostyryl)-acridine with 10-alkyl-9-methylacridinium salts", *Journal of General Chemistry of the USSR*, vol. 29, Jun. 9, 1958, 1813-1819.

Jensen, O. N. et al., "Mass Spectrometric Identification and Microcharacterization of Proteins from Electrophoretic Gels: Strategies and Applications", *Proteins: Structure, Function, and Genetics Suppl.*, 2, 1998, 74-89.

Johnson, I. D. et al., "Asymmetric Cyanine Dyes for Fluorescent Staining and Quantification of Nucleic Acids", *Biophysical Society/ASBMB Joint Meeting*, Poster # 1806, 1992.

Joshi, S. et al., "ATP Synthase complex from Bovine Heart Mitochondria. Subunit Arrangements as Revealed by Nearest Neighbor Analysis and Susceptibilty to Trypsin", *J Biol Chem*, 265(24), 1990, 14518-14525.

Jung, S. M. et al., "Crosslinking of Platelet Glycoprotein lb by N-Succinimidyl (4-azidophenyldithio) Propionate and 3, 3'-dithiobis (Sulfosuccinimidyl Propionate)", *Biochim Biophys Acta*, 761(2), 1983, 152-62.

Kaneshiro, E. S. et al., "Reliability of Calcein Acetoxy Methyl Ester and Ethidium Homodimer or Propidium Iodide for Viability Assessment Microbes", *Journal of Microbiological Methods*, 17, 1993, 1-16.

Karlsson, H. J. et al., "Groove-binding unsymmetrical cyanine dyes for staining of DNA: syntheses and characterization of the DNA-binding", *Nucleic Acids Res.*, 31(21), 2003, 6227-6234.

Kaufmann, Hitto et al., "Use of Antibodies for Detection of Phosphorylated Proteins Separated by Two-Dimensional Gel Electrophoresis", *Proteomics*, vol. 1, No. 2, 2001, 194-199.

Khanna, Ish K. et al., "Facile, Regioselective Synthesis of N-Alkylated 2,3-Diaminopyridines and Imidazo[4,5-b]pyridines", *J. Org. Chem.*, vol. 60, 1995, 960-965.

Kudinova, M A. et al., "Pyrylocyanines 12. Unsymmetrical pyrylo-2-cyanines", *Chemical Abstracts*, vol. 93, No. 25, Abstract# 241180j, 1980, 91.

Kudinova, M A. et al., "Pyrylocyanines. 12. Unsymmetrical pyrylo-2-cyanines", *Chemistry of Heterocyclic Compounds*, vol. 16, No. 7, Translated from Khimiya Geterotsiklicheskikh Soedinenii, No. 7, Jul. 1980, 696-701.

Lee, Linda G. et al., "Thiazole Orange: A New Dye for Reticulocyte Analysis", *Cytometry*, 7, 1986, 508-517.

Lowry, Oliver H. et al., "Protein Measurement with the Folin Phenol Reagent", *The Journal of Biological Chemistry*, vol. 193, No. 1, 1951, 265-275.

Makin, S M. et al., "Synthesis and Investigation of Tricarbocynanines Containing Five-and-Six Membered Rings in the Chromophore", *Journal of Organic Chemistry*, vol. 13, No. 11, (Translated from original Zhurnal Organicheskoi Khimii article), pp. 2440-2443, Nov. 1977, 2269-2271.

Malone, James P. et al., "Practical aspects of fluorescent staining for proteomic applications", *Electrophoresis*, vol. 22, No. 5, 2001, 919-32.

Markovits, et al., "Dynamic Structure of DNA Complexes. Fluorometric Measurement of Hydrogen-Deuterium Exchange Kinetics of DNA-bound Ethidium Dimer and Acridine-Ethidium Dimer", *Biochemistry*, 22(13), 1983, 3231-3237.

Markovits, Judith et al., "Effect of B-Z transition and nucleic add structure on the conformational dynamics of bound ethidium dimer measured by hydrogen deuterium exchange kinetics", *Nucl. Acids Res.*, 13, 1985, 3773-3788.

Markovits, et al., "Ethidium Dimer: A New Reagent for the Fluorimetric Determination of Nucleic Acids", *Analytical Biochemistry*, vol. 94, 1979, 259-269.
Marson, Charles M., "Reactions of Carbonyl Compounds with (Monohalo) Methyleniminium Salts (Vilsmeier Reagents)", *Tetrahedron*, vol. 48, No. 18, Report No. 312, 1992, 3659-3726.
Matayoshi, E. D. et al., "Novel Fluorogenic Substrates for Assaying Retroviral Proteases by Resonance Energy Transfer", *Science*, 247(4945), 1990, 954-8.
Matselyukh, et al., "Interaction of cyanine dyes with nucleic acids: XXXI. using of polymethine cyanine dyes for the visualisation of DNA in agarose gels", *Journal of Biochemical and Biophysical Methods*, (Abstract only), vol. 57(1), STN Accession No. 2003:499067, 2003, 35-43.
Matsuyama, Tohey, "Staining of Living Bacteria with Rhodamine 123", *FEMS Microbiology Letters*, 21, 1984, 153-157.
McRae, E G. et al., "The molecular exciton model", *Chemical Abstracts*, vol. 63, No. 3, Aug. 1965, 2525.
Morrison, L. E., "Detection of Energy Transfer and Flourescence Quenching", *Nonisotopic DNA Probe Techniques*, L. Kricka, ed., 1992, 311-352.
Mushkalo, I L. et al., "3,3'-Ethylenebis(benzothiazolium) salts and their biscyanine dyes", *Chemical Abstracts*, vol. 88, No. 4, Abstract# 38936q, 1978, 57.
Noueiry, Amine O. et al., "Two Proteins of a Plant DNA Virus Coordinate Nuclear and Plasmodesmal Transport", *Cell*, 76, 1994, 925-932.
Park, Linda S. et al., "Characterization of the Cell Surface Receptor for a Multi-Lineage Colony-Stimulating Factor (CSF-2alpha)", *The Journal of Biological Chemistry*, vol. 261, No. 1, 1986, 205-210.
Pennington, M. W. et al., "Synthesis of fluorogenic interleukin-1 beta converting enzyme substrate based on resonance energy transfer", *Pep. Res*, 7:2, 1994, 72-76.
Perkins, Thomas T. et al., "Direct Observation of Tube-Like Motion of a Single Polymer Chain", *Science*, 264, 1994, 819-822.
Perkins, Thomas T. et al., "Relaxation of a Single DNA Molecule Observed by Optical Microscopy", *Science*, 264, 1994, 822-825.
Petric, A et al., "Azido-Tetrazolo Isomerizations of Some Thiazolopyridines (1)", *J. Heterocyclin Chem.*, vol. 14, Oct. 1977, 1045-1047.
Przhiyalgovskaya, N. M. et al., "Carbocyanine Dyes with an O-hydroxyaryl Substituent in the Meso Position of the Polymethine Chain", *Platinum Publishing Corp.*, 24 (1), 1988, 83-86.
Rago, Randall et al., "DNA Fluorometric Assay in 96-Well Tissue Culture Plates Using Hoechst 33258 after Cell Lysis by Freezing in Distilled Water", *Analytical Biochemistry*, vol. 191, No. 31, 1990, 31-34.
Raju, B. et al., "A fluorescent indicator for measuring cytosolic free magnesium", *Am. J. Physiol.*, vol. 256, 1989, C540-C548.
Rye, et al., *Chem. Abstracts*, 117(13), 1992, 127607t.
Rye, Hays S. et al., "High-Sensitivity Two-Color Detection of Double-Stranded DNA With a Confocal Fluorescence Gel Scanner using Ethidium Homodimer and Thiazole Orange", *Nucleic Acids Research*, vol. 19, No. 2, 1990, 327-333.
Rye, Hays S. et al., "Stable Fluorescent Complexes of Double-Stranded DNA With Bis-Intercalating Asymmetric Cyanine Dyes: Properties and Applications", *Nucleic Acids Research*, vol. 20, No. 11, Oxford University Press, 1992, 2803-2812.
Saikachi, Haruo et al., "Studies on Compounds Related to Pyrazine. III. Synthesis of 2-Substituted Thiazolo[b]quinozaline.", *Chem. & Pharm. Bull.*, vol. 9, No. 12, Dec. 1961, 941-944.
Saitoh, Yasushi et al., "Metaphase Chromosome Structure: Bands Arise from a Differential Folding Path of the Highly AT-Rich Scaffold", *Cell*, 76, 1994, 609-622.
Sandler, Stanley R. et al., "Organic Functional Group Preparations", *Academic Press*, vol. 3, 1972, 5-7.
Schlessinger, J et al., "Lateral transport of a lipid probe and labeled proteins on a cell membrane", *Science*, vol. 195, Jan. 1977, 307-309.
Schobel, et al., "New Donor-Acceptor Pair for Fluorescent Immunoassays by Energy Transfer", *Bioconjugate Chem.*, 10, 1999, 1107-1114.
Selvin, Paul R., "Flouresence Resonance Energy Transfer", *Methods in Enzymology*, vol. 246, Academic Press Inc., 1995, 300-34.

Shevchenko, A. et al., "Mass Spectrometric Sequencing of Proteins Silver-Stained Polyacrylamide Gels", *Anal Chem*, 68(5), 1996, 850-8.
Simbera, J. et al., "Synthesis of polymethine dyes from 1-(3-chloro-2-tetrahydrofuryl)-4methylquinolinium chloride", *Chemical Abstracts*, vol. 89, No. 13, Abstract # 112299y, 1978, 151.
Singh, T. et al., "Antimalaria. Distal Hydrazine derivatives of 7-chloroquinoline", *J Med Chem*, 14(6), 1971, 532-5.
Sizemore, Ronald K. et al., "Alternate Gram Staining Technique Using a Fluorescent Lectin", *Applied and Environmental Microbiology*, vol. 56, No. 7, Jul. 1990, 2245-2247.
Sizemore, Christine et al., "Quantitative analysis of Tn10 Tet repressor binding to a complete set of tet operator mutants", *Nucleic Acids Research*; vol. 18, No. 10, Oxford University Press, 1990, 2875-2880.
Smith, Keith et al., "A Convenient Synthesis of 2-Substituted Thiazolo [4,5-b]pyridines via Directed Metalation", *Sulfur Letters*, vol. 18, No. 2, 1995, 79-95.
Smith, Keith et al., "Convenient synthesis of 4-aminopyridine-3-thiol and several thiazolo[5,4-c]pyridines via direct ligation", *Chemistry and Industry*, vol. 9, May 2, 1988, 302-303.
Smith, P. K. et al., "Measurement of Protein Using Bicinchoninic Acid", *Analytical Biochemistry*, vol. 150, 1985, 76-85.
Smith, J. C., "Potential-sensitive molecular probes in membranes of bioenergetic relevance", *Chemical Abstracts*, vol. 112, No. 19, Abstract# 174955m, 1990, 369.
Smith, J. C., "Potential-sensitive molecular probes in membranes of bioenergetic relevance", *Biochimica et Niophysica Acta*, vol. 1016, No. 1, Mar. 15, 1990, 1-28.
Smith, Keith et al., "The synthesis of 2-substituted thiazolo[5,4-c]pyridines via directed methalation", *Sulfur Letters*, vol. 17, No. 4, 1994, 197-216.
Spatola, A F., "Peptide Backbone Modifications: A Structure—Activity Analysis of Peptides Containing Amide Bond Surrogates . . . ", *Chemistry and Biochemistry of Amino Acids, Peptides and Proteins*, 1983, 267-357.
Staerk, D. et al., "Bisintercalation of homodimeric thiazole orange dyes in DNA: Effect of modifying the linker", *Bioconjugate Chemistry*, vol. 8, No. 6, Nov. 1997, 869-877.
Steinberg, Thomas H. et al., "Global Quantitative Phosphoprotein Analysis Using Multiplexed Proteomics Technology", *Proteomics*, vol. 3, Jul. 2003, 1128-1144.
Steinberg, T. H. et al., "Rapid and Simple Single Nanogram Detection of Glycoproteins in Polycralamide Gels and on Electroblots", *Proteomics*, 1(7): 2001, 841-55.
Stetsenko, A. V., "Benzimidocyanines", *Ukrainskii khimicheskii zhurnal*, (Ukrainian Chemistry Journal), vol. 43, No. 1, Jan. 1977, 57-61.
Stevens, Anthony C. et al., "Synthesis of Protein-Reactive (Aminostyryl) pyridinium dyes", *Bioconjugate Chemistry*, vol. 4, 1993, 19-24.
Stezenko, A V. et al., "Cyanine Dyes, Derivatives", *Ukrainskii khimicheskii zhurnal*, (Ukrainian Chemistry Journal), vol. 27, 1961, 237-240.
Stratagene Catalog, Gene Characterization Kits, 1988, 39.
Strickland, R D. et al., "Dye-Binding Capacities of Eleven Electrophoretically Separated Serum Proteins", *Analytical Chemistry*, vol. 31, No. 8, Aug. 1959, 1408-1410.
Tijssen, J P. et al., "Localization of Polyphosphates in Saccharomyces Fragilis, as Revealed by 4', 6-Diamidino-2-Phenylindole Fluorescence", *Biochimica et Biophysica Acta*, vol. 721, Elsevier Biomedical Press, 1982, 394-398.
Timtcheva, I. et al., "Homodimeric monomethine cyanine dyes as fluorescent probes of biopolymers", *Journal of Photochemistry and Photobiology B Biology*, 58(2-3), Nov. 2000, 130-135.
Turner, James A., "Regiospecific electrophilic substitution of aminopyridines: ortho lithiation of 2-, 3-, and 4-(pivaloylamino)pyridines", *Journal of Organic Chemistry*, vol. 48, 1983, 3401-3408.
Tyagi, Sanjay et al., "Molecular Beacons: probes that fluorescence upon hybridization", *Nature Biotechnology*, vol. 14, No. 3, Mar. 1996, 303-308.

Tyagi, Sanjay et al., "Multicolor molecular beacons for allele discrimination", *Nature Biotechnology*, vol. 16, No. 1, Nature Publishing Group, Jan. 1998, 49-53.

Vahedi, et al., "An integrated method for mutation detection using on-chip sample preparation, single-stranded conformation polymorphism, and heteroduplex analysis", *Electrophoresis*, (Abstract), vol. 25(14), STN Accession No. 2004:652828, 2004, 2346-2356.

Vambutas, Vida et al., "Chloride-driven 3,3'-dipropylthiodicarbocyanine (DiSC3-(5)) and tetraphenylphosphonium cation (TPP+) uptake by thylakoids: inhibition of uptake by antibodies raised to the major polypeptides of the chloride efflux active particle(s)", *Biochimica et Biophysica Acta*, vol. 893, 1987, 69-74.

Vida, Thomas A. et al., "A New Vital Stain for Visualizing Vacular Membrane Dynamics and Endocytosis in Yeast", *The Journal of Cell Biology*, vol. 128, No. 5, The Rockefeller University Press, Mar. 1, 1995, 779-792.

Visser, Nina V. et al., "Time-Resolved Fluorescence Investigations of the Interaction of the Voltage-Sensitive Probe RH421 with Lipid Membranes and Proteins", *Biochemistry*, vol. 34, American Chemical Society, 1995, 11777-11784.

Wang, Q. M., "Development of a conscious fluorescence assay for rhinovirus 14 3C protease using synthetic peptides", *Antiviral Chemistry & Chemotherapy*, vol. 8, No. 4, 1997, 303-310.

Wang, Lijuan, "Synthesis of Hydroxyl Substituted Benzoxazol Hemicyanine and asym-Cyanine Dyes", *Journal of Wuhan Univ.*, No. 2, Feb. 1991, 73-77.

Watkins, T. I., "The Effect of Changing the Quarternary Grouping in Diminisium Bromide", *Trypanocides of the Phenanthridine Series.*, Part I., 1952, 3059-3064.

Wawzonek, Stanley, "Preparation and Proton Spectra of 1-Aryl-1,2-dihydro2-Quinolones", *J. Heterocyclic Chem.*, 25, 1988, 381.

Weber, G et al., "Determination of the absolute quantum yield of fluorescent solutions", *Transactions of the Faraday Society*, vol. 53, 1957, 646-655.

Williams, Richard J. et al., "Comparison of Covalent and Noncovalent Labeling with Near-Infared Dyes for the High-Performance Liquid Chromatographic Determination of Human Serum Albumin", *Analytical Chemistry*, vol. 65, 1993, 601-605.

Wittung, Pernilla et al., "DNA-like double helix formed by peptide nucleic acid", *Nature*, 368, 1994, 561-563.

WO 1993/006482, PCT ISR, Jan. 11, 1993.
WO 1994/024213, PCT ISR, Aug. 4, 1994.
WO 1996/013552, PCT ISR, May 3, 1996.
WO 1996/036882, PCT ISR, Oct. 1, 1996.
WO 2000/066664, PCT ISR, Sep. 7, 2000.
WO 2005/056687, PCT ISR, Aug. 18, 2005.
WO 2005/056689, PCT ISR, Aug. 22, 2005.
WO 2005/083394, PCT ISR, Sep. 13, 2005.
WO 2006/124816, PCT ISR, Oct. 17, 2006.

Wu, Pengguang et al., "Resonance Energy Transfer: Methods and Applications", *Analytical Biochemistry*, vol. 218, No. 1, 1994, 1-13.

Yamana, K. et al., "Bis-pyrene-labeled oligonucleotide: sequence specificity of excimer and monomer fluorescence changes upon hybridization with DNA", *Bioconjug Chem*, vol. 13, No. 6, 2002, 1266-73.

Yamana, Kazushige et al., "Fluorescence Detection of Specific RNA Sequence Using 2'-Pyrene-Modified Oligoribonucleotides", *Angewandte Chemie International Edition in English*, vol. 40, No. 6, 2001, 1104-1106.

Yan, J. X. et al., "Protein Phosphorylation: Technologies for the Identification of Phosphoamino Acids", *J Chromatogr A*, 808, 1998, 23-41.

Yoshimura, et al., "Uncoating of Influenza Virus in Endosomes", *Journal of Virology*, 51(2), 1984, 497-504.

Zarling, D. A. et al., "Mapping of Lymphocyte Surface Polypeptide Antigens by Chemical Cross-Linking with BSOCOES", *J Immunol*, 124(2), 1980, 913-20.

PCT/US04/40886, International Report on Patentability and Written Opinion mailed Aug. 18, 2005.

* cited by examiner

METHINE-SUBSTITUTED CYANINE DYE COMPOUNDS

CROSS-REFERENCE TO RELATED APPLICATIONS

This application claims priority to U.S. Ser. No. 60/527,142, filed Dec. 5, 2003; and U.S. Ser. No. 60/554,452 filed Mar. 18, 2004 which disclosures are herein incorporated by reference.

FIELD OF THE INVENTION

The present invention relates to cyanine compounds useful for staining nucleic acids, including RNA. The invention has applications in the fields of molecular biology, particularly with respect to fluorescence-based assays.

BACKGROUND OF THE INVENTION

In selected fields of life sciences research, including for example biological, biomedical, genetic, fermentation, aquaculture, agricultural, forensic and environmental research, there may often occur the need to identify nucleic acids, qualitatively and quantitatively, in pure solutions and in biological samples. Such applications may benefit from fast, sensitive, and selective methodologies for detecting and/or quantifying nucleic acids of interest.

In particular, it may be helpful in some research venues to provide molecular species that at least somewhat selectively stain RNA even in the presence of DNA. That is, the probe or reagent may permit the researcher to distinguish RNA present in a sample from DNA in the same sample.

SUMMARY

Embodiments of the present invention provide nucleic acid reporter compounds, which are cyanine dyes that comprise at substituted methine bridge. These reporter compounds find use as nucleic acid stains, particularly for the fluorescent detection/quantitation of DNA.

In one embodiment, the nucleic acid reporter molecules have the formula:

Formula I

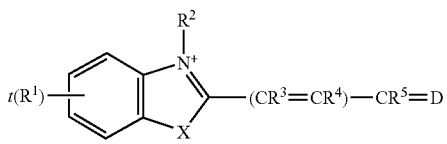

wherein at least one of $R^3$, $R^4$, and $R^5$ is an alkyl, substituted alkyl, a 5-, 6- or 7-membered heterocycloalkyl, a substituted 5-, 6- or 7-membered heterocycloalkyl, a 5-, 6- or 7-membered cycloalkyl, a substituted 5-, 6- or 7-membered cycloalkyl, a 5-, 6- or 7-membered heteroaryl, a substituted 5-, 6- or 7-membered heteroaryl, a 5-, 6- or 7-membered aryl or a substituted 5-, 6- or 7-membered aryl; and the remaining $R^3$, $R^4$ or $R^5$ are hydrogen.

In an exemplary embodiment at least one of $R^3$, $R^4$, and $R^5$ is a substituted alkyl, a substituted 5-, 6- or 7-membered heterocycloalkyl, a substituted 5-, 6- or 7-membered cycloalkyl, a substituted 5-, 6- or 7-membered heteroaryl, or a substituted 5-, 6- or 7-membered aryl that is substituted by an alkyl, $-(CH_2)_k-NR^6R^7$; $-COOR^8$, $NO_2$, or halogen, wherein k is an integer from 0 to about 6. The substituents $R^6$, $R^7$ and $R^8$ are independently hydrogen, alkyl, substituted alkyl, alkoxy, substituted alkoxy, sulfoalkyl or aminoalkyl. In one aspect at least one of $R^3$ and $R^4$ is a thiophenyl, substituted thiophenyl, adamantyl, substituted adamantly, phenyl, substituted phenyl, alkyl, substituted alkyl, benzyl or substituted benzyl.

These nucleic acid reporter molecules exhibit a fluorescence enhancement when non-covalently associated with a nucleic acid molecule. In one aspect, the fluorescence enhancement is greater when the nucleic acid is RNA than when the nucleic acid is DNA. In another aspect, the fluorescence enhancement is greater when the nucleic acid is DNA than when the nucleic acid is RNA.

The $R^1$ substituent is independently hydrogen, carboxy, sulfo, phosphate, phosphonate, amino, hydroxyl, trifluoromethyl, halogen, alkyl, substituted alkyl, alkoxy, substituted alkoxy, alkylamino, substituted alkylamino, dialkylamino, substituted dialkylamino, aminoalkyl, substituted aminoalkyl, fused benzene, substituted fused benzene, reactive group, solid support or carrier molecule and t is an integer from 1 to 4. In one aspect $R^1$ is alkoxy or halogen. In another aspect $R^1$ is methoxy, Br, Cl, or F.

The $R^2$ substituent is an alkyl, substituted alkyl, arylalkyl, substituted arylalkyl, heteroalkyl, substituted heteroalkyl, alkoxy, substituted alkoxy, carboxy, carboxyalkyl, hydroxy, hydroxyalkyl, sulfo, sulfoalkyl, amino, aminoalkyl, alkylamino, dialkylamino, or trialkylammonium. In one aspect $R^2$ is methyl, ethyl, propyl, or $-(CH_2)_3SO_3^-$.

X is O, S or Se.

The D is a substituted pyridinium, unsubstituted pyridinium, substituted quinolinium, unsubstituted quinolinium, substituted benzazolium or unsubstituted benzazolium moiety. In an exemplary embodiment, D has the formula:

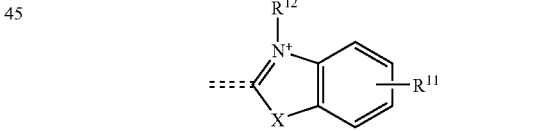

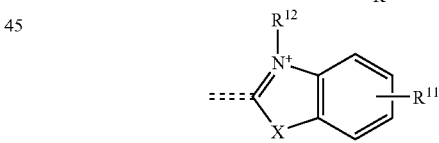

wherein $R^{11}$ is hydrogen, substituted alkyl, unsubstituted alkyl, substituted heteroalkyl, unsubstituted heteroalkyl, substituted aryl, unsubstituted aryl, substituted arylalkyl, unsubstituted arylalkyl, substituted heteroarylalkyl; unsubstituted heteroarylalkyl, substituted heteroaryl, unsubstituted heteroaryl substituted cycloalkyl, unsubstituted cycloalkyl, substituted heterocycloalkyl, unsubstituted heterocycloalkyl, halogen, alkoxy, substituted alkylamino, unsubstituted alkylamino, substituted alkylthio, unsubstituted alkylthio, reactive group, solid support, or carrier molecule and $R^{12}$ is an alkyl, substituted alkyl, arylalkyl, substituted arylalkyl, heteroalkyl, substituted heteroalkyl, alkoxy, substituted alkoxy, carboxy, carboxyalkyl, hydroxy, hydroxyalkyl, sulfo, sulfoalkyl, amino, aminoalkyl, alkylamino, dialkylamino, or trialkylammonium. Alternatively, $R^{11}$ in combination with an adjacent $R^{11}$ or $R^{12}$, together with the atoms to which they are joined, form a ring which is a 5-, 6- or 7-membered heterocycloalkyl, a substituted 5-, 6- or 7-membered heterocycloalkyl, a 5-, 6- or 7-membered cycloalkyl, a substituted 5-, 6- or 7-membered cycloalkyl, a 5-, 6- or 7-membered heteroaryl, a substituted 5-, 6- or 7-membered heteroaryl, a 5-, 6- or 7-membered aryl or a substituted 5-, 6- or 7-membered aryl.

In an exemplary embodiment of the kits, the nucleic acid reporter molecule has the formula:

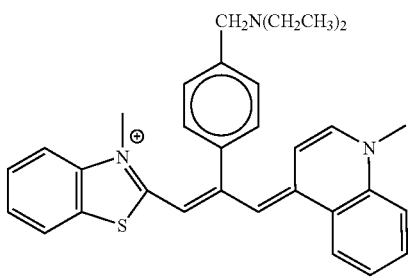

or the formula

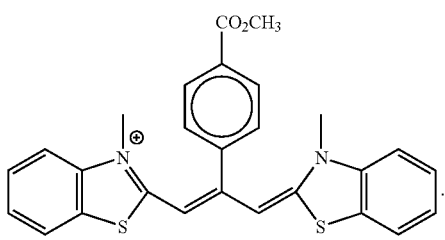

Additional embodiments of the present invention provide methods of detecting the presence or absence of nucleic acid, including method for detecting the presence or absence of RNA in the presence of DNA. The present methods comprise:
 a. combining a present nucleic acid reporter molecule with the sample to prepare a labeling mixture;
 b. incubating the labeling mixture for a sufficient amount of time for the nucleic acid reporter molecule to associate with nucleic acid in the sample to form an incubated mixture;
 c. illuminating the incubated sample with an appropriate wavelength to form an illuminated mixture; and,
 d. observing the illuminated mixture whereby the presence or absence of the nucleic acid in a sample is detected.

In one aspect, the nucleic acid reporter molecule has a RNA/DNA ratio of fluorescence enhancement greater than about one.

Also provided is a staining solution comprising a present nucleic acid reporter molecule and a detergent. The detergent is typically present in an aqueous solution at a concentration from about 0.0001% to about 0.05%. Detergents include CHAPTS, Triton-X, SDS and Tween 20. In a further aspect, the staining solution contains a low concentration of DNA, a low concentration being about 0.1 µg/ml to about 0.5 µg/ml.

Further embodiments provide complexes of the present compounds non-covalently associated with nucleic acid and compositions comprising a present compound and a sample. In one aspect the sample comprises biological fluids, buffer solutions, live cells, fixed cells, eukaryotic cells, prokaryotic cells, nucleic acid polymers, nucleotides, nucleosides, a polymeric gel or tissue sections. In a further aspect the sample is present in an aqueous solution, in or on a microarray or a microwell plate.

Additional embodiments of the present invention provide kits for the detection of nucleic acid, wherein the kit comprises any compound of the present invention. In a further embodiment, the kits comprise instructions for the detection of nucleic acid, particularly instructions for the detection of RNA in the presence of DNA. In yet another further embodiment, the kits comprises at least one component that is a sample preparation reagent, a buffering agent, an organic solvent, an aqueous nucleic acid reporter molecule dilution buffer, nucleic acid control, or an additional detection reagent.

BRIEF DESCRIPTION OF THE FIGURES

FIG. 4 is an overlay of two graphs with concentration of RNA 0-200 ng/mL, as described in Example 10.

DETAILED DESCRIPTION

Definitions

Figure 1:
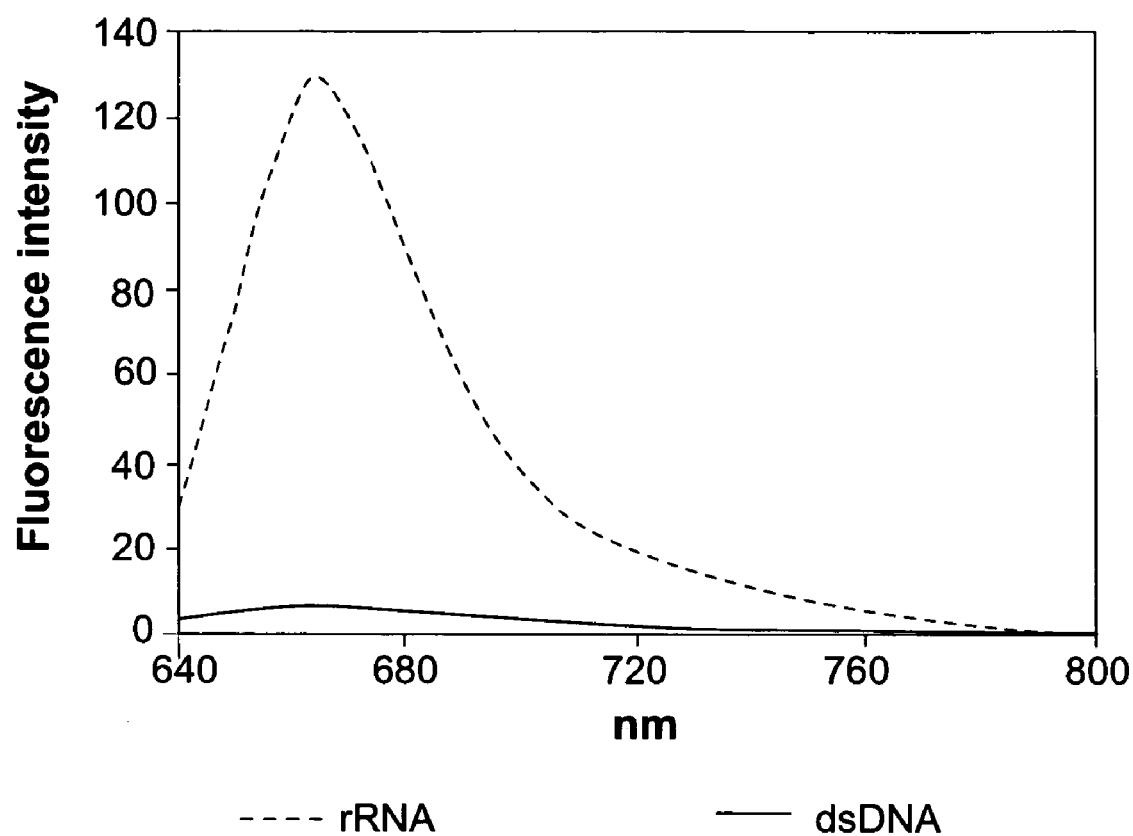
FIG. 1: A plot showing the intensity and emission spectra of the fluorescent signal from Compound 20 when associated with either rRNA or DNA (calf thymus) in solution, with excitation at 630 nm, as described in Example 7. Compound 20 demonstrates a 12 to 13-fold increase in signal when bound to RNA when compared to DNA.

Before describing the present invention in detail, it is to be understood that this invention is not limited to specific compositions or process steps, as such may vary. It must be noted that, as used in this specification and the appended claims, the singular form "a", "an" and "the" include plural referents unless the context clearly dictates otherwise. Thus, for example, reference to "a compound" includes a plurality of compounds and reference to "a nucleic acid" includes a plurality of nucleic acids and the like.

Unless defined otherwise, all technical and scientific terms used herein have the same meaning as commonly understood by one of ordinary skill in the art to which this invention is related. The following terms are defined for the purposes of understanding the present disclosure.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds described herein may be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.), VOGEL'S ENCYCLOPEDIA OF PRACTICAL ORGANIC CHEMISTRY 5$^{TH}$ ED., Longman Scientific and Technical Ltd., Essex, 1991, pp. 809-816; and Heller, *Acc. Chem. Res.* 23:128 (1990).

The compounds disclosed herein may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Where a disclosed compound includes a conjugated ring system, resonance stabilization may permit a formal electronic charge to be distributed over the entire molecule. While a particular charge may be depicted as localized on a particular ring system, or a particular heteroatom, it is commonly understood that a comparable resonance structure can be drawn in which the charge may be formally localized on an alternative portion of the compound.

Selected compounds having a formal electronic charge may be shown without an appropriate biologically compatible counterion. Such a counterion serves to balance the positive or negative charge present on the compound. As used herein, a substance that is biologically compatible is not toxic as used, and does not have a substantially deleterious effect on biomolecules. Examples of negatively charged counterions include, among others, chloride, bromide, iodide, sulfate, alkanesulfonate, arylsulfonate, phosphate, perchlorate, tetrafluoroborate, tetraarylboride, nitrate and anions of aromatic or aliphatic carboxylic acids. Preferred counterions may include chloride, iodide, perchlorate and various sulfonates. Examples of positively charged counterions include, among others, alkali metal, or alkaline earth metal ions, ammonium, or alkylammonium ions.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "acyl" or "alkanoyl" by itself or in combination with another term, means, unless otherwise stated, a stable straight or branched chain, or cyclic hydrocarbon radical, or combinations thereof, consisting of the stated number of carbon atoms and an acyl radical on at least one terminus of the alkane radical. The "acyl radical" is the group derived from a carboxylic acid by removing the —OH moiety therefrom.

The term "affinity" as used herein refers to the strength of the binding interaction of two molecules, such as a nucleic acid polymer and an intercalating agent or a positively charged moiety and a negatively charged moiety.

The term "alkyl," by itself or as part of another substituent means, unless otherwise stated, a straight or branched chain, or cyclic hydrocarbon radical, or combination thereof, which may be fully saturated, mono- or polyunsaturated and can include divalent ("alkylene") and multivalent radicals, having the number of carbon atoms designated (i.e. C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

Exemplary alkyl groups of use in the present invention contain between about one and about twenty five carbon atoms (e.g. methyl, ethyl and the like). Straight, branched or cyclic hydrocarbon chains having eight or fewer carbon atoms will also be referred to herein as "lower alkyl". In addition, the term "alkyl" as used herein further includes one or more substitutions at one or more carbon atoms of the hydrocarbon chain fragment. The term "amino" or "amine group" refers to the group —NR'R" (or NRR'R") where R, R' and R" are independently selected from the group consisting of hydrogen, alkyl, substituted alkyl, aryl, substituted aryl, aryl alkyl, substituted aryl alkyl, heteroaryl, and substituted heteroaryl. A substituted amine being an amine group wherein R' or R" is other than hydrogen. In a primary amino group, both R' and R" are hydrogen, whereas in a secondary amino group, either, but not both, R' or R" is hydrogen. In addition, the terms "amine" and "amino" can include protonated and quaternized versions of nitrogen, comprising the group —NRR'R" and its biologically compatible anionic counterions.

The term "aryl" as used herein refers to cyclic aromatic carbon chain having twenty or fewer carbon atoms, e.g., phenyl, naphthyl, biphenyl, and anthracenyl. One or more carbon atoms of the aryl group may also be substituted with, e.g., alkyl; aryl; heteroaryl; a halogen; nitro; cyano; hydroxyl, alkoxyl or aryloxyl; thio or mercapto, alkyl-, or arylthio; amino, alkylamino, arylamino, dialkyl-, diaryl-, or arylalkylamino; aminocarbonyl, alkylaminocarbonyl, arylaminocarbonyl, dialkylaminocarbonyl, diarylaminocarbonyl, or arylalkylaminocarbonyl; carboxyl, or alkyl- or aryloxycarbonyl; aldehyde; aryl- or alkylcarbonyl; iminyl, or aryl- or alkyliminyl; sulfo; alkyl- or alkylcarbonyl; iminyl, or aryl- or alkyliminyl; sulfo; alkyl- or arylsufonyl; hydroximinyl, or aryl- or alkoximinyl. In addition, two or more alkyl or heteroalkyl substituents of an aryl group may be combined to form fused aryl-alkyl or aryl-heteroalkyl ring systems (e.g., tetrahydronaphthyl). Substituents including heterocyclic groups (e.g., heteroaryloxy, and heteroaralkylthio) are defined by analogy to the above-described terms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a straight or branched chain, or cyclic carbon-containing radical, or combinations thereof, consisting of the stated number of carbon atoms and at least one heteroatom selected from the group consisting of O, N, Si, P, Se, and S, and wherein the nitrogen, phosphorous and sulfur atoms are optionally oxidized, and the nitrogen heteroatom is optionally be quaternized. The heteroatom(s) O, N, P, S, Se, and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. Up to two heteroatoms may be consecutive, such as, for example, —$CH_2$—NH—O$CH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "aryl" means, unless otherwise stated, a polyunsaturated, aromatic moiety that can be a single ring or multiple rings (preferably from 1 to 3 rings), which are fused together or linked covalently. The term "heteroaryl" refers to aryl groups (or rings) that contain from one to four heteroatoms selected from N, O, S, and Se wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3]dioxol-5-yl and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R" R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R" R'")=NR'", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R" R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxy, and fluoro($C_1$-$C_4$) alkyl, in a number ranging from zero to the total number of open valences on the aromatic ring system;

and where R', R'', R''' and R'''' are preferably independently selected from hydrogen, substituted or unsubstituted alkyl, substituted or unsubstituted heteroalkyl, substituted or unsubstituted aryl and substituted or unsubstituted heteroaryl. When a compound includes more than one R group, for example, each of the R groups is independently selected as are each R', R'', R''' and R'''' groups when more than one of these groups is present. In the schemes that follow, the symbol X represents "R" as described above.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR''R''')$_d$—, where s and d are independently integers of from 0 to 3, and X is —O—, —NR'—, —S—, —S(O)—, —S(O)$_2$—, or —S(O)$_2$NR'—. The substituents R, R', R'' and R''' are preferably independently selected from hydrogen or substituted or unsubstituted (C$_1$-C$_6$)alkyl.

As used herein, the term "heteroatom" includes oxygen (O), nitrogen (N), sulfur (S), phosphorus (P), selenium (Se), and silicon (Si), among others.

The term "amino" or "amine group" refers to the group —NR'R'' (or N$^+$RR'R'') where R, R' and R'' are independently selected from the group consisting of hydrogen, alkyl, substituted alkyl, aryl, substituted aryl, aryl alkyl, substituted aryl alkyl, heteroaryl, and substituted heteroaryl. A substituted amine being an amine group wherein R' or R'' is other than hydrogen. In a primary amino group, both R' and R'' are hydrogen, whereas in a secondary amino group, either, but not both, R' or R'' is hydrogen. In addition, the terms "amine" and "amino" can include protonated and quaternized versions of nitrogen, comprising the group —N$^+$RR'R'' and its biologically compatible anionic counterions.

The term "attachment site" as used herein refers to a site on a moiety or a molecule, e.g. a quencher, or a fluorescent dye, to which is covalently attached, or capable of being covalently attached, to a linker or another moiety.

The term "aqueous solution" as used herein refers to a solution that is predominantly water and retains the solution characteristics of water. Where the aqueous solution contains solvents in addition to water, water is typically the predominant solvent.

The term "Carboxyalkyl" as used herein refers to a group having the general formula —(CH$_2$)$_n$COOH wherein n is 1-18.

The term "carrier molecule" as used herein refers to a biological or a non-biological component that is covalently bonded to a compound of the present invention. Such components include, but are not limited to, an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof.

The term "complex" as used herein refers to the association of two or more molecules, usually by non-covalent bonding.

The term "cyanine dye" as used herein refers to a fluorogenic compound that comprises 1) a substituted or unsubstituted benzazolium moiety, 2) a polymethine bridge and 3) a substituted or unsubstituted benzazolium, pyridinium or quinolinium moiety. These monomer or dye moieties are capable of forming a non-covalent complex with nucleic acids and demonstrating an increased fluorescent signal after formation of the nucleic acid-dye complex.

The term "detectable response" as used herein refers to a change in or an occurrence of, a signal that is directly or indirectly detectable either by observation or by instrumentation. Typically, the detectable response is an optical response resulting in a change in the wavelength distribution patterns or intensity of absorbance or fluorescence or a change in light scatter, fluorescence lifetime, fluorescence polarization, or a combination of the above parameters.

The term "kit" as used refers to a packaged set of related components, typically one or more compounds or compositions.

The term "Linker" or "L", as used herein, refers to a single covalent bond or a series of stable covalent bonds incorporating 1-20 nonhydrogen atoms selected from the group consisting of C, N, O, S and P that covalently attach the fluorogenic or fluorescent compounds to another moiety such as a chemically reactive group or a biological and non-biological component. Exemplary linking members include a moiety that includes —C(O)NH—, —C(O)O—, —NH—, —S—, —O—, and the like. A "cleavable linker" is a linker that has one or more cleavable groups that may be broken by the result of a reaction or condition. The term "cleavable group" refers to a moiety that allows for release of a portion, e.g., a fluorogenic or fluorescent moiety, of a conjugate from the remainder of the conjugate by cleaving a bond linking the released moiety to the remainder of the conjugate. Such cleavage is either chemical in nature, or enzymatically mediated. Exemplary enzymatically cleavable groups include natural amino acids or peptide sequences that end with a natural amino acid.

In addition to enzymatically cleavable groups, it is within the scope of the present invention to include one or more sites that are cleaved by the action of an agent other than an enzyme. Exemplary non-enzymatic cleavage agents include, but are not limited to, acids, bases, hydroxylamine, light (e.g., nitrobenzyl derivatives, phenacyl groups, benzoin esters), and heat. Many cleavable groups are known in the art. See, for example, Jung et al., *Biochim. Biophys. Acta,* 761: 152-162 (1983); Joshi et al., *J. Biol. Chem.,* 265:14518-14525 (1990); Zarling et al., *J. Immunol.,* 124: 913-920 (1980); Bouizar et al., *Eur. J. Biochem.,* 155: 141-147 (1986); Park et al., *J. Biol. Chem.,* 261: 205-210 (1986); Browning et al., *J. Immunol.,* 143: 1859-1867 (1989). Moreover, a broad range of cleavable, bifunctional (both homo- and hetero-bifunctional) spacer arms are commercially available.

An exemplary cleavable group, an ester, is cleavable group that may be cleaved by a reagent, e.g. sodium hydroxide or hydroxylamine, resulting in a carboxylate-containing fragment and a hydroxyl-containing product.

The linker can be used to attach the compound to another component of a conjugate, such as a targeting moiety (e.g., antibody, ligand, non-covalent protein-binding group, etc.), an analyte, a biomolecule, a drug and the like.

As used herein, "nucleic acid" or "nucleic acid polymer" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, and electrostatic interaction to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications such as capping with a quencher, a fluorophore, a reactive group or another moiety.

The term "nucleic acid reporter molecule" as used herein refers to the present cyanine compounds wherein the methine bridge is substituted by at least one aryl, heteroaryl or substituted alkyl group.

The term "reactive group" as used herein refers to a group that is capable of reacting with another chemical group to form a covalent bond, i.e. is covalently reactive under suitable reaction conditions, and generally represents a point of attachment for another substance. The reactive group is a moiety, such as carboxylic acid, amine, alcohol or succinimidyl ester, on the compounds of the present invention that is capable of chemically reacting with a functional group on a different compound to form a covalent linkage resulting in a fluorescent or fluorogenic labeled component. Reactive groups generally include nucleophiles, electrophiles and photoactivatable groups.

Exemplary reactive groups include, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, thiosulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application to or modification for a particular purpose is within the ability of one of skill in the art (see, for example, Sandier and Karo, eds. ORGANIC FUNCTIONAL GROUP PREPARATIONS, Academic Press, San Diego, 1989).

The term "reporter molecule" as used herein refers to any luminescent molecule that is capable of associating with a nucleic acid polymer and producing a detectable signal. Typically, reporter molecules include unsymmetrical cyanine dyes, homo- or heterodimers or oligomers of cyanine dyes, ethidium bromide, DAPI, Hoechst, acridine and styryl dyes that are capable of producing a detectable signal upon appropriate wavelength excitation.

The term "salt thereof," as used herein includes salts of the agents of the invention and their conjugates, which are preferably prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of base addition salts include sodium, potassium, calcium, ammonium, organic amino, or magnesium, or a similar salt. When compounds of the present invention contain relatively basic functionalities, acid addition salts can be obtained by contacting the neutral form of such compounds with a sufficient amount of the desired acid, either neat or in a suitable inert solvent. Examples of addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The term "sample" as used herein refers to any material that may contain nucleic acid. The sample may also include diluents, buffers, detergents, and contaminating species, debris and the like that are found mixed with the target. Illustrative examples include urine, sera, blood plasma, total blood, saliva, tear fluid, cerebrospinal fluid, secretory fluids and the like. Also included are solid, gel or substances such as mucus, body tissues, cells and the like suspended or dissolved in liquid materials such as buffers, extractants, solvents and the like. Typically, the sample is a live cell, a biological fluid that comprises endogenous host cell proteins, nucleic acid polymers, nucleotides, oligonucleotides, peptides and buffer solutions. The sample may be dissolved or suspended in an aqueous solution, a viable cell culture or immobilized on a solid or semi solid surface such as a polyacrylamide gel, membrane blot or on a microarray.

The term "solid support," as used herein, refers to a material that is substantially insoluble in a selected solvent system, or which can be readily separated (e.g., by precipitation) from a selected solvent system in which it is soluble. Solid supports useful in practicing the present invention can include groups that are activated or capable of activation to allow selected species to be bound to the solid support. Solid supports may be present in a variety of forms, including a chip, wafer or well, onto which an individual, or more than one compound, of the invention is bound such as a polymeric bead or particle.

The term "sulfoalkyl," as used herein refers to a group having the general formula —$(CH_2)_n SO^-_3$ wherein n is 1-18.

The Compounds

In general, for ease of understanding the present invention, the nucleic acid reporter molecules and corresponding substituents will first be described in detail, followed by the many and varied methods in which the compounds find uses, which is followed by exemplified methods of use and synthesis of novel compounds that are particularly advantageous for use with the methods of the present invention.

The compounds of the present disclosure typically exhibit a fluorescence enhancement when non-covalently associated with a nucleic acid. For selected compounds, the fluorescence enhancement is greater when the nucleic acid is RNA than when the nucleic acid is DNA.

In one embodiment the present invention provides nucleic acid complexing compounds that comprise at substituted methine bridge. Without wishing to be bound by theory, it is believed that the selection of a nonhydrogen methine substituent (one of $R^3$, $R^4$, and $R^5$) may permit the tuning of selectivity and affinity of the resulting compound for particular nucleic acids. In particular, it is believed that the presence of a nonhydrogen methine substituent increases the selectivity and affinity of the resulting compound for RNA, when compared to the same compound when binding to DNA. The fluorescence enhancement of the resulting RNA complex may be greater than that of the corresponding DNA complex.

The methine substituents is typically bulky such that is affects the association with DNA. Typically such substituents include, but are not limited to, alkyl, substituted alkyl, a 5-, 6- or 7-membered heterocycloalkyl, a substituted 5-, 6- or 7-membered heterocycloalkyl, a 5-, 6- or 7-membered cycloalkyl, a substituted 5-, 6- or 7-membered cycloalkyl, a 5-, 6- or 7-membered heteroaryl, a substituted 5-, 6- or 7-membered heteroaryl, a 5-, 6- or 7-membered aryl or a substituted 5-, 6- or 7-membered aryl.

Typically, the nucleic acid complexing compounds are unsymmetrical cyanine dyes including, but are not limited to, any compound disclosed in U.S. Pat. Nos. 4,957,870; 4,883,867; 5,436,134; 5,658,751, 5,534,416 and 5,863,753, when substituted with a negatively charged moiety. There is no intended limitation on the nucleic acid complexing compound.

In an exemplary embodiment, the present nucleic acid reporter molecules may be described by the formula:

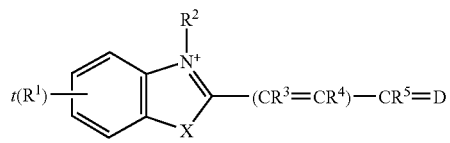

Formula I wherein at least one of $R^3$, $R^4$, and $R^5$ is an alkyl, substituted alkyl, a 5-, 6- or 7-membered heterocycloalkyl, a substituted 5-, 6- or 7-membered heterocycloalkyl, a 5-, 6- or 7-membered cycloalkyl, a substituted 5-, 6- or 7-membered cycloalkyl, a 5-, 6- or 7-membered heteroaryl, a substituted 5-, 6- or 7-membered heteroaryl, a 5-, 6- or 7-membered aryl or a substituted 5-, 6- or 7-membered aryl; and the remaining $R^3$, $R^4$ or $R^5$ are hydrogen.

Each nonhydrogen methine substituent may itself be further substituted one or more times by alkyl, amino, carboxy, nitro, or halogen. Typically one or two of $R^3$, $R^4$, and $R^5$ is nonhydrogen. More typically, exactly one of $R^3$, $R^4$, and $R^5$ is nonhydrogen. In one aspect of the invention, $R^4$ is nonhydrogen.

In particular, where at least one of $R^3$, $R^4$, and $R^5$ is an alkyl, aryl, heteroaryl, cyclic, or heterocyclic moiety, the moiety may include 3-20 non-hydrogen atoms selected from the group consisting of O, N, S, P and C, and be optionally further substituted by $C_1$-$C_6$ alkyl, —$NR^6R^7$; —$COOR^8$, $NO_2$, or halogen, wherein $R^6$, $R^7$, and $R^8$ are independently hydrogen, $C_1$-$C_6$ alkyl, $C_1$-$C_6$ alkoxy, sulfoalkyl or aminoalkyl.

Where $R^4$ is a nonhydrogen substituent, $R^4$ may be alkyl, cycloalkyl, heteroaryl, or aryl. More particularly, $R^4$ may be selected from linear or branched alkyl, cycloalkyl, thiophenyl, furanyl, and phenyl substituents, that may be further substituted by one or more of hydrogen, F, Cl, $CF_3$, —$CO_2CH_3$, $NO_2$, amino, $C_1$-$C_6$ alkoxy, phenoxy, and $C_1$-$C_6$ alkyl that is itself optionally further substituted by amino, sulfo, or carboxy.

The $R^1$ substituents may include any aryl group substituent, including additional fused 5- or 6-membered rings. Where each $R^1$ is independently hydrogen, carboxy, sulfo, phosphate, phosphonate, amino, hydroxyl, trifluoromethyl, halogen, alkyl, substituted alkyl, alkoxy, alkylamino, substituted alkylamino, dialkylamino, substituted dialkylamino, aminoalkyl, substituted aminoalkyl, fused benzene, substituted fused benzene, reactive group, solid support or carrier molecule, wherein t is an integer from 1 to 4. Each alkyl portion of which is optionally substituted by alkyl group substituents, as described above. In particular, the alkyl groups substituents may be selected from the group consisting of carboxy, sulfo, phosphate, phosphonate, amino, and hydroxy. Where $R^1$ is nonhydrogen, $R^1$ may be an alkoxy substituent, or a halogen substituent, more preferably at least one $R^1$ is methoxy, Br, Cl, or F.

The $R^2$ substituent is an alkyl, substituted alkyl, arylalkyl, substituted arylalkyl, heteroalkyl, substituted heteroalkyl, alkoxy, substituted alkoxy, carboxy, carboxyalkyl, hydroxy, hydroxyalkyl, sulfo, sulfoalkyl, amino, aminoalkyl, alkylamino, dialkylamino, or trialkylammonium. In particular, $R^2$ may be selected from lower alkyl or sulfoalkyl, more preferably methyl, ethyl, propyl, or —$(CH_2)_3SO_3^-$.

The X moiety is selected from S, O, or Se, forming a benzothiazole, benzoxazole, or benzoselenazole heterocyclic ring system, respectively. Typically, X is S or O, and more typically, X is S.

The D moiety is a substituted or unsubstituted ring system, including pyridinium, quinolinium or benzazolium ring systems. For example, the D moiety may include the following ring systems (additional substituents omitted for clarity):

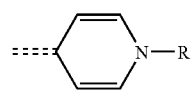

Formula II

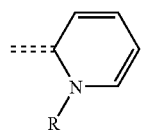

Formula III

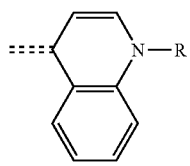

Formula IV

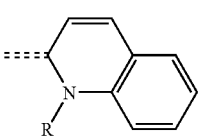

Formula V

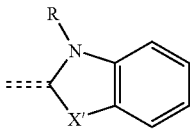

Formula VI where X' may be the same or different than X as described above

The D ring system is optionally further substituted by any aryl group substituent, as described above.

In an exemplary embodiment, the D moiety has the formula:

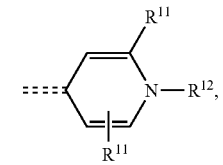

Formula VII

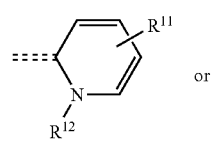

(Formula VIII)

or

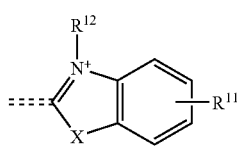

Formula IX wherein $R^{11}$ is hydrogen, substituted alkyl, unsubstituted alkyl, substituted heteroalkyl, unsubstituted heteroalkyl, substituted aryl, unsubstituted aryl, substituted arylalkyl, unsubstituted arylalkyl, substituted heteroarylalkyl; unsubstituted heteroarylalkyl, substituted heteroaryl, unsubstituted heteroaryl, substituted cycloalkyl, unsubstituted cycloalkyl, substituted heterocycloalkyl, unsubstituted heterocycloalkyl, halogen, alkoxy, substituted alkylamino, unsubstituted alkylamino, substituted alkylthio, unsubstituted alkylthio, reactive group, solid support, or carrier molecule.

The $R^{12}$ substituent is an alkyl, substituted alkyl, arylalkyl, substituted arylalkyl, heteroalkyl, substituted heteroalkyl, alkoxy, substituted alkoxy, carboxy, carboxyalkyl, hydroxy, hydroxyalkyl, sulfo, sulfoalkyl, amino, aminoalkyl, alkylamino, dialkylamino, or trialkylammonium; or $R^{11}$ in combination with an adjacent $R^{11}$ or $R^{12}$, together with the atoms to which they are joined, form a ring which is a 5-, 6- or 7-membered heterocycloalkyl, a substituted 5-, 6- or 7-membered heterocycloalkyl, a 5-, 6- or 7-membered cycloalkyl, a substituted 5-, 6- or 7-membered cycloalkyl, a 5-, 6- or 7-membered heteroaryl, a substituted 5-, 6- or 7-membered heteroaryl, a 5-, 6- or 7-membered aryl or a substituted 5-, 6- or 7-membered aryl.

In an exemplary embodiment, the present compounds have the formula:

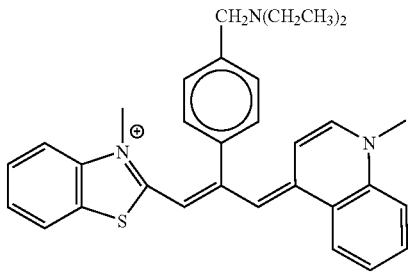

or the formula

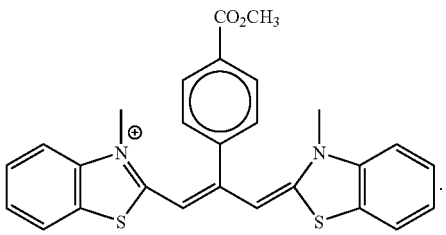

The compounds disclosed herein are readily modified to permit selectable alteration of the permeability, affinity, absorption, and emission properties (for example, see U.S. Pat. No. 5,658,751, hereby incorporated by reference). The resulting compounds may be tailored to cover most of the visible and near-infrared spectrum.

Synthesis

The reporter compounds disclosed herein may be prepared using a two-part synthetic strategy: First, the preparation of an benzazolium moiety containing a methine substituent, followed by addition of the appropriate pyridinium, quinolinium or benzazolium moiety. Typically each component is selected so as to incorporate the desired and/or appropriate chemical substituents, or functional groups that may be converted to the desired and/or appropriate chemical substituents. The synthetic strategies and procedures that may be used to prepare and combine these precursors so as to yield the disclosed compounds is generally well understood by one skilled in the art, including a variety of modifications and variations thereof. Herein are some useful general methods for the synthesis of selected compounds, including the incorporation of some chemical modifications.

Synthesis of the disclosed compounds, including the desired substituent on the trimethine bridge, may be facilitated by the initial preparation of selected intermediate compounds. For example, the intermediate benzazole moiety may be described using one of the following general structures. For the sake of simplicity, most of the substituents are shown as hydrogen, however this should not be considered limiting the breadth of the following disclosure.

Formula (X)

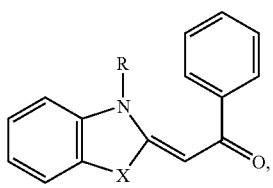

Formula (XI)

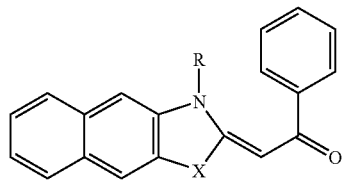

-continued

Formula (XII)

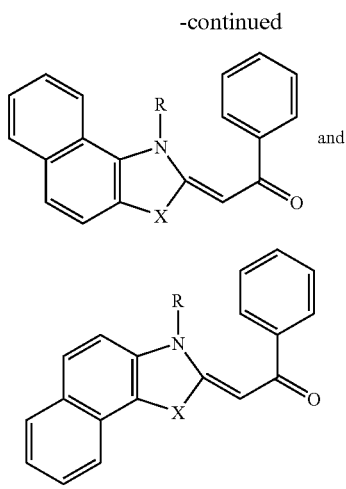

and

Formula (XIII)

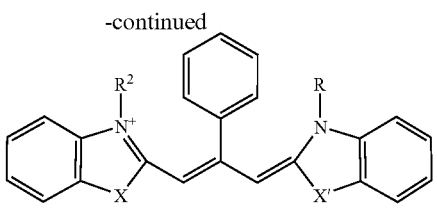

If X is O, the precursor compound is a benzoxazolium; if X is S it is a benzothiazolium; if X is Se it is a benzoselenazolium. The commercial availability of suitable starting materials and relative ease of synthesis may make compounds where X is O or S more attractive.

The desired $R^1$ substituents are typically incorporated in the parent benzazole molecule prior to quaternization with an alkylating agent. $R^2$ is typically incorporated by quaternization of the parent heterocycle with an alkylating agent, typically a source of $(R^2)^+$. The alkylating reagent may be an alkyl halide such as ethyl iodide, an alkylsulfonate such as methyl p-toluenesulfonate or a cyclic sulfonate such as propanesultone or butanesultone. The benzazolium moiety may then be subsequently reacted with an aromatic acid chloride to generate the desired benzoketone key intermediate which can be activated by phosphorous oxychloride followed by the addition of the desired pyridinium, quinolinium or benzazolium moiety, or "D" moiety.

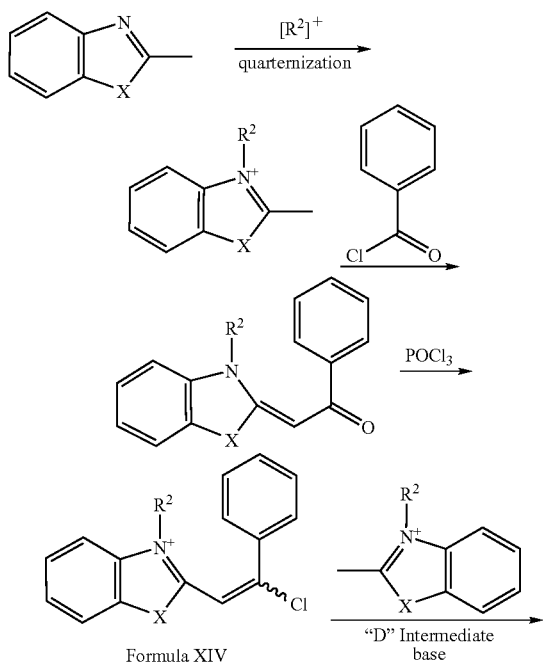

Although the above reaction scheme depicts the use of a benzoyl chloride reagent, it should be appreciated that the selection of reagent is dependent upon the nature of the methine substituent desired, and that a variety of reagents may be used, as shown in Example 1.

Similarly, although the D moiety depicted above is a benzazole, a variety of D intermediates, including pyridinium, quinolinium and benzazolium intermediates, may be used to complete the synthesis as described above. Selected examples of such variations are described in Examples 1-6.

Specific examples of D moieties appropriate for the above synthetic scheme may be found in, for example, U.S. Pat. No. 5,436,134, hereby incorporated by reference. The pyridinium, quinolinium or benzazolium moiety may be fused to additional rings, resulting in dyes that absorb and emit at longer wavelengths (for example, see U.S. Pat. No. 6,027,709, hereby incorporated by reference).

Reactive Groups, Carrier Molecules and Solid Supports

The present compounds, in certain embodiments, are chemically reactive wherein the compounds comprise a reactive group. In a further embodiment, the compounds comprise a carrier molecule or solid support. These substituents, reactive groups, carrier molecules, and solid supports, comprise a linker that is used to covalently attach the substituents to any of the moieties of the present compounds. The solid support, carrier molecule or reactive group may be directly attached (where linker is a single bond) to the moieties or attached through a series of stable bonds, as disclosed above.

Any combination of linkers may be used to attach the carrier molecule, solid support or reactive group and the present compounds together. The linker may also be substituted to alter the physical properties of the reporter moiety or chelating moiety, such as spectral properties of the dye. Examples of L include substituted or unsubstituted polyalkylene, arylene, alkylarylene, arylenealkyl, or arylthio moieties.

The linker typically incorporates 1-30 nonhydrogen atoms selected from the group consisting of C, N, O, S and P. The linker may be any combination of stable chemical bonds, optionally including, single, double, triple or aromatic carbon-carbon bonds, as well as carbon-nitrogen bonds, nitrogen-nitrogen bonds, carbon-oxygen bonds, sulfur-sulfur bonds, carbon-sulfur bonds, phosphorus-oxygen bonds, phosphorus-nitrogen bonds, and nitrogen-platinum bonds. Typically the linker incorporates less than 15 nonhydrogen atoms and are composed of any combination of ether, thioether, thiourea, amine, ester, carboxamide, sulfonamide, hydrazide bonds and aromatic or heteroaromatic bonds. Typically the linker is a combination of single carbon-carbon bonds and carboxamide, sulfonamide or thioether bonds. The bonds of the linker typically result in the following moieties that can be found in the linker: ether, thioether, carboxamide, thiourea, sulfonamide, urea, urethane, hydrazine, alkyl, aryl, heteroaryl, alkoxy, cycloalkyl and amine moieties. Examples of a linker include substituted or unsubstituted polymethylene, arylene, alkylarylene, arylenealkyl, and arylthio.

In one embodiment, the linker contains 1-6 carbon atoms; in another, the linker comprises a thioether linkage. Exemplary linking members include a moiety that includes —C(O)NH—, —C(O)O—, —NH—, —S—, —O—, and the like. In another embodiment, the linker is or incorporates the formula —$(CH_2)_d(CONH(CH_2)_e)_z$— or where d is an integer from 0-5, e is an integer from 1-5 and z is 0 or 1. In a further embodiment, the linker is or incorporates the formula —O—$(CH_2)$—. In yet another embodiment, the linker is or incorporates a phenylene or a 2-carboxy-substituted phenylene.

An important feature of the linker is to provide an adequate space between the carrier molecule, reactive group or solid support and the dye so as to prevent steric hinderance. Therefore, the linker of the present compound is important for (1) attaching the carrier molecule, reactive group or solid support to the compound, (2) providing an adequate space between the carrier molecule, reactive group or solid support and the compound so as not to sterically hinder the action of the compound and (3) for altering the physical properties of the present compounds.

In another exemplary embodiment of the invention, the present compounds are chemically reactive, and are substituted by at least one reactive group. The reactive group functions as the site of attachment for another moiety, such as a carrier molecule or a solid support, wherein the reactive group chemically reacts with an appropriate reactive or functional group on the carrier molecule or solid support.

Reactive groups or reactive group precursors may be positioned during the formation of the present compounds. Thus, compounds incorporating a reactive group can be reacted with and attached to a wide variety of biomolecules or non-biomolecules that contain or are modified to contain functional groups with suitable reactivity. When a labeled component includes a compound as disclosed herein, then this conjugate typically possesses the nucleic acid staining abilities of the parent compound, particularly RNA staining. However, the present fluorescent compounds can also function as reporter molecules for the labeled components wherein the nucleic acid binding properties of the reagents may not employed.

Preferred reactive groups for incorporation into the disclosed compounds may be selected to react with an amine, a thiol or an alcohol. In an exemplary embodiment, the compounds of the invention further comprise a reactive group that is an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, an imido ester, an isocyanate, an isothiocyanate, a maleimide, a phosphoramidite, a photoactivatable group, a reactive platinum complex, a silyl halide, a sulfonyl halide, and a thiol. In a particular embodiment the reactive group is selected from the group consisting of carboxylic acid, succinimidyl ester of a carboxylic acid, hydrazide, amine and a maleimide. In exemplary embodiment, at least one member selected from $R^1$, $R^2$, $R^{11}$, or $R^{12}$ comprises a reactive group. Preferably, at least one of $R^1$ or $R^{11}$ comprises a reactive group or is attached to a reactive group. Alternatively, if the present compound comprises a carrier molecule or solid support a reactive group may be covalently attached independently to those substituents, allowing for further conjugation to a another dye, carrier molecule or solid support.

In one aspect, the compound comprises at least one reactive group that selectively reacts with an amine group. This amine-reactive group is selected from the group consisting of succinimidyl ester, sulfonyl halide, tetrafluorophenyl ester and iosothiocyanates. Thus, in one aspect, the present compounds form a covalent bond with an amine-containing molecule in a sample. In another aspect, the compound comprises at least one reactive group that selectively reacts with a thiol group. This thiol-reactive group is selected from the group consisting of maleimide, haloalkyl and haloacetamide (including any reactive groups disclosed in U.S. Pat. Nos. 5,362,628; 5,352,803 and 5,573,904).

The pro-reactive groups are synthesized during the formation of the monomer moieties and carrier molecule and solid support containing compounds to provide chemically reactive compounds. In this way, compounds incorporating a reactive group can be covalently attached to a wide variety of carrier molecules or solid supports that contain or are modified to contain functional groups with suitable reactivity, resulting in chemical attachment of the components. In an exemplary embodiment, the reactive group of the compounds of the invention and the functional group of the carrier molecule or solid support comprise electrophiles and nucleophiles that can generate a covalent linkage between them. Alternatively, the reactive group comprises a photoactivatable group, which becomes chemically reactive only after illumination with light of an appropriate wavelength. Typically, the conjugation reaction between the reactive group and the carrier molecule or solid support results in one or more atoms of the reactive group being incorporated into a new linkage attaching the present compound of the invention to the carrier molecule or solid support. Selected examples of functional groups and linkages are shown in Table 1, where the reaction of an electrophilic group and a nucleophilic group yields a covalent linkage.

TABLE 1

Examples of some routes to useful covalent linkages

| Electrophilic Group | Nucleophilic Group | Resulting Covalent Linkage |
|---|---|---|
| activated esters* | amines/anilines | carboxamides |
| acrylamides | thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| halotriazines | thiols | triazinyl thioethers |
| imido esters | amines/anilines | amidines |
| isocyanates | amines/anilines | ureas |
| isocyanates | alcohols/phenols | urethanes |

TABLE 1-continued

Examples of some routes to useful covalent linkages

| Electrophilic Group | Nucleophilic Group | Resulting Covalent Linkage |
| --- | --- | --- |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

\* Activated esters, as understood in the art, generally have the formula —COΩ, where Ω is a good leaving group (e.g., succinimidyloxy (—$OC_4H_4O_2$) sulfosuccinimidyloxy (—$OC_4H_3O_2$—$SO_3H$), -1-oxybenzotriazolyl (—$OC_6H_4N_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —$OCOR^a$ or —$OCNR^aNHR^b$, where $R^a$ and $R^b$, which may be the same or different, are $C_1$-$C_6$ alkyl, $C_1$-$C_6$ perfluoroalkyl, or $C_1$-$C_6$ alkoxy; or cyclohexyl, 3-dimethylaminopropyl, or N-morpholinoethyl).

\*\* Acyl azides can also rearrange to isocyanates

Choice of the reactive group used to attach the compound of the invention to the substance to be conjugated typically depends on the reactive or functional group on the substance to be conjugated and the type or length of covalent linkage desired. The types of functional groups typically present on the organic or inorganic substances (biomolecule or non-biomolecule) include, but are not limited to, amines, amides, thiols, alcohols, phenols, aldehydes, ketones, phosphates, imidazoles, hydrazines, hydroxylamines, disubstituted amines, halides, epoxides, silyl halides, carboxylate esters, sulfonate esters, purines, pyrimidines, carboxylic acids, olefinic bonds, or a combination of these groups. A single type of reactive site may be available on the substance (typical for polysaccharides or silica), or a variety of sites may occur (e.g., amines, thiols, alcohols, phenols), as is typical for proteins.

Typically, the reactive group will react with an amine, a thiol, an alcohol, an aldehyde, a ketone, or with silica. Preferably, reactive groups react with an amine or a thiol functional group, or with silica. In one embodiment, the reactive group is an acrylamide, an activated ester of a carboxylic acid, an acyl azide, an acyl nitrile, an aldehyde, an alkyl halide, a silyl halide, an anhydride, an aniline, an aryl halide, an azide, an aziridine, a boronate, a diazoalkane, a haloacetamide, a halotriazine, a hydrazine (including hydrazides), an imido ester, an isocyanate, an isothiocyanate, a maleimide, a phosphoramidite, a reactive platinum complex, a sulfonyl halide, or a thiol group. By "reactive platinum complex" is particularly meant chemically reactive platinum complexes such as described in U.S. Pat. No. 5,714,327.

Where the reactive group is an activated ester of a carboxylic acid, such as a succinimidyl ester of a carboxylic acid, a sulfonyl halide, a tetrafluorophenyl ester or an isothiocyanates, the resulting compound is particularly useful for preparing conjugates of carrier molecules such as proteins, nucleotides, oligonucleotides, or haptens. Where the reactive group is a maleimide, haloalkyl or haloacetamide (including any reactive groups disclosed in U.S. Pat. Nos. 5,362,628; 5,352,803 and 5,573,904 (supra)) the resulting compound is particularly useful for conjugation to thiol-containing substances. Where the reactive group is a hydrazide, the resulting compound is particularly useful for conjugation to periodate-oxidized carbohydrates and glycoproteins, and in addition is an aldehyde-fixable polar tracer for cell microinjection. Where the reactive group is a silyl halide, the resulting compound is particularly useful for conjugation to silica surfaces, particularly where the silica surface is incorporated into a fiber optic probe subsequently used for remote ion detection or quantitation.

In a particular aspect, the reactive group is a photoactivatable group such that the group is only converted to a reactive species after illumination with an appropriate wavelength. An appropriate wavelength is generally a UV wavelength that is less than 400 nm. This method provides for specific attachment to only the target molecules, either in solution or immobilized on a solid or semi-solid matrix. Photoactivatable reactive groups include, without limitation, benzophenones, aryl azides and diazirines.

Preferably, the reactive group is a photoactivatable group, succinimidyl ester of a carboxylic acid, a haloacetamide, haloalkyl, a hydrazine, an isothiocyanate, a maleimide group, an aliphatic amine, a silyl halide, a cadaverine or a psoralen. More preferably, the reactive group is a succinimidyl ester of a carboxylic acid, a maleimide, an iodoacetamide, or a silyl halide. In a particular embodiment the reactive group is a succinimidyl ester of a carboxylic acid, a sulfonyl halide, a tetrafluorophenyl ester, an iosothiocyanates or a maleimide.

The selection of a covalent linkage to attach the reporter molecule to the carrier molecule or solid support typically depends on the chemically reactive group on the component to be conjugated. The discussion regarding reactive groups in the section immediately preceding is relevant here as well. Exemplary reactive groups typically present on the biological or non-biological components include, but are not limited to, amines, thiols, alcohols, phenols, aldehydes, ketones, phosphates, imidazoles, hydrazines, hydroxylamines, disubstituted amines, halides, epoxides, sulfonate esters, purines, pyrimidines, carboxylic acids, or a combination of these groups. A single type of reactive site may be available on the component (typical for polysaccharides), or a variety of sites may occur (e.g. amines, thiols, alcohols, phenols), as is typical for proteins. A carrier molecule or solid support may be conjugated to more than one reporter molecule, which may be the same or different, or to a substance that is additionally modified by a hapten. Although some selectivity can be obtained by careful control of the reaction conditions, selectivity of labeling is best obtained by selection of an appropriate reactive compound.

In another exemplary embodiment, the present compound is covalently bound to a carrier molecule. If the compound has a reactive group, then the carrier molecule can alternatively be linked to the compound through the reactive group. The reactive group may contain both a reactive functional moiety and a linker, or only the reactive functional moiety.

A variety of carrier molecules are useful in the present invention. Exemplary carrier molecules include antigens, steroids, vitamins, drugs, haptens, metabolites, toxins, environmental pollutants, amino acids, peptides, proteins, nucleic acids, nucleic acid polymers, carbohydrates, lipids, and polymers. In exemplary embodiment, at least one member selected from $R^1$, $R^2$, $R^{11}$, or $R^{12}$ comprises a carrier molecule. Preferably, at least one of $R^1$ or $R^{11}$ comprises a carrier molecule or is attached to a carrier molecule. Alternatively, if the present compound comprises a reactive group or solid support a reactive group may be covalently attached independently to those substituents, allowing for further conjugation to a reactive group, carrier molecule or solid support.

In an exemplary embodiment, the carrier molecule comprises an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof. In another exemplary embodiment, the carrier molecule is selected from a hapten, a nucleotide, an oligonucleotide, a nucleic acid polymer, a protein, a peptide or a polysaccharide. In a preferred embodiment the carrier molecule is amino acid, a peptide, a protein, a polysaccharide, a nucleoside, a nucleotide, an oligonucleotide, a nucleic acid, a hapten, a psoralen, a drug, a hormone, a lipid, a lipid assembly, a tyramine, a synthetic polymer, a polymeric microparticle, a biological cell, cellular components, an ion chelating moiety, an enzymatic substrate or a virus. In another preferred embodiment, the carrier molecule is an antibody or fragment thereof, an antigen, an avidin or streptavidin, a biotin, a dextran, an antibody binding protein, a fluorescent protein, agarose, and a non-biological microparticle. Typically, the carrier molecule is an antibody, an antibody fragment, antibody-binding proteins, avidin, streptavidin, a toxin, a lectin, or a growth factor. Preferred haptens include biotin, digoxigenin and fluorophores.

Antibody binding proteins include, but are not limited to, protein A, protein G, soluble Fc receptor, protein L, lectins, anti-IgG, anti-IgA, anti-IgM, anti-IgD, anti-IgE or a fragment thereof.

In an exemplary embodiment, the enzymatic substrate is selected from an amino acid, peptide, sugar, alcohol, alkanoic acid, 4-guanidinobenzoic acid, nucleic acid, lipid, sulfate, phosphate, —$CH_2OCO$alkyl and combinations thereof. Thus, the enzyme substrates can be cleave by enzymes selected from the group consisting of peptidase, phosphatase, glycosidase, dealkylase, esterase, guanidinobenzotase, sulfatase, lipase, peroxidase, histone deacetylase, endoglycoceramidase, exonuclease, reductase and endonuclease.

In another exemplary embodiment, the carrier molecule is an amino acid (including those that are protected or are substituted by phosphates, carbohydrates, or $C_1$ to $C_{22}$ carboxylic acids), or a polymer of amino acids such as a peptide or protein. In a related embodiment, the carrier molecule contains at least five amino acids, more preferably 5 to 36 amino acids. Exemplary peptides include, but are not limited to, neuropeptides, cytokines, toxins, protease substrates, and protein kinase substrates. Other exemplary peptides may function as organelle localization peptides, that is, peptides that serve to target the conjugated compound for localization within a particular cellular substructure by cellular transport mechanisms. Preferred protein carrier molecules include enzymes, antibodies, lectins, glycoproteins, histones, albumins, lipoproteins, avidin, streptavidin, protein A, protein G, phycobiliproteins and other fluorescent proteins, hormones, toxins and growth factors. Typically, the protein carrier molecule is an antibody, an antibody fragment, avidin, streptavidin, a toxin, a lectin, or a growth factor. Exemplary haptens include biotin, digoxigenin and fluorophores.

In another exemplary embodiment, the carrier molecule comprises a nucleic acid base, nucleoside, nucleotide or a nucleic acid polymer, optionally containing an additional linker or spacer for attachment of a fluorophore or other ligand, such as an alkynyl linkage (U.S. Pat. No. 5,047,519), an aminoallyl linkage (U.S. Pat. No. 4,711,955) or other linkage. In another exemplary embodiment, the nucleotide carrier molecule is a nucleoside or a deoxynucleoside or a dideoxynucleoside.

Exemplary nucleic acid polymer carrier molecules are single- or multi-stranded, natural or synthetic DNA or RNA oligonucleotides, or DNA/RNA hybrids, or incorporating an unusual linker such as morpholine derivatized phosphates (AntiVirals, Inc., Corvallis Oreg.), or peptide nucleic acids such as N-(2-aminoethyl)glycine units, where the nucleic acid contains fewer than 50 nucleotides, more typically fewer than 25 nucleotides.

In another exemplary embodiment, the carrier molecule comprises a carbohydrate or polyol that is typically a polysaccharide, such as dextran, FICOLL, heparin, glycogen, amylopectin, mannan, inulin, starch, agarose and cellulose, or is a polymer such as a poly(ethylene glycol). In a related embodiment, the polysaccharide carrier molecule includes dextran, agarose or FICOLL.

In another exemplary embodiment, the carrier molecule comprises a lipid (typically having 6-25 carbons), including glycolipids, phospholipids, and sphingolipids. Alternatively, the carrier molecule comprises a lipid vesicle, such as a liposome, or is a lipoprotein (see below). Some lipophilic substituents are useful for facilitating transport of the conjugated dye into cells or cellular organelles.

Alternatively, the carrier molecule is cells, cellular systems, cellular fragments, or subcellular particles. Examples of this type of conjugated material include virus particles, bacterial particles, virus components, biological cells (such as animal cells, plant cells, bacteria, or yeast), or cellular components. Examples of cellular components that can be labeled, or whose constituent molecules can be labeled, include but are not limited to lysosomes, endosomes, cytoplasm, nuclei, histones, mitochondria, Golgi apparatus, endoplasmic reticulum and vacuoles.

In another embodiment the carrier molecule is a metal chelating moiety. While any chelator that binds a metal ion of interest and gives a change in its fluorescence properties is a suitable conjugate, preferred metal chelating moieties are crown ethers, including diaryldiaza crown ethers, as described in U.S. Pat. No. 5,405,975 to Kuhn et al. (1995); derivatives of 1,2-bis-(2-aminophenoxyethane)-N,N,N',N'-tetraacetic acid (BAPTA), as described in U.S. Pat. No. 5,453,517 to Kuhn et al. (1995) (incorporated by reference) and U.S. Pat. No. 5,049,673 to Tsien et al. (1991); derivatives of 2-carboxymethoxy-aniline-N,N-diacetic acid (APTRA), as described by Ragu et al., *Am. J. Physiol.*, 256: C540 (1989); and pyridyl-based and phenanthroline metal ion chelators, as described in U.S. Pat. No. 5,648,270 to Kuhn et al. (1997).

Fluorescent conjugates of metal chelating moieties possess utility as indicators for the presence of a desired metal ion. While fluorescent ion-indicators are known in the art, the incorporation of the fluorinated fluorogenic and fluorescent compounds of the present invention imparts the highly advantageous properties of the instant fluorophores onto the resulting ion indicator.

The ion-sensing conjugates of the invention are optionally prepared in chemically reactive forms and further conjugated to polymers such as dextrans to improve their utility as sensors as described in U.S. Pat. Nos. 5,405,975 and 5,453,517.

In another exemplary embodiment, the carrier molecule non-covalently associates with organic or inorganic materials. Exemplary embodiments of the carrier molecule that possess a lipophilic substituent can be used to target lipid assemblies such as biological membranes or liposomes by non-covalent incorporation of the dye compound within the membrane, e.g., for use as probes for membrane structure or for incorporation in liposomes, lipoproteins, films, plastics, lipophilic microspheres or similar materials.

In an exemplary embodiment, the carrier molecule comprises a specific binding pair member wherein the present compounds are conjugated to a specific binding pair member and are used to detect an analyte in a sample. Alternatively, the presence of the labeled specific binding pair member indicates the location of the complementary member of that specific binding pair; each specific binding pair member having an area on the surface or in a cavity which specifically binds to, and is complementary with, a particular spatial and polar organization of the other. Exemplary binding pairs are set forth in Table 2.

TABLE 2

Representative Specific Binding Pairs

| antigen | antibody |
|---|---|
| biotin | avidin (or streptavidin or anti-biotin) |
| IgG* | protein A or protein G |
| drug | drug receptor |
| folate | folate binding protein |
| toxin | toxin receptor |
| carbohydrate | lectin or carbohydrate receptor |
| peptide | peptide receptor |
| protein | protein receptor |
| enzyme substrate | enzyme |
| DNA (RNA) | cDNA (cRNA)† |
| hormone | hormone receptor |
| ion | chelator |
| antibody | antibody-binding proteins |

*IgG is an immunoglobulin
†cDNA and cRNA are the complementary strands used for hybridization In an exemplary embodiment, the present compounds of the invention are covalently bonded to a solid support. The solid support may be attached to the compound or through a reactive group, if present, or through a carrier molecule, if present. In exemplary embodiment, at least one member selected from $R^1$, $R^2$, $R^{11}$, or $R^{12}$ comprises a solid support. Preferably, at least one of $R^1$ or $R^{11}$ comprises a solid support or is attached to a solid support. Alternatively, if the present compound comprises a carrier molecule or reactive group a solid support may be covalently attached independently to those substituents, allowing for further conjugation to a another dye, carrier molecule or solid support.

A solid support suitable for use in the present invention is typically substantially insoluble in liquid phases. Solid supports of the current invention are not limited to a specific type of support. Rather, a large number of supports are available and are known to one of ordinary skill in the art. Thus, useful solid supports include solid and semi-solid matrixes, such as aerogels and hydrogels, resins, beads, biochips (including thin film coated biochips), microfluidic chip, a silicon chip, multi-well plates (also referred to as microtitre plates or microplates), membranes, conducting and nonconducting metals, glass (including microscope slides) and magnetic supports. More specific examples of useful solid supports include silica gels, polymeric membranes, particles, derivatized plastic films, glass beads, cotton, plastic beads, alumina gels, polysaccharides such as Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose, polyvinylchloride, polypropylene, polyethylene (including poly(ethylene glycol)), nylon, latex bead, magnetic bead, paramagnetic bead, superparamagnetic bead, starch and the like.

In some embodiments, the solid support may include a solid support reactive functional group, including, but not limited to, hydroxyl, carboxyl, amino, thiol, aldehyde, halogen, nitro, cyano, amido, urea, carbonate, carbamate, isocyanate, sulfone, sulfonate, sulfonamide, sulfoxide, etc., for attaching the compounds of the invention. Useful reactive groups are disclosed above and are equally applicable to the solid support reactive functional groups herein.

A suitable solid phase support can be selected on the basis of desired end use and suitability for various synthetic protocols. For example, where amide bond formation is desirable to attach the compounds of the invention to the solid support, resins generally useful in peptide synthesis may be employed, such as polystyrene (e.g., PAM-resin obtained from Bachem Inc., Peninsula Laboratories, etc.), POLYHIPE™ resin (obtained from Aminotech, Canada), polyamide resin (obtained from Peninsula Laboratories), polystyrene resin grafted with polyethylene glycol (TentaGel™, Rapp Polymere, Tubingen, Germany), polydimethyl-acrylamide resin (available from Milligen/Biosearch, California), or PEGA beads (obtained from Polymer Laboratories).

Preparation of Conjugates

Conjugates of components (carrier molecules and solid supports), e.g., drugs, peptides, toxins, nucleotides, phospholipids and other organic molecules are prepared by organic synthesis methods using the reactive dyes, are generally prepared by means well recognized in the art (Haugland, MOLECULAR PROBES HANDBOOK, supra, 2002). Conjugation to form a covalent bond may consist of simply mixing the reactive dyes of the present invention in a suitable solvent in which both the reactive compound and the substance to be conjugated are soluble. The reaction preferably proceeds spontaneously without added reagents at room temperature or below. For those reactive dyes that are photoactivated, conjugation is facilitated by illumination of the reaction mixture to activate the reactive dye. Chemical modification of water-insoluble substances, so that a desired dye-conjugate may be prepared, is preferably performed in an aprotic solvent such as dimethylformamide (DMF), dimethylsulfoxide (DMSO), acetone, ethyl acetate, toluene, or chloroform.

Preparation of peptide or protein conjugates typically comprises first dissolving the protein to be conjugated in aqueous buffer at about 1-10 mg/mL at room temperature or below. Bicarbonate buffers (pH about 8.3) are especially suitable for reaction with succinimidyl esters, phosphate buffers (pH about 7.2-8) for reaction with thiol-reactive functional groups and carbonate or borate buffers (pH about 9) for reaction with isothiocyanates and dichlorotriazines. The appropriate reactive dye is then dissolved in a nonhydroxylic solvent (usually DMSO or DMF) in an amount sufficient to give a suitable degree of conjugation when added to a solution of the protein to be conjugated. The appropriate amount of compound for any protein or other component is conveniently predetermined by experimentation in which variable amounts of the dye are added to the protein, the conjugate is chromatographically purified to separate unconjugated compound and the compound-protein conjugate is tested in its desired application.

Following addition of the reactive compound to the component solution, the mixture may be incubated for a suitable period (typically about 1 hour at room temperature to several hours on ice), the excess unreacted compound is removed by gel filtration, dialysis, HPLC, adsorption on an ion exchange or hydrophobic polymer or other suitable means. The conjugate is used in solution or lyophilized. In this way, suitable conjugates can be prepared from antibodies, antibody fragments, avidins, lectins, enzymes, proteins A and G, cellular proteins, albumins, histones, growth factors, hormones, and other proteins. The approximate degree of substitution is determined from the long wavelength absorption of the compound-protein conjugate by using the extinction coefficient of the un-reacted compound at its long wavelength absorption peak, the unmodified protein's absorption peak in the ultraviolet and by correcting the UV absorption of the conjugate for absorption by the compound in the UV.

Conjugates of polymers, including biopolymers and other higher molecular weight polymers are typically prepared by means well recognized in the art (for example, Brinkley et al., *Bioconjugate Chem.*, 3: 2 (1992)). In these embodiments, a single type of reactive site may be available, as is typical for polysaccharides or multiple types of reactive sites (e.g. amines, thiols, alcohols, phenols) may be available, as is typical for proteins. Selectivity of labeling is best obtained by selection of an appropriate reactive dye. For example, modification of thiols with a thiol-selective reagent such as a haloacetamide or maleimide, or modification of amines with an amine-reactive reagent such as an activated ester, acyl azide, isothiocyanate or 3,5-dichloro-2,4,6-triazine. Partial selectivity can also be obtained by careful control of the reaction conditions.

When modifying polymers with the compounds, an excess of the compound is typically used, relative to the expected degree of dye substitution. Any residual, un-reacted compound or hydrolysis product is typically removed by dialysis, chromatography or precipitation. Presence of residual, unconjugated compound can be detected by thin layer chromatography using a solvent that elutes the compound away from its conjugate. In all cases it is usually preferred that the reagents be kept as concentrated as practical so as to obtain adequate rates of conjugation.

In an exemplary embodiment, the conjugate is associated with an additional substance that binds either to the compound or the labeled component through noncovalent interaction. In another exemplary embodiment, the additional substance is an antibody, an enzyme, a hapten, a lectin, a receptor, an oligonucleotide, a nucleic acid, a liposome, or a polymer. The additional substance is optionally used to probe for the location of the conjugate, for example, as a means of enhancing the signal of the conjugate.

Methods of Use

The present nucleic acid reporter molecules may be utilized without limit for the fluorescent detection of nucleic acid polymers in a test sample. The methods for the detection of single, double, triple or quadruple stranded DNA and RNA or a combination thereof comprises contacting a sample with a present nucleic acid reporter molecule to prepare a labeling mixture, incubating the sample with the staining solution for a sufficient amount of time for the present reporter molecules to complex with the nucleic acid, illuminating the sample with an appropriate wavelength and observing the illuminated labeling mixture whereby the nucleic acid polymer is detected.

The compound is typically combined with the sample as a staining solution. The staining solution is typically prepared by dissolving a present nucleic acid reporter molecule in an aqueous solvent such as water, a buffer solution or assay solution, such as phosphate buffered saline, or an organic solvent such as dimethylsulfoxide (DMSO), dimethylformamide (DMF), methanol, ethanol or acetonitrile. Typically, the present nucleic reporter molecules are first dissolved in an organic solvent such as DMSO as a stock solution. The stock solution is typically prepared about 100-300× more concentrated that the effective working concentration. Thus, the stock solution is diluted to an effective working concentration in an aqueous solution that optionally includes appropriate buffering components and a detergent. An effective working concentration of the present compounds is the amount sufficient to give a detectable optical response when complexed with nucleic acid polymers. Typically, the effective amount is about 10 nM to 10 µM. Most preferred is about 20 nM to 1 µM. For selected reporter compounds, staining is optimal when the staining solution has a concentration of about 0.04 µM to about 0.1 µM. It is generally understood that the specific amount of the nucleic acid reporter molecules present in a staining solution is determined by the physical nature of the sample and the nature of the analysis being performed.

In an exemplary embodiment, the staining solution contains a detergent. This is particularly useful when the nucleic acid is present in an aqueous sample solution. Without wishing to be bound by a theory it appears that a low concentration of detergent stabilizes the present nucleic acid reporter molecule when present in solution. Thus the staining solution can be combined with an aqueous sample providing an optimized solution based detection assay. Detergents include, but are not limited to, CHAPS, Triton-X, SDS and Tween 20. The detergent is typically present in an aqueous solution at a concentration from about 0.0001% to about 0.2% (w/v). More specifically the detergent is present from about 0.0015% to about 0.005% (w/v). In an exemplary embodiment a staining solution comprises a present nucleic acid reporter molecule present at about 0.04 µM and the detergent CHAPS present at about 0.0025% (w/v).

In a further embodiment, the present staining solution contains an agent to reduce the signal to noise ratio. Such an agent improves the linearity of the curve obtained from a range of nucleic acid concentrations. Thus, in an exemplary embodiment, a staining solution for detecting RNA in the presence of DNA, contains a low concentration of DNA. Without wishing to be bound by a theory it appears that this low concentration associates with the present reporter molecules, which do not fluoresce, and lowers the background fluorescent signal. Preferably this DNA is double stranded and in one aspect the DNA is lambda DNA. Thus, in one embodiment, the present staining solution contains DNA in a concentration from about 1.0 µg/ml to about 0.05 µg/ml. More specifically the DNA is present about 0.05 µg/ml to about 0.01 µg/ml. Therefore, in an exemplary embodiment a present staining solution comprises a present nucleic acid reporter molecule present at about 0.04 µM and DNA at a concentration of about 0.2 µg/ml. In a further embodiment this staining solution would also include a detergent, as disclosed above.

Therefore, the present disclosure provides a staining solution that comprises a present nucleic acid reporter molecule in a buffer solution. In a further embodiment this staining solution comprises a detergent and in yet a further embodiment, the staining solution also comprises a low concentration of DNA.

The sample may be combined with the staining solution by any means that facilitates contact between the nucleic acid reporter molecules and the nucleic acid. The contact can occur through simple mixing, as in the case where the sample is a solution. The present reporter molecules may be added to the nucleic acid solution directly or may contact the solution on an inert matrix such as a blot or gel, a testing strip, a microarray, or any other solid or semi-solid surface, for example where only a simple and visible demonstration of the presence of nucleic acids is desired. Any inert matrix used to separate the sample can be used to detect the presence of nucleic acids by observing the fluorescent response on the inert matrix.

Thus, in one embodiment is provided a composition comprising a sample and a present nucleic acid reporter molecule. In one aspect this composition is an aqueous solution.

Alternatively, the sample may include cells and/or cell membranes. While selected examples of the compound disclosed herein may permeate cellular membranes rapidly and completely upon addition of the staining solution, any technique that is suitable for transporting the reporter molecules across cell membranes with minimal disruption of the viability of the cell and integrity of cell membranes is a valid method of combining the sample with the present reporter molecules for detection of intracellular nucleic acid. Examples of suitable processes include action of chemical agents such as detergents, enzymes or adenosine triphosphate; receptor- or transport protein-mediated uptake; pore-forming proteins; microinjection; electroporation; hypoosmotic shock; or minimal physical disruption such as scrape loading or bombardment with solid particles coated with or in the presence of the present reporter molecules.

The sample is incubated in the presence of the nucleic acid reporter molecules for a time sufficient to form the fluorescent nucleic acid-reporter molecule complex. Detectable fluorescence in a solution of nucleic acids is essentially instantaneous. Detectable fluorescence within cell membranes requires the permeation of the dye into the cell. While most present nucleic acid reporter molecules are not cell permeant due to the presence of at least one negatively charged moiety, it is envisioned that the present compounds could be adequately substituted to provide cell permeant versions of the present compounds. In general, visibly detectable fluorescence can be obtained in a wide variety of cells with certain cell permeant embodiments of the present invention within about 10-30 minutes after combination with the sample, commonly within about 10-20 minutes. While permeation and fluorescence should be rapid for all reporter molecules comprising an aromatic substituent on the pyridinium or quinolinium moiety of the D moiety, it is readily apparent to one skilled in the art that the time necessary for sufficient permeation of the dye, or sufficient formation of the fluorescent nucleic acid complex, is dependent upon the physical and chemical nature of the individual sample and the sample medium.

In another embodiment, is provided a complex comprising a present nucleic acid reporter molecule and a nucleic acid polymer. To facilitate the detection of the nucleic acid-reporter molecule complex, the excitation or emission properties of the fluorescent complex are utilized. For example, the sample is excited by a light source capable of producing light at or near the wavelength of maximum absorption of the fluorescent complex, such as an ultraviolet or visible lamp, an arc lamp, a laser, or even sunlight. Preferably the fluorescent complex is excited at a wavelength equal to or greater than about 300 nm, more preferably equal to or greater than about 340 nm. The fluorescence of the complex is detected qualitatively or quantitatively by detection of the resultant light emission at a wavelength of greater than about 400 nm, more preferably greater than about 450 nm, most preferred greater than 480 nm. The emission is detected by means that include visible inspection, photographic film, or the use of current instrumentation such as fluorometers, quantum counters, plate readers, epifluorescence microscopes and flow cytometers or by means for amplifying the signal such as a photomultiplier.

In an exemplified embodiment, the present nucleic acid reporter compounds are used to detect RNA in the presence of DNA, wherein the method comprises the following steps:
a. combining a present nucleic acid reporter molecule with a sample to prepare a labeling mixture, wherein the nucleic acid reporter molecule has a RNA/DNA ratio of fluorescence enhancement greater than about one;
b. incubating the labeling mixture for a sufficient amount of time for the nucleic acid reporter molecule to associate with RNA in the sample to form an incubated mixture;
c. illuminating the incubated mixture with an appropriate wavelength to form an illuminated mixture; and,
d. observing the illuminated mixture whereby the RNA is detected in the presence of DNA.

Typically, the fluorescence of the RNA complex is distinguishable from the fluorescence of a DNA complex with the compound. This difference may be due to any detectable optical property, but in one embodiment, the fluorescence of the RNA complex is brighter than the fluorescence of a corresponding DNA complex with the compound. Therefore, in an exemplary embodiment, by comparing the fluorescence response of the RNA complex with a standard, the amount of RNA in the sample may be quantitated, even in the presence of DNA.

As discussed above, the RNA present in the sample may be present in a solution, or in or on a solid or semisolid support. In a preferred embodiment, the nucleic acid is present in an aqueous solution. The detection of RNA in solution may also be enhanced by the addition of a detergent to the staining solution. Exemplified detergents include, but are not limited to CHAPS, Triton-X, SDS and Tween 20. Particularly preferred is CHAPS, wherein the fluorescent single in an aqueous signal is stabilized for at least 6 hours. The detection of RNA in a solution may also be further enhanced by the addition of a low concentration of DNA to the staining solution.

Typically, the fluorescence of the RNA complex is distinguishable from the fluorescence of a DNA complex with the compound by fluorescence intensity. This difference may be due to any detectable optical property, but in one embodiment, the fluorescence of the RNA complex is brighter than the fluorescence of a corresponding DNA complex with the compound.

By comparing the fluorescence response of the RNA complex with a standard, the amount of RNA in the sample may be quantitated, even in the presence of DNA.

As discussed above, the RNA present in the sample may be present in a solution, or in or on a solid or semisolid support. The RNA itself may be selected from one or more of mRNA, tRNA, and rRNA.

The method may also be enhanced by the addition of an additional detection reagent that exhibits a greater fluorescence response when associated with DNA than when associated with RNA. A variety of nucleic acid stains that fluoresce brightly when complexed with DNA are known in the art.

The present nucleic acid reporter molecules that are capable of producing a fluorescent intensity signal that is greater on RNA than on DNA are determined empirically. The relative selectivity of the present compounds for differentiating RNA and DNA may be readily evaluated as set out in Examples 2, and 6-12.

The foregoing methods having been described it is understood that the many and varied compounds of the present invention can be utilized with the many methods. The compounds not being limited to just those that are specifically disclosed.

In an exemplary embodiment the present methods employ a nucleic acid reporter molecule that comprises the formula

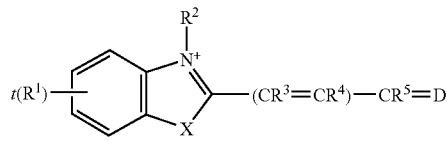

Formula I wherein at least one of $R^3$, $R^4$, and $R^5$ is an alkyl, substituted alkyl, a 5-, 6- or 7-membered heterocycloalkyl, a substituted 5-, 6- or 7-membered heterocycloalkyl, a 5-, 6- or 7-membered cycloalkyl, a substituted 5-, 6- or 7-membered cycloalkyl, a 5-, 6- or 7-membered heteroaryl, a substituted 5-, 6- or 7-membered heteroaryl, a 5-, 6- or 7-membered aryl or a substituted 5-, 6- or 7-membered aryl; and the remaining $R^3$, $R^4$ or $R^5$ are hydrogen.

In an exemplary embodiment at least one of $R^3$, $R^4$, and $R^5$ is a substituted alkyl, a substituted 5-, 6- or 7-membered heterocycloalkyl, a substituted 5-, 6- or 7-membered cycloalkyl, a substituted 5-, 6- or 7-membered heteroaryl, or a substituted 5-, 6- or 7-membered aryl that is substituted by an alkyl, $-(CH_2)_k-NR^6R^7$; $-COOR^8$, $NO_2$, or halogen, wherein k is an integer from 0 to about 6. The substituents $R^6$, $R^7$ and $R^8$ are independently hydrogen, alkyl, substituted alkyl, alkoxy, substituted alkoxy, sulfoalkyl or aminoalkyl. In one aspect at least one of $R^3$ and $R^4$ is a thiophenyl, substituted thiophenyl, adamantyl, substituted adamantly, phenyl, substituted phenyl, alkyl, substituted alkyl, benzyl or substituted benzyl.

These nucleic acid reporter molecules exhibit a fluorescence enhancement when non-covalently associated with a nucleic acid molecule. In one aspect, the fluorescence enhancement is greater when the nucleic acid is RNA than when the nucleic acid is DNA. In another aspect, the fluorescence enhancement is greater when the nucleic acid is DNA than when the nucleic acid is RNA.

The $R^1$ substituent is independently hydrogen, carboxy, sulfo, phosphate, phosphonate, amino, hydroxyl, trifluoromethyl, halogen, alkyl, substituted alkyl, alkoxy, substituted alkoxy, alkylamino, substituted alkylamino, dialkylamino, substituted dialkylamino, aminoalkyl, substituted aminoalkyl, fused benzene, substituted fused benzene, reactive group, solid support or carrier molecule and t is an integer from 1 to 4. In one aspect $R^1$ is alkoxy or halogen. In another aspect $R^1$ is methoxy, Br, Cl, or F.

The $R^2$ substituent is an alkyl, substituted alkyl, arylalkyl, substituted arylalkyl, heteroalkyl, substituted heteroalkyl, alkoxy, substituted alkoxy, carboxy, carboxyalkyl, hydroxy, hydroxyalkyl, sulfo, sulfoalkyl, amino, aminoalkyl, alkylamino, dialkylamino, or trialkylammonium. In one aspect $R^2$ is methyl, ethyl, propyl, or $-(CH_2)_3SO_3^-$.

X is O, S or Se.

The D is a substituted pyridinium, unsubstituted pyridinium, substituted quinolinium, unsubstituted quinolinium, substituted benzazolium or unsubstituted benzazolium moiety. In an exemplary embodiment, D has the formula:

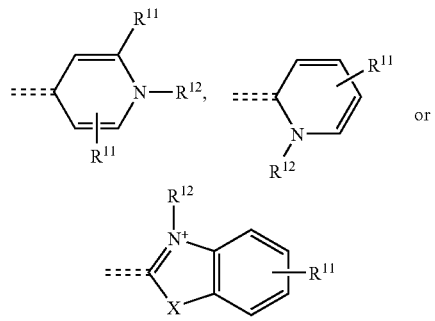

wherein $R^{11}$ is hydrogen, substituted alkyl, unsubstituted alkyl, substituted heteroalkyl, unsubstituted heteroalkyl, substituted aryl, unsubstituted aryl, substituted arylalkyl, unsubstituted arylalkyl, substituted heteroarylalkyl; unsubstituted heteroarylalkyl, substituted heteroaryl, unsubstituted heteroaryl substituted cycloalkyl, unsubstituted cycloalkyl, substituted heterocycloalkyl, unsubstituted heterocycloalkyl, halogen, alkoxy, substituted alkylamino, unsubstituted alkylamino, substituted alkylthio, unsubstituted alkylthio, reactive group, solid support, or carrier molecule and $R^{12}$ is an alkyl, substituted alkyl, arylalkyl, substituted arylalkyl, heteroalkyl, substituted heteroalkyl, alkoxy, substituted alkoxy, carboxy, carboxyalkyl, hydroxy, hydroxyalkyl, sulfo, sulfoalkyl, amino, aminoalkyl, alkylamino, dialkylamino, or trialkylammonium. Alternatively, $R^{11}$ in combination with an adjacent $R^{11}$ or $R^{12}$, together with the atoms to which they are joined, form a ring which is a 5-, 6- or 7-membered heterocycloalkyl, a substituted 5-, 6- or 7-membered heterocycloalkyl, a 5-, 6- or 7-membered cycloalkyl, a substituted 5-, 6- or 7-membered cycloalkyl, a 5-, 6- or 7-membered heteroaryl, a substituted 5-, 6- or 7-membered heteroaryl, a 5-, 6- or 7-membered aryl or a substituted 5-, 6- or 7-membered aryl.

In an exemplary embodiment of the methods, the nucleic acid reporter molecule has the formula:

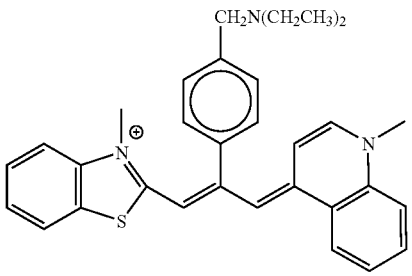

or the formula

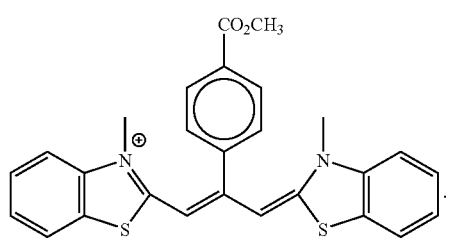

In an exemplary embodiment, the nucleic aid reporter molecule of the present methods comprise a reactive group, solid support and carrier molecule wherein these substituents independently comprise a linker that is a single covalent bond, or a covalent linkage that is linear or branched, cyclic or heterocyclic, saturated or unsaturated, having 1-20 nonhydrogen atoms selected from the group consisting of C, N, P, O and S; and are composed of any combination of ether, thioether, amine, ester, carboxamide, sulfonamide, hydrazide bonds and aromatic or heteroaromatic bonds.

In an exemplary embodiment, the reactive group is an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, an imido ester, an isocyanate, an isothiocyanate, a maleimide, a phosphoramidite, a reactive platinum complex, a silyl halide, a sulfonyl halide, a thiol or a photoactivatable group. In a further aspect, the reactive group is carboxylic acid, succinimidyl ester of a carboxylic acid, hydrazide, amine or a maleimide.

In an exemplary embodiment the carrier molecule is an amino acid, a peptide, a protein, a polysaccharide, a nucleoside, a nucleotide, an oligonucleotide, a nucleic acid polymer, a hapten, a psoralen, a drug, a hormone, a lipid, a lipid assembly, a synthetic polymer, a polymeric microparticle, a biological cell or a virus. In a further aspect, the carrier molecule is an antibody or fragment thereof, an avidin or streptavidin, a biotin, a blood component protein, a dextran, an enzyme, an enzyme inhibitor, a hormone, an IgG binding protein, a fluorescent protein, a growth factor, a lectin, a lipopolysaccharide, a microorganism, a metal binding protein, a metal chelating moiety, a non-biological microparticle, a peptide toxin, a phosphotidylserine-binding protein, a structural protein, a small-molecule drug, or a tyramide.

In an exemplary embodiment, the solid support is a microfluidic chip, a silicon chip, a microscope slide, a microplate well, silica gels, polymeric membranes, particles, derivatized plastic films, glass beads, cotton, plastic beads, alumina gels, polysaccharides, polyvinylchloride, polypropylene, polyethylene, nylon, latex bead, magnetic bead, paramagnetic bead, or superparamagnetic bead. In a further aspect, the solid support is Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose or starch.

Sample Preparation

The sample may be prepared using methods well known in the art for isolating nucleic acid for in vitro and solution based assay detection or well know methods for live cell or fixed cells for intracellular and/or in vivo detection of nucleic acids. The sample includes, without limitation, any biological derived material that is thought to contain a nucleic acid polymer. Alternatively, samples also include material that nucleic acid polymers have been added to such as a PCR reaction mixture, a polymer gel such as agarose or polyacrylamide gels or a microfluidic assay system. In another aspect of the present disclosure, the sample can also include a buffer solution that contains nucleic acid polymers to determine the present reporter molecules that are ideal under different assay conditions or to determine the present reporter molecules that are preferential RNA reporters.

The sample can be a biological fluid such as whole blood, plasma, serum, nasal secretions, sputum, saliva, urine, sweat, transdermal exudates, cerebrospinal fluid, or the like. Biological fluids also include tissue and cell culture medium wherein an analyte of interest has been secreted into the medium. Alternatively, the sample may be whole organs, tissue or cells from the animal. Examples of sources of such samples include muscle, eye, skin, gonads, lymph nodes, heart, brain, lung, liver, kidney, spleen, thymus, pancreas, solid tumors, macrophages, mammary glands, mesothelium, and the like. Cells include without limitation prokaryotic cells such as bacteria, yeast, fungi, mycobacteria and mycoplasma, and eukaryotic cells such as nucleated plant and animal cells that include primary cultures and immortalized cell lines. Typically prokaryotic cells include *E. coli* and *S. aureus*. Eukaryotic cells include without limitation ovary cells, epithelial cells, circulating immune cells, β cells, hepatocytes, and neurons.

In an exemplary embodiment, the sample comprises biological fluids, buffer solutions, live cells, fixed cells, eukaryotic cells, prokaryotic cells, nucleic acid polymers, nucleosides, nucleotides, a polymeric gel or tissue sections. In a further aspect, the sample comprises nucleic acid polymers in an aqueous buffer.

The nucleic acid may be either natural (biological in origin) or synthetic (prepared artificially). The nucleic acid may be present as nucleic acid fragments, oligonucleotides, or nucleic acid polymers. The nucleic acid may be present in a condensed phase, such as a chromosome. The presence of the nucleic acid in the sample may be due to a successful or unsuccessful experimental methodology, undesirable contamination, or a disease state. Nucleic acid may be present in all, or only part, of a sample, and the presence of nucleic acids may be used to distinguish between individual samples, or to differentiate a portion or region within a single sample.

The nucleic acid may be enclosed in a biological structure, for example contained within a viral particle, an organelle, or within a cell. The nucleic acids enclosed in biological structures may be obtained from a wide variety of environments, including cultured cells, organisms or tissues, unfiltered or separated biological fluids such as urine, cerebrospinal fluid, blood, lymph fluids, tissue homogenate, mucous, saliva, stool, or physiological secretions or environmental samples such as soil, water and air. The nucleic acid may be endogenous or introduced as foreign material, such as by infection or by transfection. The present nucleic acid reporter molecules can also be used for staining nucleic acids in a cell or cells that is fixed and treated with routine histochemical or cytochemical procedures.

Alternatively, the nucleic acid is not enclosed within a biological structure, but is present as a sample solution. The sample solution can vary from one of purified nucleic acids to crude mixtures such as cell extracts, biological fluids and environmental samples. In some cases it is desirable to separate the nucleic acids from a mixture of biomolecules or fluids in the solution prior to combination with the present reporter molecules. Numerous, well known, techniques exist for separation and purification of nucleic acids from generally crude mixtures with other proteins or other biological molecules. These include such means as electrophoretic techniques and chromatographic techniques using a variety of supports.

The sample may be incubated in the presence of the nucleic acid reporter molecules for a time sufficient to form a nucleic acid-reporter molecule complex. While permeation and complexation may be more or less rapid for the compounds disclosed herein, largely depending on the nature of the substituents present on the compound. It should be apparent to one skilled in the art that the time necessary for sufficient permeation of the dye, or sufficient formation of the resulting nucleic acid complex, is dependent upon the physical and chemical nature of the individual sample and the sample medium (see for example U.S. Pat. No. 5,658,751).

Illumination

The sample containing a nucleic acid-reporter molecule complex may be illuminated with a wavelength of light selected to give a detectable optical response, and observed with a means for detecting the optical response. By optical response is meant any detectable colorimetric or luminescent property of the complex. Typically, the optical response is related to the excitation or emission properties of the complex.

For example, the sample may be excited by a light source capable of producing light at or near the wavelength of maximum absorption of the fluorescent complex, such as an ultraviolet or visible lamp, an arc lamp, a laser, or even sunlight. The optical response is optionally detected by visual inspection, or by use of any of the following devices: CCD camera, video camera, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, examination of the sample optionally includes sorting portions of the sample according to their fluorescence response.

The wavelengths of the excitation and emission bands of the nucleic acid reporter molecules vary with reporter molecule composition to encompass a wide range of illumination and detection bands. This allows the selection of individual reporter molecules for use with a specific excitation source or detection filter. In particular, present reporter molecules can be selected that possess excellent correspondence of their excitation band with the 633/647 nm band of the commonly used argon-ion laser or emission bands which are coincident with preexisting filters.

The presence, location, and distribution of nucleic acid, particularly RNA, may be detected using the spectral properties of the compound-nucleic acid complex. Once the dye-nucleic acid complex is formed, its presence may be detected and used as an indicator of the presence, location, or type of nucleic acids in the sample, or as a basis for sorting cells, or as a key to characterizing the sample or cells in the sample. Such characterization may be enhanced by the use of additional reagents, including fluorescent reagents. The nucleic acid concentration in a sample can also be quantified by comparison with known relationships between the fluorescence of the nucleic acid-dye complex and concentration of nucleic acids in the sample. In particular, fluorescence intensity may be compared to a standard curve prepared from samples containing known nucleic acid concentrations, particularly RNA concentrations.

Kits

Suitable kits for forming a nucleic acid-reporter molecule complex and detecting the nucleic acid also form part of the present disclosure. Such kits can be prepared from readily available materials and reagents and can come in a variety of embodiments. The contents of the kit will depend on the design of the assay protocol or reagent for detection or measurement. All kits will contain instructions, appropriate reagents, and one or more of the presently disclosed nucleic acid reporter molecules. Typically, instructions include a tangible expression describing the reagent concentration or at least one assay method parameter such as the relative amounts of reagent and sample to be added together, maintenance time periods for reagent/sample admixtures, temperature, buffer conditions and the like to allow the user to carry out any one of the methods or preparations described above. In one aspect, the kit is formulated to facilitate the high-throughput screening of multiple samples, such as may be accomplished using automated methods.

Thus, a kit for detecting nucleic acid in a sample may comprise a compound as described above. The kit may further include instructions for performing one or more of the above disclosed methods, including the detection and/or quantitation of RNA in the presence of DNA.

The kit may optionally further include one or more of the following; sample preparation reagents, a buffering agent, a nucleic acid reporter molecule dilution buffer, an organic solvent or an additional detection reagent, particularly where the additional detection reagent is an additional distinct nucleic acid reporter molecule. Where the additional nucleic acid reporter is a DNA-selective nucleic acid stain, the kit may be useful for detecting and/or quantitating RNA in the presence of DNA. In one aspect the dilution buffer (for the present reporter molecules) comprises a detergent and/or a low concentration of DNA.

In an exemplary embodiment the present kits comprise a nucleic acid reporter molecule that comprises the formula Formula I

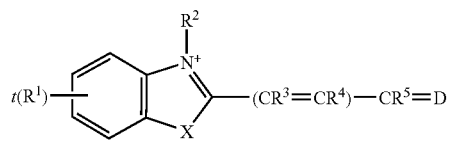

wherein at least one of $R^3$, $R^4$, and $R^5$ is an alkyl, substituted alkyl, a 5-, 6- or 7-membered heterocycloalkyl, a substituted 5-, 6- or 7-membered heterocycloalkyl, a 5-, 6- or 7-membered cycloalkyl, a substituted 5-, 6- or 7-membered cycloalkyl, a 5-, 6- or 7-membered heteroaryl, a substituted 5-, 6- or 7-membered heteroaryl, a 5-, 6- or 7-membered aryl or a substituted 5-, 6- or 7-membered aryl; and the remaining $R^3$, $R^4$ or $R^5$ are hydrogen.

In an exemplary embodiment at least one of $R^3$, $R^4$, and $R^5$ is a substituted alkyl, a substituted 5-, 6- or 7-membered heterocycloalkyl, a substituted 5-, 6- or 7-membered cycloalkyl, a substituted 5-, 6- or 7-membered heteroaryl, or a substituted 5-, 6- or 7-membered aryl that is substituted by an alkyl, $—(CH_2)_k—NR^6R^7$; $—COOR^8$, $NO_2$, or halogen, wherein k is an integer from 0 to about 6. The substituents $R^6$, $R^7$ and $R^8$ are independently hydrogen, alkyl, substituted alkyl, alkoxy, substituted alkoxy, sulfoalkyl or aminoalkyl. In one aspect at least one of $R^3$ and $R^4$ is a thiophenyl, substituted thiophenyl, adamantyl, substituted adamantly, phenyl, substituted phenyl, alkyl, substituted alkyl, benzyl or substituted benzyl.

These nucleic acid reporter molecules exhibit a fluorescence enhancement when non-covalently associated with a nucleic acid molecule. In one aspect, the fluorescence enhancement is greater when the nucleic acid is RNA than when the nucleic acid is DNA. In another aspect, the fluorescence enhancement is greater when the nucleic acid is DNA than when the nucleic acid is RNA.

The R¹ substituent is independently hydrogen, carboxy, sulfo, phosphate, phosphonate, amino, hydroxyl, trifluoromethyl, halogen, alkyl, substituted alkyl, alkoxy, substituted alkoxy, alkylamino, substituted alkylamino, dialkylamino, substituted dialkylamino, aminoalkyl, substituted aminoalkyl, fused benzene, substituted fused benzene, reactive group, solid support or carrier molecule and t is an integer from 1 to 4. In one aspect R¹ is alkoxy or halogen. In another aspect R¹ is methoxy, Br, Cl, or F.

The R² substituent is an alkyl, substituted alkyl, arylalkyl, substituted arylalkyl, heteroalkyl, substituted heteroalkyl, alkoxy, substituted alkoxy, carboxy, carboxyalkyl, hydroxy, hydroxyalkyl, sulfo, sulfoalkyl, amino, aminoalkyl, alkylamino, dialkylamino, or trialkylammonium. In one aspect R² is methyl, ethyl, propyl, or $-(CH_2)_3SO_3^-$.

X is O, S or Se.

The D is a substituted pyridinium, unsubstituted pyridinium, substituted quinolinium, unsubstituted quinolinium, substituted benzazolium or unsubstituted benzazolium moiety. In an exemplary embodiment, D has the formula:

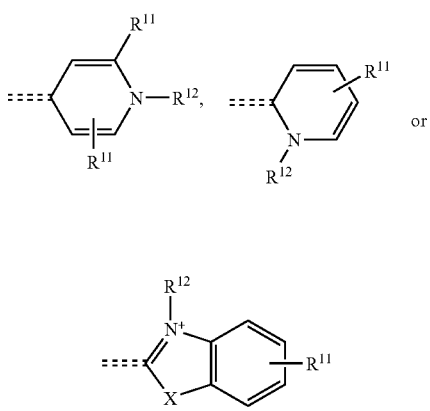

wherein $R^{11}$ is hydrogen, substituted alkyl, unsubstituted alkyl, substituted heteroalkyl, unsubstituted heteroalkyl, substituted aryl, unsubstituted aryl, substituted arylalkyl, unsubstituted arylalkyl, substituted heteroarylalkyl; unsubstituted heteroarylalkyl, substituted heteroaryl, unsubstituted heteroaryl substituted cycloalkyl, unsubstituted cycloalkyl, substituted heterocycloalkyl, unsubstituted heterocycloalkyl, halogen, alkoxy, substituted alkylamino, unsubstituted alkylamino, substituted alkylthio, unsubstituted alkylthio, reactive group, solid support, or carrier molecule and $R^{12}$ is an alkyl, substituted alkyl, arylalkyl, substituted arylalkyl, heteroalkyl, substituted heteroalkyl, alkoxy, substituted alkoxy, carboxy, carboxyalkyl, hydroxy, hydroxyalkyl, sulfo, sulfoalkyl, amino, aminoalkyl, alkylamino, dialkylamino, or trialkylammonium. Alternatively, $R^{11}$ in combination with an adjacent $R^{11}$ or $R^{12}$, together with the atoms to which they are joined, form a ring which is a 5-, 6- or 7-membered heterocycloalkyl, a substituted 5-, 6- or 7-membered heterocycloalkyl, a 5-, 6- or 7-membered cycloalkyl, a substituted 5-, 6- or 7-membered cycloalkyl, a 5-, 6- or 7-membered heteroaryl, a substituted 5-, 6- or 7-membered heteroaryl, a 5-, 6- or 7-membered aryl or a substituted 5-, 6- or 7-membered aryl.

In an exemplary embodiment of the kits, the nucleic acid reporter molecule has the formula:

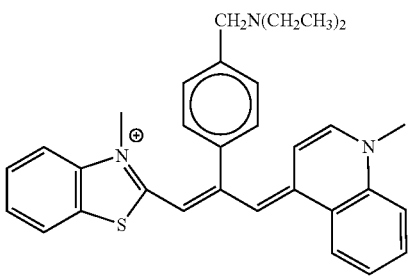

or the formula

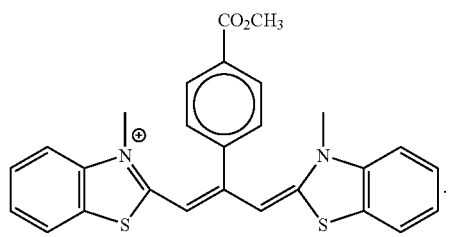

In an exemplary embodiment, the nucleic aid reporter molecule of the present kits comprise a reactive group, solid support and carrier molecule wherein these substituents independently comprise a linker that is a single covalent bond, or a covalent linkage that is linear or branched, cyclic or heterocyclic, saturated or unsaturated, having 1-20 nonhydrogen atoms selected from the group consisting of C, N, P, O and S; and are composed of any combination of ether, thioether, amine, ester, carboxamide, sulfonamide, hydrazide bonds and aromatic or heteroaromatic bonds.

In an exemplary embodiment, the reactive group is an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, an imido ester, an isocyanate, an isothiocyanate, a maleimide, a phosphoramidite, a reactive platinum complex, a silyl halide, a sulfonyl halide, a thiol or a photoactivatable group. In a further aspect, the reactive group is carboxylic acid, succinimidyl ester of a carboxylic acid, hydrazide, amine or a maleimide.

In an exemplary embodiment the carrier molecule is an amino acid, a peptide, a protein, a polysaccharide, a nucleoside, a nucleotide, an oligonucleotide, a nucleic acid polymer, a hapten, a psoralen, a drug, a hormone, a lipid, a lipid assembly, a synthetic polymer, a polymeric microparticle, a biological cell or a virus. In a further aspect, the carrier molecule is an antibody or fragment thereof, an avidin or streptavidin, a biotin, a blood component protein, a dextran, an enzyme, an enzyme inhibitor, a hormone, an IgG binding protein, a fluorescent protein, a growth factor, a lectin, a lipopolysaccharide, a microorganism, a metal binding protein, a metal chelating moiety, a non-biological microparticle, a peptide toxin, a phosphotidylserine-binding protein, a structural protein, a small-molecule drug, or a tyramide.

In an exemplary embodiment, the solid support is a microfluidic chip, a silicon chip, a microscope slide, a microplate well, silica gels, polymeric membranes, particles, derivatized plastic films, glass beads, cotton, plastic beads, alumina gels, polysaccharides, polyvinylchloride, polypropylene, polyethylene, nylon, latex bead, magnetic bead, paramagnetic bead, or superparamagnetic bead. In a further aspect, the solid support is Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose or starch.

A detailed description of the compounds and methods of the disclosure having been provided above, the following examples are given for the purpose of illustration, and shall not be construed as being a limitation on the scope of the invention or of the appended claims.

EXAMPLES

Example 1

Preparation of Compound 1 (2-(3-methyl-3H-benzothiazol-2-ylidene)-1-phenyl-ethanone)

A mixture of 0.58 g of 2,3-dimethylbenzothiazolium iodide and 0.42 g of benzoyl chloride in 20 mL of pyridine is heated at 60° C. for ten minutes. The pyridine is evaporated under reduced pressure and the residue is partitioned between chloroform and 1N HCl. Silica gel column with ethyl acetate hexane yields 0.25 g of Compound 1.

Compound 1

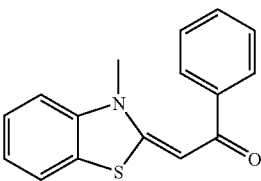

Other 2-(3-methyl-3H-benzothiazol-2-ylidene)-1-aryl/alkyl-ethanones may be prepared in an analogous fashion as Compound 1 with a corresponding acid chloride, as shown generally in the following synthetic scheme:

In particular, Compounds 2-16 may be prepared using the above synthetic strategy, among other compounds.

Compound 2

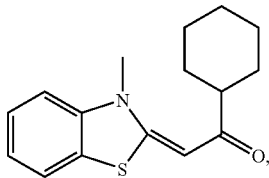

Compound 3

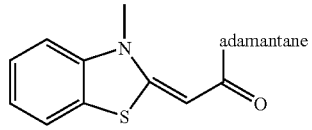

Compound 3

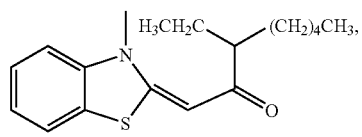

Compound 4

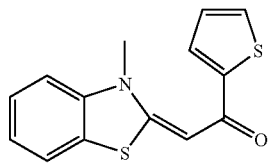

Compound 5

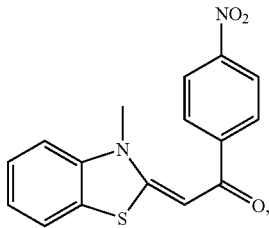

Compound 6

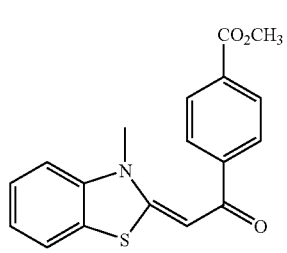

Compound 7

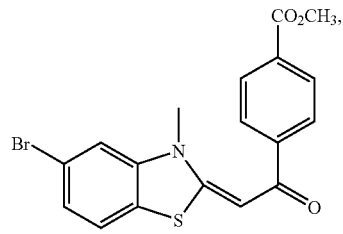

-continued

Compound 8

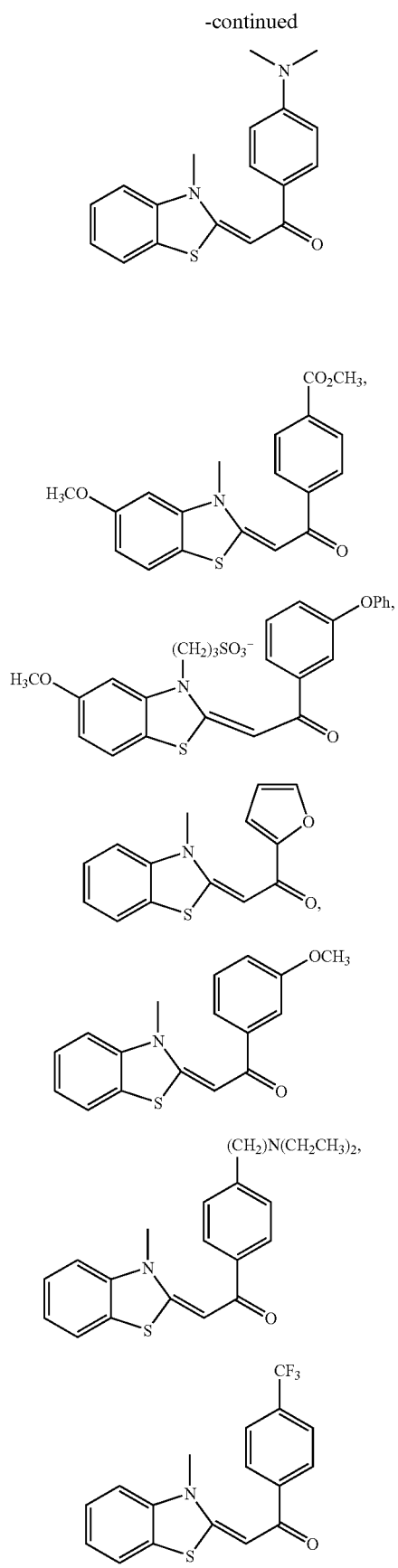

Compound 9

Compound 10

Compound 11

Compound 12

Compound 13

Compound 14

-continued

Compound 15

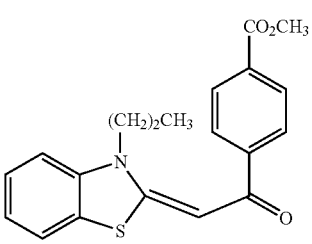

Example 2

Preparation of Compound 16

A mixture of 0.135 g of 2-(3-methyl-3H-benzothiazol-2-ylidene)-1-phenyl-ethanone and 0.15 mL of phosphorous oxychloride is stirred in 5 mL of dichloroethane at reflux for 2 hours. At the end of the period the dichloroethane is removed by evaporation and the residue is stirred in 30 mL of ethyl acetate and filtered to yield 0.16 g of the intermediate 2-(2-chloro-2-phenylvinyl)-3-methyl-benzothiazolium chloride, which is then reacted with 0.165 g of 1,4-dimethylquinolinium tosylate in 15 mL of methylene chloride in the presence of 0.14 g of triethylamine to generate the desired product.

Compound 16

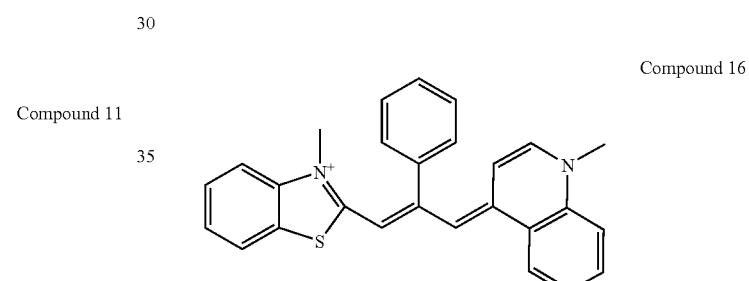

The following dye compounds (Compounds 17-46) are prepared in an analogous manner as Compound 16. The corresponding 2-(3-methyl-3H-benzothiazol-2-ylidene)-1-aryl/alkyl-ethanones are first treated with phosphorous oxychloride, and the resulting benzothiazolium chloride compound is then coupled with an appropriate quinolinium, pyridinium or benzazolium in the presence of an appropriate base (e.g. triethylamine) to generate Compounds 17-46. (See, Table 3)

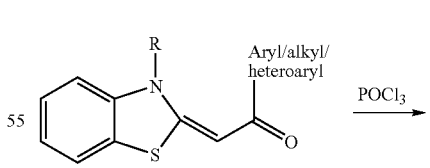

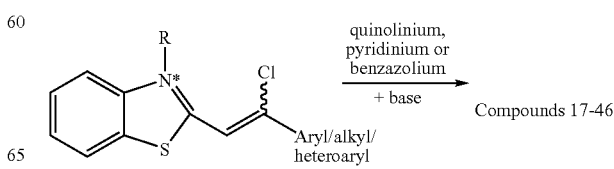

TABLE 3
| Compound | Ex/Em (nm)[1] | Fluorescence Enhancement Ratio (RNA/DNA)[2] |
|---|---|---|
| 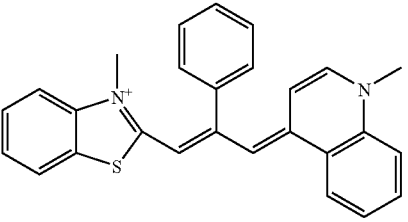  Compound 16 | 642/662 | 7 |
| 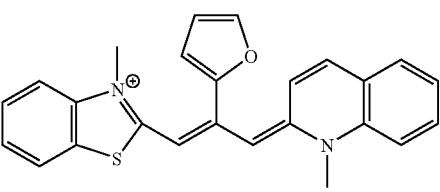  Compound 17 | 603/643 | 2.7 |
| 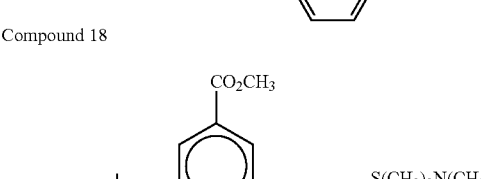  Compound 18 | 597/689 | 7.8 |
| 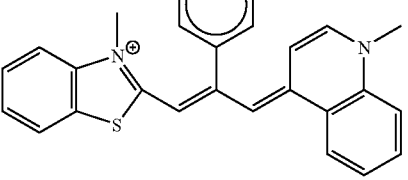  Compound 19 | 644/686 | 14.7 |
|   Compound 20 | 631/670 | 69 |

TABLE 3-continued

| Compound | Ex/Em (nm)[1] | Fluorescence Enhancement Ratio (RNA/DNA)[2] |
|---|---|---|
| Compound 21 | 557/598 | 6.6 |
| Compound 22 | 560/599 | 1.7 |
| Compound 23 | 557/590 | 4.2 |
| Compound 24 | 554/609 | 6.4 |
| Compound 25 | 573/618 | 1.9 |

TABLE 3-continued
| Compound | Ex/Em (nm)[1] | Fluorescence Enhancement Ratio (RNA/DNA)[2] |
|---|---|---|
| 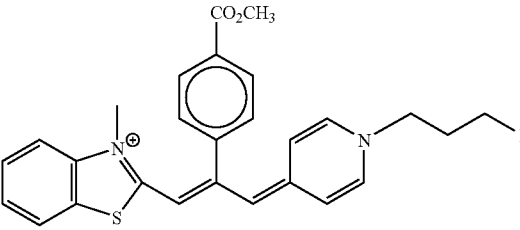<br>Compound 26 | 562/614 | 1.7 |
| 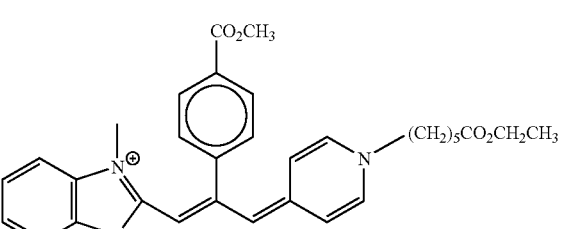<br>Compound 27 | | 1.67 |
| 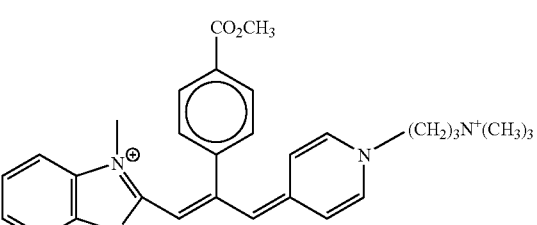<br>Compound 28 | | 2.16 |
| 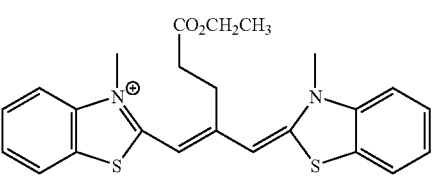<br>Compound 29 | 542/571 | 1.5 |
| 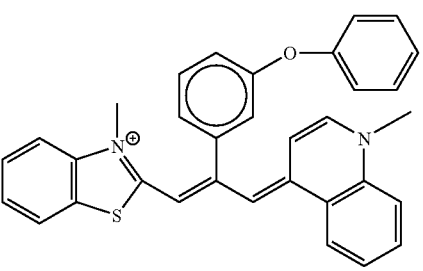<br>Compound 30 | 631/665 | 3.6 |
| 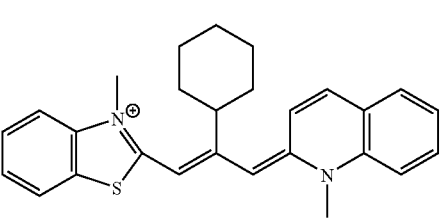<br>Compound 31 | 598/625 | 1.1 |

TABLE 3-continued

| Compound | Ex/Em (nm)[1] | Fluorescence Enhancement Ratio (RNA/DNA)[2] |
|---|---|---|
| Compound 32 | 600/630 | 2.9 |
| Compound 33 | 655/670 | 5.8 |
| Compound 34 | 605/630 | 11.1 |
| Compound 35 | 590/629 | 3.2 |
| Compound 36 | 640/670 | 6 |

TABLE 3-continued
| Compound | Ex/Em (nm)[1] | Fluorescence Enhancement Ratio (RNA/DNA)[2] |
|---|---|---|
| 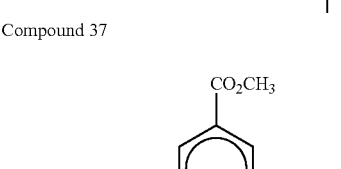<br>Compound 37 | 592/631 | 7.7 |
| <br>Compound 38 | 631/667 | 165 |
| <br>Compound 39 | 599/638 | 2.3 |
| 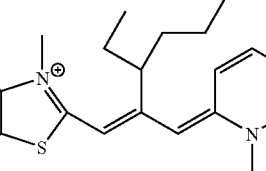<br>Compound 40 | 596/668 | 1.95 |
| 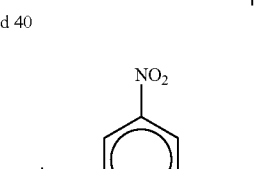<br>Compound 41 | 601/613 | 1.2 |

TABLE 3-continued
| Compound | Ex/Em (nm)[1] | Fluorescence Enhancement Ratio (RNA/DNA)[2] |
|---|---|---|
| 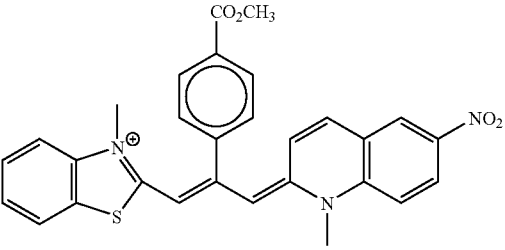<br>Compound 42 | 526/598 | 6 |
| 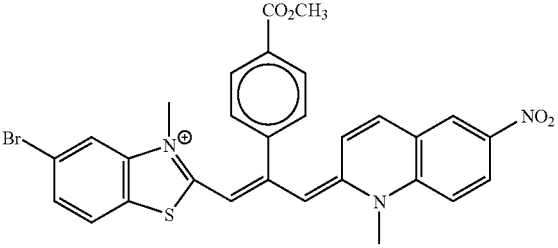<br>Compound 43 | 603/630 | 7 |
| 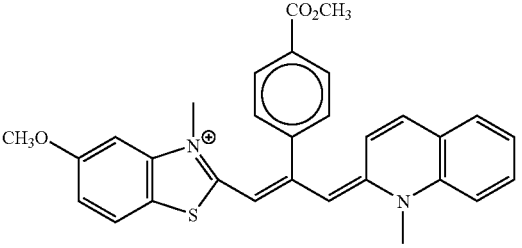<br>Compound 44 | 618/643 | 10 |
| 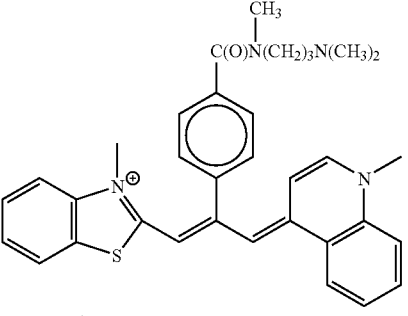<br>Compound 45 | 631/664 | 26.8 |
| 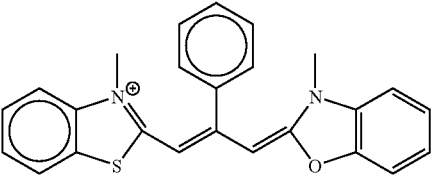<br>Compound 46 | 523/555 | 3 |
[1]Complex with nucleic acid
[2]The ratio of the fluorescence enhancement of the compound when associated with RNA to the fluorescence enhancement of the compound when associated with DNA

Example 3

Preparation of Compound 47

A mixture of 0.22 g of 2-(2-anilinovinyl)-3-methyl-benzthiazolium tosylate, 0.36 g of 4-benzyl-1-methylpyridinium tosylate, 0.1 mL of acetic anhydride and 0.2 mL of triethylamine is heated at 40° C. in 10 mL of dichloroethane for 3 hours. The crude product is then converted to the iodide salt and purified by recrystallization.

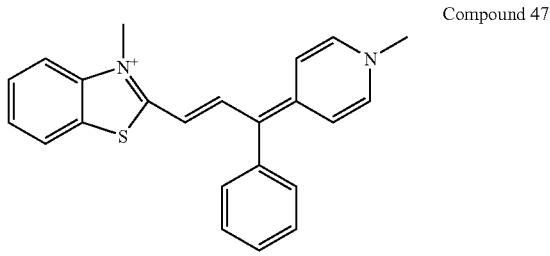

Compound 47

Example 4

Preparation of Compound 48

A mixture of 0.27 g of 2-(2-anilinovinyl)-3-methyl-benzthiazolium tosylate, 0.29 g of 4-ethyl-1-methylpyridinium tosylate, 0.1 mL of acetic anhydride and 0.2 mL of triethylamine is heated at 40° C. overnight. The solvent is removed by evaporation and the resulting residue is dissolved in 5 mL of methanol and added to a solution containing 3 g of sodium iodide in 50 mL of water. The product (Compound 48) is recovered via filtration.

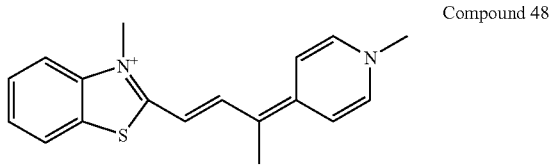

Compound 48

Example 5

Preparation of Compound 49

A mixture of 0.335 g of 2,3-dimethylbenzothiazolium tosylate and 0.182 g of trimethyl orthobenzoate is heated at reflux in 5 mL of pyridine for 6 hours. The solvent is removed by evaporation and the product (Compound 49) is isolated using silica gel column chromatography.

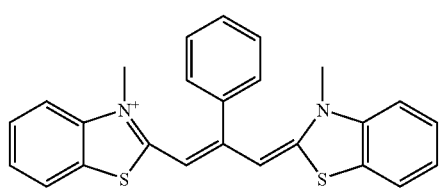

Compound 49

Example 6

Preparation of Compound 50

A mixture of 50 mg of Compound 20 and 0.5 mL of methyl iodide is heated in 3 mL of methanol in the presence of 0.01 mL of diisopropylethylamine at 50° C. for approximately 4 hours. The product (Compound 50) is recovered via filtration.

TABLE 4

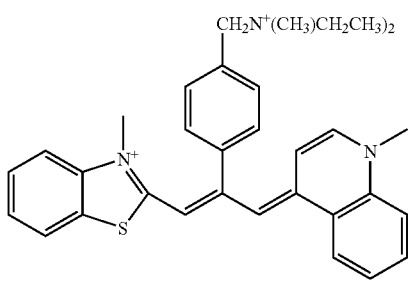

Compound 50

| Compound | Excitation/Emission (nm)[1] | Fluorescence Enhancement Ratio (RNA/DNA)[2] |
|---|---|---|
| 47 | 550/610 | 2.5 |
| 48 | 520/607 | 1.3 |
| 49 | 555/580 | 3.6 |
| 50 | 631/667 | 200 |

[1]Complex with nucleic acid
[2]The ratio of the fluorescence enhancement of the compound when associated with RNA to the fluorescence enhancement of the compound when associated with DNA

Example 7

Enhanced Fluorescence Emission of Compound 20 when Associated with rRNA vs DNA A stock solution of Compound 20 is made by dissolving about 0.1 to about 0.3 mg of the compound in 1 mL of DMF. The stock solution is then diluted in 10 mM TRIS, 1 mM EDTA (pH 7.2) with 20 µL of stock solution. This dilute solution exhibits an optical density (OD) of ~0.29562 and an extinction coefficient of 45,000, yielding a working concentration of ~1.3-3.8 µM. Compound 21, at a concentration of about 1.3-3.8 µM, is added to the test samples (1) rRNA and 2) DNA calf thymus. The RNA and DNA are present at a final concentration of about 104 µg/mL. After addition of the dye and the nucleic acid the samples are excited at 631 nm and the resulting fluorescence emission is recorded. The results are shown in FIG. 1.

Using this or similar methodology, a variety of compounds as described herein may be screened for their fluorescence properties when associated with nucleic acids. Similarly, compounds may be screened based upon their relative fluorescence enhancement when associated with RNA versus DNA. Compounds can be readily screened for a particular desired intensity, wavelength, or selectivity for RNA and/or DNA.

Example 8

Association of Compound 20 with Selected Nucleic Acids

A buffer solution of 200 µL of 10 mM TRIS, 1 mM EDTA (pH7.2) is added to the wells of a 96-well microplate. RNA and DNA (calf thymus) dilutions in TE (pH 7.2) are added to the appropriate wells to yield final concentrations of 0-2,000 ng/mL. In separate wells the following combinations of RNA and DNA are prepared:

| RNA (ng/mL) | DNA (ng/mL) |
| --- | --- |
| 0 | 2,000 |
| 400 | 1,600 |
| 800 | 1,200 |
| 1,200 | 800 |
| 1,600 | 400 |
| 2,000 | 0 |

Figure 2:
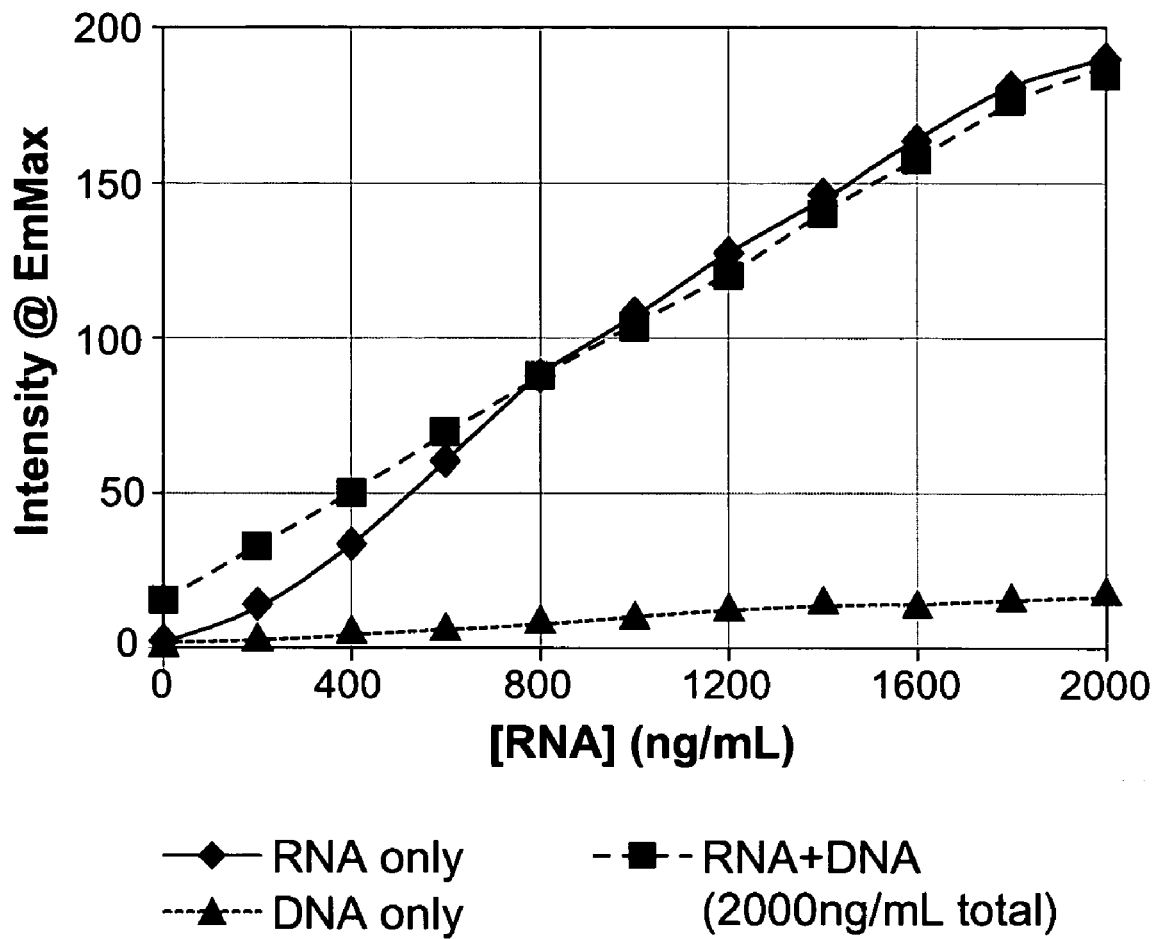
FIG. 2: A plot showing the intensity of the fluorescent signal from Compound 20 in the presence of rRNA, DNA (calf thymus) and a mixture of RNA and DNA in solution. The results indicate that Compound 20, in solution, demonstrates selectivity for rRNA in the presence of 1000 ng/ml of DNA, as described in Example 9.

Compound 20, from a stock solution in DMF, is added to the microplate wells at a final concentration of 0.1 µM. The wells are read at 631 nm/665 nm Ex/Em. Compound 20 demonstrates an increased fluorescent intensity signal with increasing concentrations of RNA but little to no signal when combined with DNA alone. These results are confirmed wherein the combined RNA+DNA results in the same signal intensity for the corresponding concentration of RNA. These results are shown in FIG. 2.

Using this or similar methodology, a variety of compounds as described herein may be screened for utility in detecting RNA in the presence of DNA.

Example 9

Binding of Compound 20 to RNA

Figure 3:
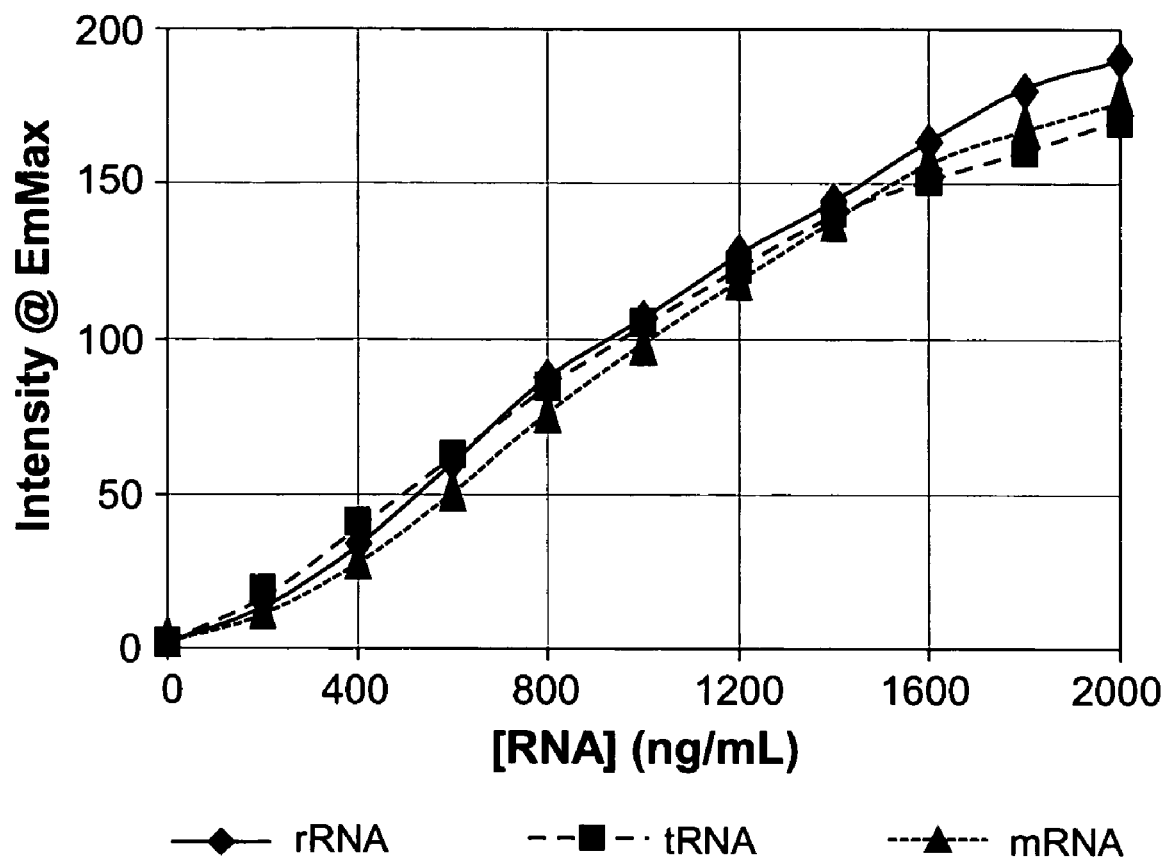
FIG. 3: A plot showing the fluorescence intensity of Compound 20 when associated with rRNA, tRNA and mRNA, respectively, in increasing concentrations of the RNA. Compound 20 demonstrates an equal affinity for the three different species of RNA, as described in Example 8.

A buffer solution of 200 µL of 10 mM TRIS, 1 mM EDTA (pH7.2) is added to the wells of a 96-well microplate. rRNA, tRNA and mRNA dilutions in TE (pH7.2) are added to the appropriate wells to yield final concentrations of 0-2,000 ng/mL. Compound 20, as a stock solution in DMF, is added to the microplate wells to a final concentration of 0.1 µM. The samples in each well are excited at 631 nm, and the fluorescence emission at 665 nm is observed. Compound 20 exhibits comparable fluorescent signal when associated with each variety of RNA tested. The results are shown in FIG. 3.

Example 10

Binding of Compound 20 to RNA, and a Mixture of RNA and DNA

Figure 4:
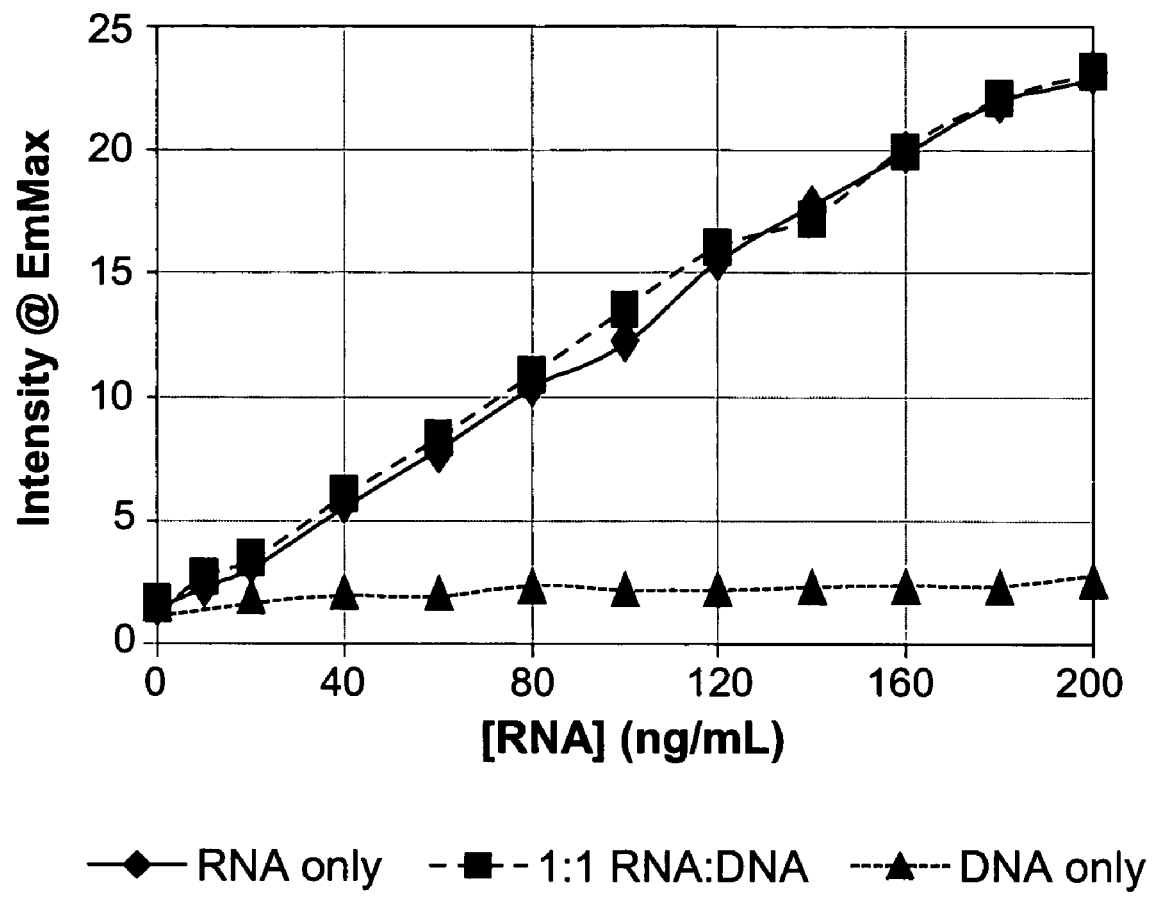
FIG. 4: A plot showing the intensity of the fluorescent signal from Compound 20 at 0.025 µM when bound to varying concentrations of rRNA, or a 1:1 mixture of RNA and DNA in solution.
Figure 4A:
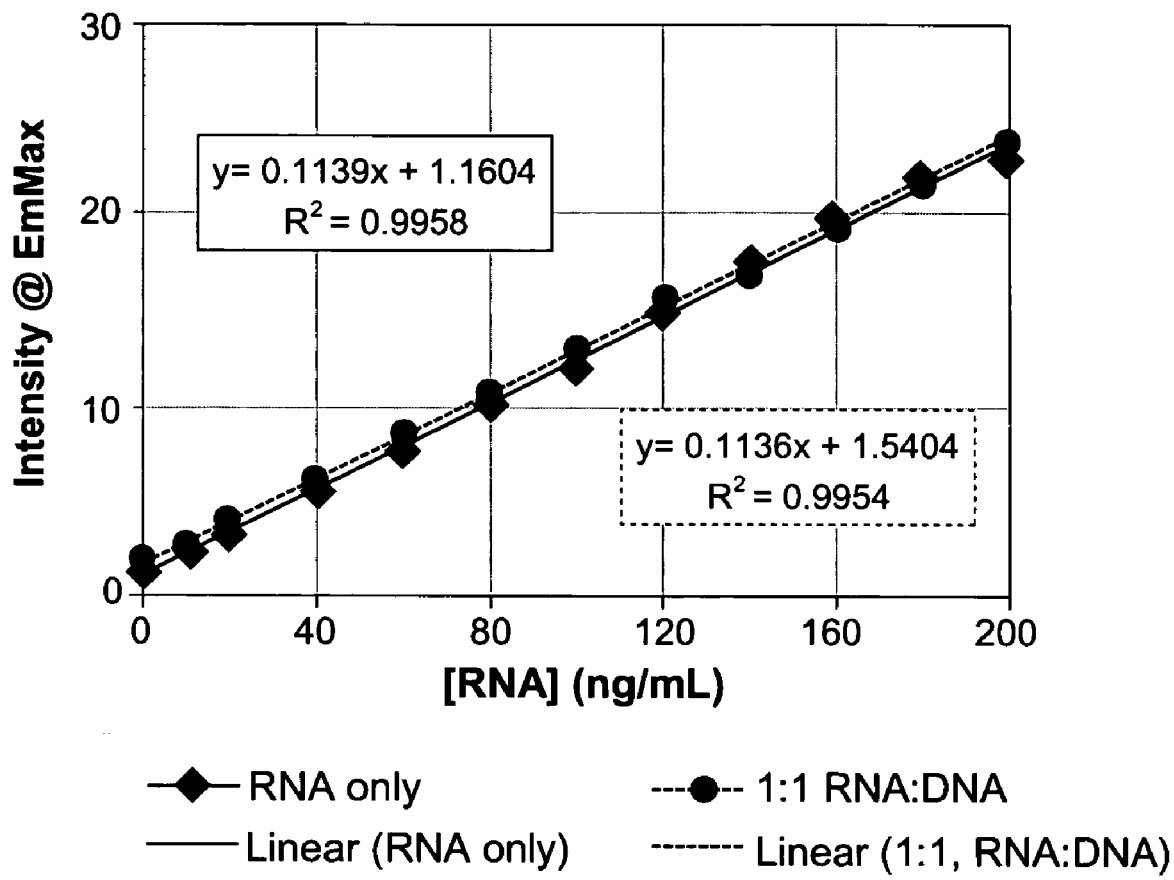
FIG. 4A: A plot showing the linear correlations of the plots of FIG. 4. The similarity of the relationship between fluorescence emission intensity and RNA concentration, even in the presence of varying amounts of DNA, show the selectivity of Compound 20 for RNA, as described in Example 10.

A buffer solution of 200 µL of 10 mM TRIS, 1 mM EDTA (pH 7.2) is added to the wells of a 96-well microplate. RNA and DNA (calf thymus) dilutions in TE (pH 7.2) are added to the appropriate wells to yield final concentrations of 0-200 ng/mL. In separate wells RNA and DNA are combined so that the combined nucleic acid concentration is always 200 ng/mL (For example, RNA and DNA respectively, 0 ng/mL+200 ng/mL, 40 ng/mL+160 ng/mL, 80 ng/mL+120 ng/mL, 120 ng/mL+80 ng/mL, 160 ng/mL+40 ng/mL, and 200 ng/mL+0 ng/mL. Compound 20, prepared using a stock solution in DMF, is added to the microplate wells to a final concentration of 0.025 µM. The wells are excited at 631 nm, and the fluorescence recorded at 665 nm. Compound 20 demonstrates strong selectivity for RNA, as shown in FIGS. 4 and 4A.

Example 11

Detection of Nucleic Acids in Electrophoretic Gels

Compound 20 Stock Solution
A stock solution of Compound 20 is prepared by dissolving 2.1 mg of Compound 20 in 2.0 mL DMSO.

Loading Dye Stock Solution
A loading dye stock solution is prepared by adding 50 µL of Fermentas 6× loading dye solution (s/n R0611) to 550 µL 0.5×TBE.

DNA Stock Solution
3 µL DNA (λ HindIII, Roche, 0.25 µg/µL) is added to 57 µL of loading dye stock solution, and the resulting DNA stock solution is used to prepare a dilution series of DNA in 0.5×TBE.

RNA Stock Solution
1 µL of ribosomal RNA (16S and 23S, Roche, 4 µg/µl) is added to 128 µL loading dye stock solution, and the resulting RNA stock solution is used to prepare a dilution series of RNA in 0.5×TBE.

A precast 1% agarose gel (Embi tec GE-4040) is then loaded with the respective dilution series as follows:

| Lane 1 | 125 ng DNA |
| --- | --- |
| Lane 2 | 62.5 ng DNA |
| Lane 3 | 31.2 ng DNA |
| Lane 4 | 15.6 ng DNA |
| Lane 5 | 7.8 ng DNA |
| Lane 6 | 3.9 ng DNA |
| Lane 7 | Blank |
| Lane 8 | 125 ng RNA |
| Lane 9 | 62.5 ng RNA |
| Lane 10 | 31.2 ng RNA |
| Lane 11 | 15.6 ng RNA |
| Lane 12 | 7.8 ng RNA |
| Lane 13 | 3.9 ng RNA |

The gel is electrophoresed for 15 minutes at 50 V in 0.5× TBE. The gel is then removed from the electrophoresis apparatus and placed directly in a staining solution prepared by adding 25 µL of the Compound 20 stock solution to 50 mL 0.5×TBE, and the gel is stained for 20 minutes. The stained nucleic acid bands are recorded using a Fuji FLA-3000 gel scanner, using 633 nm laser illumination, and a 675 nm filter. The fluorescence intensity of each band is then quantified, with a correction for background fluorescence. The stained RNA bands exhibit a fluorescence signal that is 60-200% more intense than the corresponding DNA bands.

Example 12

Detection of Single-Stranded DNA on a Microarray

A microarray consisting of a dilution series (208 µg, 104 µg, 52 µg, 26 µg, 13 µg, 6.5 µg) of a pUC DNA marker (pUC19 DNA digested with MspI and pUC57 DNA digested with DraI and HindIII, corresponding to pUC Mix Marker 8 supplied by MBI Fermentas, Hanover, Md.) is printed on a slide using a Packard BioChip Piezo microarray spotter. The dilution series is printed using either 50% DMSO/50% $H_2O$ to denature the DNA and render it single stranded, or using 3×SSC to retain double-strandedness. The slide is equilibrated in 0.1×SSC to remove any excess printing buffer, and then soaked in the stain solution at a concentration of 1 µM for the staining compound in ½×TBE for 5 minutes, followed by a 5 minute wash in ½×TBE to remove any excess compound. The slide is then imaged using the Packard ScanArray 5000XL using 633 nm laser excitation. The resulting image clearly shows the top row of ssDNA is stained by the dye down to a concentration of 52 µg, while the dsDNA spots remained undetectable. This suggests that the compound has a higher affinity for ssDNA immobilized on solid supports compared to dsDNA. This affinity may be correlated to a corresponding affinity for RNA that is single stranded.

The preceding examples may be repeated similarly by substituting the specifically described nucleic acid reporter molecules of the preceding examples with those alternative compounds either generically or specifically described in the foregoing description. One skilled in the art can easily ascertain the essential characteristics of the present invention, and without departing from the spirit and scope thereof, make various changes and modifications in teaching of the disclosure in order to adapt to various usages and conditions.

All publications, patents and patent applications mentioned in this specification are herein incorporated by reference to the same extent as if each individual publication, patent or patent application was specifically and individually indicated to be incorporated by reference.

What is claimed is:

1. A nucleic acid reporter molecule of the formula:

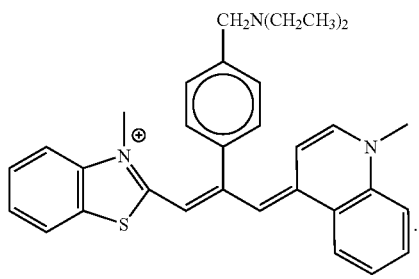

2. A composition comprising a nucleic acid reporter molecule and a sample, wherein the nucleic acid reporter molecule has the formula according to claim 1 wherein the sample comprises biological fluids, buffer solutions, live cells, fixed cells, eukaryotic cells, prokaryotic cells, nucleic acid polymer, nucleotides, nucleosides, a polymeric gel or tissue sections.

3. The composition according to claim 2, wherein the nucleic acid polymer is single stranded RNA, double stranded RNA, single stranded DNA or double stranded DNA.

4. A complex comprising a nucleic acid reporter molecule non-covalently associated with a nucleic acid molecule, wherein the nucleic acid reporter molecule has the formula according to claim 1.

5. The complex according to claim 4, wherein the nucleic acid molecule is single stranded RNA, double stranded RNA, single stranded DNA or double stranded DNA.

6. The complex according to claim 4, wherein the nucleic acid comprises mRNA, tRNA, or rRNA.

7. The complex according to claim 4, wherein the complex is present in a biological sample.

8. The complex according to claim 4, wherein the complex is present in an aqueous or aqueous miscible solution.

9. The complex according to claim 4, wherein the complex is present in an electrophoretic matrix or polymeric gel.

10. A method for detecting the presence or absence of nucleic acid in a sample, wherein the method comprises:
    a) combining a nucleic acid reporter molecule with the sample to prepare a labeling mixture, wherein the nucleic acid reporter molecule has the formula according to claim 1;
    b) incubating the labeling mixture for a sufficient amount of time for the nucleic acid reporter molecule to associate with the nucleic acid in the sample to form an incubated mixture;
    c) illuminating the incubated mixture with an appropriate wavelength to form an illuminated mixture; and
    d) observing the illuminated mixture whereby the presence or absence of the nucleic acid in the sample is detected wherein the sample comprises biological fluids, buffer solutions, live cells, fixed cells, eukaryotic cells, prokaryotic cells, nucleic acid polymer, nucleotides, nucleosides, a polymeric gel or tissue sections.

11. The method according to claim 10, further comprising quantifying the nucleic acid present in the sample.

12. The method according to claim 10, wherein the nucleic acid is RNA.

13. The method according to claim 10, wherein the nucleic acid comprises mRNA, tRNA, or rRNA.

14. The method according to claim 10, wherein the sample is present in or on a microarray or a microwell plate.

15. A method for detecting RNA in the presence of DNA, wherein the method comprises the steps:
    a) combining a nucleic acid reporter molecule with a sample to prepare a labeling mixture, wherein the nucleic acid reporter molecule has a RNA/DNA ratio of fluorescence enhancement greater than about one and wherein the nucleic acid reporter molecule has the formula according to claim 1;
    b) incubating the labeling mixture for a sufficient amount of time for the nucleic acid reporter molecule to associate with RNA in the sample to form an incubated mixture;
    c) illuminating the incubated mixture with an appropriate wavelength to form an illuminated mixture; and
    d) observing the illuminated mixture whereby the RNA is detected in the presence of DNA wherein the sample comprises biological fluids, buffer solutions, live cells, fixed cells, eukaryotic cells, prokaryotic cells, nucleic acid polymer, nucleosides, a polymeric gel or tissue sections.

16. The method according to claim 15, further comprising quantifying the RNA present in the sample.

17. The method according to claim 15, wherein the sample comprises a cell, tissue, or biological fluid.

18. The method according to claim 15, wherein the sample is present in or on a microarray or a microwell plate.

19. The method according to claim 15, wherein the fluorescence of the nucleic acid reporter molecule when non-covalently associated with RNA is distinguishable from the fluorescence of the nucleic acid reporter molecule when non-covalently associated with DNA.

20. The method according to claim 15, wherein the RNA comprises mRNA, tRNA, or rRNA.

21. A kit for detecting nucleic acid in a sample, wherein the kit comprises a nucleic acid reporter molecule that has the formula according to claim 1.

22. The kit according to claim 21, further comprising instructions for detecting RNA in the presence of DNA.

23. The kit according to claim 21, further comprising one or more of a sample preparation reagent, a buffering agent, an aqueous nucleic acid reporter molecule dilution buffer, an organic solvent, nucleic acid control, or an detection reagent.

24. The kit according to claim 23, wherein the nucleic acid reporter molecule dilution buffer contains a detergent.

25. The kit according to claim 24, wherein the detergent is present in a final concentration of about 0.0001% to about 0.005% (w/v).

26. The kit according to claim 24, wherein the detergent is CHAPS, Tween 20, Trinton-X or SDS.

27. The kit according to claims 23, wherein the nucleic acid reporter dilution buffer contains a low concentration of DNA.

28. The kit according to claim 21, further comprising a microarray.

29. The kit according to claim 21, further comprising a microwell plate.

30. A staining solution comprising a nucleic acid reporter molecule and a detergent, wherein the nucleic acid reporter molecule has the formula according to claim 1.

31. The staining solution according to claim 30, wherein the detergent is present at a concentration of about 0.0001% to about 0.005%.

32. The staining solution according to claim 30, wherein the detergent is CHAPS, Triton-X, SDS or Tween 20.

33. The staining solution according to claim 30, further comprising a low concentration of DNA.

34. The staining solution according to claim 33, wherein the DNA is present at a concentration of about 0.1 μg/ml to about 0.5 μg/ml.

* * * * *